US009437833B2

(12) United States Patent
Inoue et al.

(10) Patent No.: US 9,437,833 B2
(45) Date of Patent: Sep. 6, 2016

(54) ORGANIC ELECTROLUMINESCENCE ELEMENT

(75) Inventors: Satoru Inoue, Hino (JP); Hiroto Ito, Yokohama (JP)

(73) Assignee: KONICA MINOLTA, INC., Tokyo (JP)

(*) Notice: Subject to any disclaimer, the term of this patent is extended or adjusted under 35 U.S.C. 154(b) by 248 days.

(21) Appl. No.: 14/239,723

(22) PCT Filed: Aug. 10, 2012

(86) PCT No.: PCT/JP2012/070466
§ 371 (c)(1),
(2), (4) Date: Feb. 19, 2014

(87) PCT Pub. No.: WO2013/031520
PCT Pub. Date: Mar. 7, 2013

(65) Prior Publication Data
US 2014/0191227 A1 Jul. 10, 2014

(30) Foreign Application Priority Data
Aug. 30, 2011 (JP) .................. 2011-187070

(51) Int. Cl.
*H01L 51/50* (2006.01)
*C07F 15/00* (2006.01)
(Continued)

(52) U.S. Cl.
CPC ....... *H01L 51/5028* (2013.01); *C07F 15/0033* (2013.01); *C09K 11/06* (2013.01); *H01L 51/5016* (2013.01); *C09K 2211/1007* (2013.01); *C09K 2211/1029* (2013.01); *C09K 2211/1044* (2013.01); *C09K 2211/1074* (2013.01); *C09K 2211/1088* (2013.01);
(Continued)

(58) Field of Classification Search
CPC .......... H01L 51/0545; H01L 51/0036; H01L 51/0541; H01L 51/5012; H01L 51/50
USPC .......................................... 257/40
See application file for complete search history.

(56) References Cited

U.S. PATENT DOCUMENTS 6,097,147 A 8/2000 Baldo et al.
8,142,909 B2* 3/2012 Beers ................. C07F 15/0033
252/301.16

(Continued)

FOREIGN PATENT DOCUMENTS

JP 2002-260861 A 9/2002
JP 2003-338377 A 11/2003
(Continued)

OTHER PUBLICATIONS

International Preliminary Report on Patentability and Written Opinion in English and Japanese (13 pages).

(Continued)

*Primary Examiner* — Monica D Harrison
(74) *Attorney, Agent, or Firm* — Lucas & Mercanti, LLP

(57) ABSTRACT

An organic electroluminescent element includes a light-emitting layer between an anode and a cathode. The light-emitting layer contains a phosphorescent light-emitting organic metal complex and at least one host compound. The difference in relative dielectric constant between the host compound and the phosphorescent light-emitting organic metal complex is 0 to −0.5, and the difference in dipole moment between the host compound and the phosphorescent light-emitting organic metal complex is 0 to −5.5 debye.

19 Claims, 5 Drawing Sheets

(51) Int. Cl.
   *C09K 11/06* (2006.01)
   *H01L 51/00* (2006.01)

(52) U.S. Cl.
   CPC .. *C09K 2211/1092* (2013.01); *H01L 51/0072* (2013.01); *H01L 51/0073* (2013.01); *H01L 51/0085* (2013.01)

(56) References Cited

U.S. PATENT DOCUMENTS

| | | |
|---|---|---|
| 2007/0088167 A1 | 4/2007 | Lin et al. |
| 2011/0057559 A1 | 3/2011 | Xia et al. |
| 2011/0204333 A1 | 8/2011 | Xia et al. |
| 2011/0233528 A1 | 9/2011 | Levermore et al. |

FOREIGN PATENT DOCUMENTS

| | | |
|---|---|---|
| JP | 2005-112765 A | 4/2005 |
| JP | 2007-012984 A | 1/2007 |
| JP | 2009-081424 A | 4/2009 |
| WO | WO 2007/020718 A1 | 2/2007 |
| WO | 2011004639 A | 1/2011 |
| WO | WO 2011/004639 A1 | 1/2011 |

OTHER PUBLICATIONS

M.A. Baldo et al; Highly efficient phosphorescent emission from organic electroluminescent devices; Nature; vol. 395; Sep. 1998; pp. 151-154.

M.A. Baldo et al; High-efficiency fluorescent organic light-emitting devices using a phosphorescent sensitizer; Nature; vol. 403; No. 17; Feb. 2000; pp. 750-753.

S. Lamansky et al; Highy phosphorescent bis-cyclometalated iridium complexes: synthesis . . . ; J. Am. Chem. Soc.; vol. 123; 2001; pp. 4304-4312.

International Search Report.

Japanese Office Action; Patent Application No. 2013-531198; Dispatch Date: Jan. 19, 2016; Drafting Date: Jan. 14, 2016; Applicant: Koyo International Patent Firm; total of 2 pages; English Translation of Japanese Office Action; total of 3 pages; Grand total of 5 pages.

* cited by examiner

ORGANIC ELECTROLUMINESCENCE ELEMENT

CROSS REFERENCE TO RELATED APPLICATION

This Application is a 371 of PCT/JP2012/070466 filed on Aug. 10, 2012 which, in turn, claimed the priority of Japanese Patent Application No. JP2011-187070 filed on Aug. 30, 2011 both applications are incorporated herein by reference.

TECHNICAL FIELD

The present invention relates to an organic electroluminescent element.

BACKGROUND ART

An organic electroluminescent element (hereinafter, also referred to as an organic EL, element) is a light-emitting element, which includes a light-emitting layer containing a light-emitting compound, provided between a cathode (negative electrode) and an anode (positive electrode). The organic EL element generates excitons in the light-emitting layer by recombination of holes injected from the anode and the electrons injected from the cathode by an applied electric field and emits light (fluorescence or phosphorescence) when the excitons are inactivated. The organic EL element is an entire solid-state element composed of electrodes and an organic film having a thickness of mere about submicrons at most between the electrodes and can emit light at a voltage of about several volts to several tens of volts and is therefore anticipated in application to next-generation flat displays or lighting devices.

Princeton University has developed an organic EL element for practical application and has reported on an organic EL element involving phosphorescent light emission from an excited triplet state (see, for example, Non-Patent Literature 1). Materials emitting phosphorescence at room temperature have been extensively studied since then (see, for example, Patent Literature 1 and Non-Patent Literature 2).

Furthermore, the viable emission efficiency in organic EL elements involving phosphorescent light emission recently discovered is about four times larger in principle than those of conventional elements involving fluorescent emission. Researches and developments of layer configurations and electrodes of light-emitting elements, as well as the developments of materials for the elements, have been conducted all over the world. For example, synthesis of many compounds, mainly, heavy metal complexes such as iridium complexes, has been investigated (see, for example, Non-Patent Literature 3).

Although organic EL devices utilizing phosphorescent light emission have significantly high potential as described above, they have quite different technical issues from organic EL devices involving fluorescent emission, i.e., the control of the position of emission center, in particular, how stable emission of light by recombination in the light-emitting layer can be achieved, which is a key technical challenge for determining the efficiency and lifetime of an element.

Under such a circumstance, a multilayered element having a light-emitting layer, a hole-transporting layer adjoining the light-emitting layer (provided on the anode side of the light-emitting layer), and an electron-transporting layer adjoining the light-emitting layer (provided on the cathode side of the light-emitting layer) have been frequently reported (see, for example, Patent Literature 2). Many of the light-emitting layers are mixed layers containing a host compound and a phosphorescent light-emitting compound as dopants.

According to a recent technology on such a mixed layer containing a host compound and a phosphorescent light-emitting compound as dopants, a host compound and a dopant compound having predetermined dipole moment values are appropriately selected so as to produce an organic EL element having a high luminance efficiency (see, for example, Patent Literatures 3 and 4).

PRIOR ART LITERATURE

Patent Literature

Patent Literature 1: U.S. Pat. No. 6,097,147
Patent Literature 2: Japanese Patent Laid-Open No. 2005-112765
Patent Literature 3: Japanese Patent Laid-Open No. 2009-081424
Patent Literature 4: Japanese Patent No. 4299028
Patent Literature 5: Japanese Patent No. 4105434

Non-Patent Literature

Non-Patent Literature 1: M. A. Baldo et al., Nature, vol. 395, pp. 151-154, (1998)
Non-Patent Literature 2: M. A. Baldo et al., Nature, vol. 403, No. 17, pp. 750-753, (2000)
Non-Patent Literature 3: S. Lamansky et al., J. Am. Chem. Soc., vol. 123, p. 4304, (2001)

SUMMARY OF INVENTION

Technical Problem

During the formation of a light-emitting layer of a mixed layer composed of two or more materials such as a host compound and a dopant compound as described above, the host compound and the dopant compound may separately aggregate depending on the types of the host and dopant compounds, resulting in low light extraction efficiency and lifetime of an organic EL element, i.e., a low quality organic EL element.

An object of the present invention, which has been made in view of the above circumstances, is to provide an organic electroluminescent element having a high light extraction efficiency and a long lifetime.

Means to Solve the Problem

The invention according to Aspect 1 provides an organic electroluminescent element including a light-emitting layer between an anode and a cathode, in which
the light-emitting layer comprises a phosphorescent light-emitting organic metal complex and at least one host compound; and
the host compound and the phosphorescent light-emitting organic metal complex have a difference of 0 to −0.5 in relative dielectric constant (relative permittivity) and have a difference of 0 to −5.5 debye in dipole moment.

The invention according to Aspect 2 provides the organic electroluminescent element according to Aspect 1, in which the host compound and the phosphorescent light-emitting organic metal complex have a difference of 0 to −4 debye in dipole moment.

The invention according to Aspect 3 provides the organic electroluminescent element according to Aspect 1 or 2, in which the phosphorescent light-emitting organic metal complex has an emission wavelength of 480 nm or less.

The invention according to Aspect 4 provides the organic electroluminescent element according to any one of Aspects 1 to 3, in which the phosphorescent light-emitting organic metal complex is coordinated with a ligand having a partial structure represented by a general formula (1):

[Chem. 1]

(General formula (1))

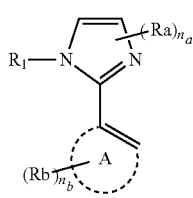

where $R_1$ represents a hydrogen atom, a halogen atom, a cyano group, or an optionally substituted alkyl, alkenyl, alkynyl, alkoxy, amino, silyl, arylalkyl, aryl, heteroaryl, alicyclic, or heteroalicyclic group;

ring A represents a 5- or 6-membered aromatic hydrocarbon ring or aromatic heterocycle;

Ra and Rb each independently represent a hydrogen atom, a halogen atom, a cyano group, or an optionally substituted alkyl, alkenyl, alkynyl, alkoxy, amino, silyl, arylalkyl, aryl, heteroaryl, alicyclic, or heteroalicyclic group;

na represents 1 or 2; and nb represents an integer of 1 to 4.

The invention according to Aspect 5 provides the organic electroluminescent element according to any one of Aspects 1 to 4, in which the phosphorescent light-emitting organic metal complex is coordinated with a ligand having a partial structure represented by a general formula

[Chem. 2]

(General formula (2))

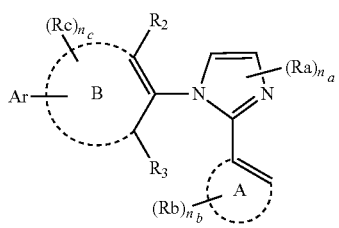

where rings A and B each independently represent a 5- or 6-membered aromatic hydrocarbon ring or aromatic heterocycle;

Ar represents a 5- or 6-membered aromatic hydrocarbon, aromatic heterocyclic, alicyclic, or heteroalicyclic ring;

$R_2$ and $R_3$ each independently represent a hydrogen atom, a halogen atom, a cyano group, or an optionally substituted alkyl, alkenyl, alkynyl, alkoxy, amino, silyl, arylalkyl, aryl, heteroaryl, alicyclic, or heteroalicyclic group;

Ra, Rb, and Rc each independently represent a hydrogen atom, a halogen atom, a cyano group, or an optionally substituted alkyl, alkenyl, alkynyl, alkoxy, amino, silyl, arylalkyl, aryl, heteroaryl, alicyclic, or heteroalicyclic group;

na and nc each independently represent 1 or 2; and nb represents an integer of 1 to 4.

The invention according to Aspect 6 provides the organic electroluminescent element according to any one of Aspects 1 to 5, in which the phosphorescent light-emitting organic metal complex is an organic metal complex represented by a general formula (3):

[Chem. 3]

(General formula (3))

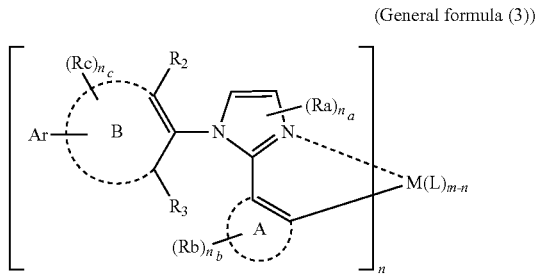

where rings A and B each independently represent a 5- or 6-membered aromatic hydrocarbon ring or aromatic heterocycle;

Ar represents a 5- or 6-membered aromatic hydrocarbon, aromatic heterocyclic, alicyclic, or heteroalicyclic ring;

$R_2$ and $R_3$ each independently represent a hydrogen atom, a halogen atom, a cyano group, or an optionally substituted alkyl, alkenyl, alkynyl, alkoxy, amino, silyl, arylalkyl, aryl, heteroaryl, alicyclic, or heteroalicyclic group;

Ra, Rb, and Rc each independently represent a hydrogen atom, a halogen atom, a cyano group, or an optionally substituted alkyl, alkenyl, alkynyl, alkoxy, amino, silyl, arylalkyl, aryl, heteroaryl, alicyclic, or heteroalicyclic group;

na and nc each independently represent 1 or 2;

nb represents an integer of 1 to 4;

L represents one or more of monoanionic bidentate ligands coordinated to M;

M represents a transition metal atom having an atomic number of 40 or more and belonging to any one of Groups 8 to 10 of the periodic table;

m represents an integer of 1 to 3;

n represents 1 or more; and m+n is 2 or 3.

The invention according to Aspect 7 provides the organic electroluminescent element according to Aspect 5 or 6, in which $R_2$ and/or $R_3$ represent an alkyl group.

The invention according to Aspect 8 provides the organic electroluminescent element according to Aspect 7, in which $R_2$ and/or $R_3$ represents an alkyl group having two or more carbon atoms.

The invention according to Aspect 9 provides the organic electroluminescent element according to any one of Aspects 5 to 8, in which $R_2$ and $R_1$ represent alkyl groups.

The invention according to Aspect 10 provides the organic electroluminescent element according to Aspect 9, in which $R_2$ and $R_3$, represent alkyl groups having two or more carbon atoms.

The invention according to Aspect 11 provides the organic electroluminescent element according to Aspect 5 or 6, in which ring A is a benzene ring.

The invention according to Aspect 12 provides the organic electroluminescent element according to any one of Aspects 5 to 11, in which Ar is a benzene ring.

The invention according to Aspect 13 provides the organic electroluminescent element according to Aspect 6, in which the general formula (3) is represented by a general formula (3-1):

[Chem. 4]

(General formula (3-1))

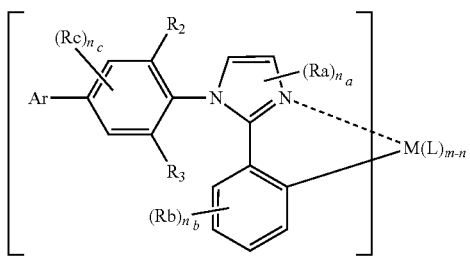

where Ar, $R_2$, $R_3$, Ra, Rb, Rc, na, nb, nc, M, L, m, and n are synonymous with Ar, $R_2$, $R_3$, Ra, Rb, Rc, na, nb, nc, M, L, m, and n in the formula (3).

The invention according to Aspect 14 provides the organic electroluminescent element according to Aspect 13, in which M is Ir.

The invention according to Aspect 15 provides the organic electroluminescent element according to any one of Aspects 1 to 14, in which the host compound has a partial structure represented by a general formula (4):

[Chem. 5]

(General formula (4))

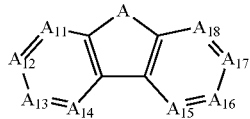

where A represents an O or S atom or an $NR_1$, group; $A_{11}$ to $A_{18}$ each independently represent a N atom or $CR_2$; $R_1$ and $R_2$ each independently represent a bonding hand, a hydrogen atom, or a substituent; and if there are a plurality of $CR_2$, they may be the same or different.

Advantageous Effects of Invention

The present invention can provide an organic electroluminescent element having a high light extraction efficiency and a long lifetime.

DESCRIPTION OF EMBODIMENTS

Figure 1:
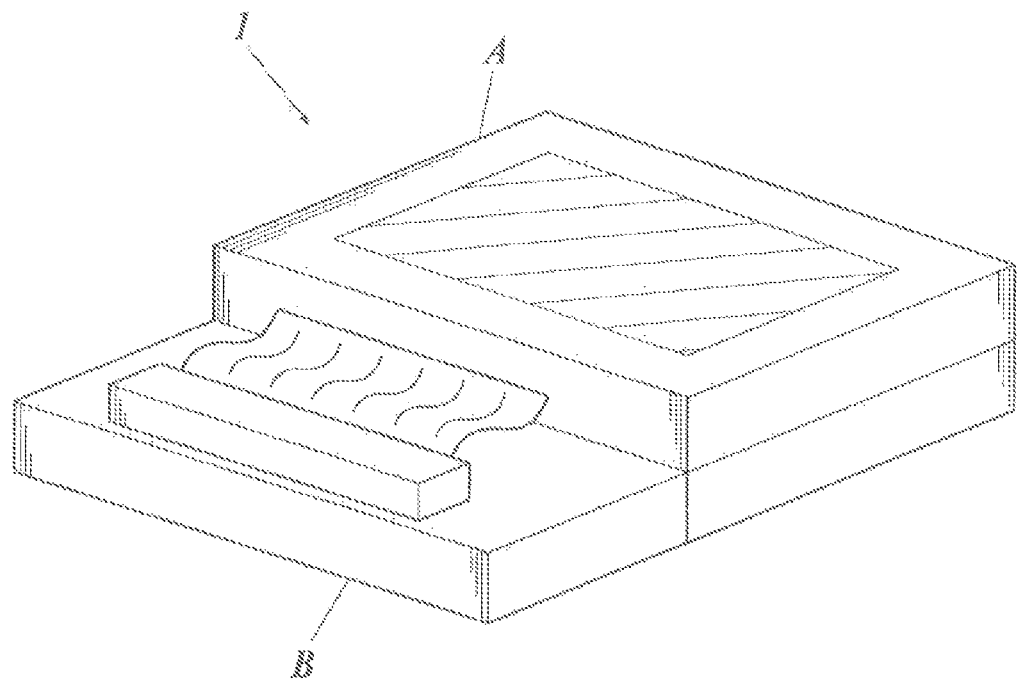
FIG. 1 is a schematic diagram illustrating an example of a display device composed of organic EL elements.

An exemplary embodiment for carrying out the present invention will now be described in detail. The present invention should not be limited thereto.

The present inventors, who have diligently studied to achieve the object, have found that two or more materials forming a light-emitting layer, i.e., a host compound and a phosphorescent light-emitting organic metal complex, can be prevented from aggregating immediately after formation of the film by controlling the difference in dipole moment between the host compound and the phosphorescent light-emitting organic metal complex to 0 to −5.5 debye and that such control can also prevent aggregation during operation. It was also found that a difference in dipole moment of 0 to −4 debye was particularly preferred.

It was also found that the aggregation during operation is more effectively prevented by controlling the difference in relative dielectric constant between the host compound and the phosphorescent light-emitting organic metal complex to 0 to 0.5 debye, in addition to the reduction in the difference in dipole moment, resulting in an increase in quality.

(Dipole Moment)

The term "dipole moment" in the present invention refers to deviation of charge in a compound. The dipole moment can be determined by an AM1 method using a semiempirical molecular orbital package (MOPAC).

(Dielectric Constant)

The dielectric constant can be determined by calculation using a functional based on the density functional theory described in Organic Electronics, 10, 532-535, (2009).

Compounds according to the present invention will now be described.

(Phosphorescent Light-Emitting Organic Metal Complex Having Metal Atom Coordinated with Ligand Having Structure Represented by the General Formula (1))

In the formula (1), $R_1$ represents a hydrogen atom, a halogen atom, a cyano group, or an optionally substituted alkyl, alkenyl, alkynyl, alkoxy, amino, silyl, arylalkyl, aryl, heteroaryl, alicyclic, or heteroalicyclic group.

In the formula (1), ring A represents a 5- or 6-membered aromatic hydrocarbon ring or aromatic heterocycle.

In the formula (1), Ra and Rb each independently represent a hydrogen atom, a halogen atom, a cyano group, or an optionally substituted alkyl, alkenyl, alkynyl, alkoxy, amino, silyl, arylalkyl, aryl, heteroaryl, alicyclic, or heteroalicyclic group; na represents 1 or 2; and nb represents an integer of 1 to 4.

(Phosphorescent Light-Emitting Dopant Compound Represented by the General Formula (2))

In the formula (2), the 5- or 6-membered aromatic hydrocarbon ring represented by ring A or B is, for example, a benzene ring.

In the formula (2), examples of the 5- or 6-membered aromatic hydrocarbon ring represented by ring A or B include furan, thiophene, oxazole, pyrrole, pyridine, pyridazine, pyrimidine, pyrazine, triazine, oxadiazole, triazole, imidazole, pyrazole, and thiazole rings. Preferably, ring B is a benzene ring. More preferably, ring A is a benzene ring.

In the formula (2), examples of the aromatic hydrocarbon ring represented by Ar include benzene, biphenyl, naphthalene, azulene, anthracene, phenanthrene, pyrene, chrysene, naphthacene, triphenylene, o-terphenyl, m-terphenyl, p-terphenyl, acenaphthene, coronene, fluorene, fluoranthrene, naphthacene, pentacene, perylene, pentaphene, picene, pyrene, pyranthrene, and anthranthrene rings.

In the formula (2), examples of the aromatic heterocycle represented by Ar include silole, furan, thiophene, oxazole, pyrrole, pyridine, pyridazine, pyrimidine, pyrazine, triazine, oxadiazole, triazole, imidazole, pyrazole, thiazole, indole, benzimidazole, benzothiazole, benzoxazole, quinoxaline, quinazoline, phthalazine, thienothiophene, and carbazole rings, and azacarbazole rings (refer to rings each having one or more nitrogen atoms substituted for carbon atom(s) on a carbazole ring), and dibenzosilole, dibenzofuran, dibenzothiophene rings, and rings each having one or more nitrogen atoms substituted for carbon atom(s) on a dibenzofuran or benzothiophene ring, and benzodifuran, benzodithiophene, acridine, benzoquinoline, phenazine, phenanthridine, phenanthroline, cyclazine, quindoline, thebenidine, quinindoline, triphenodithiazine, triphenodioxazine, phenanthrazine, anthrazine, perimidine, naphthofuran, naphthothiophene, naphthodifuran, naphthodithiophene, anthrafuran, anthradifuran, anthrathiophene, anthradithiophene, thianthrene, phenoxathiin, dibenzocarbazole, indolocarbazole, and dithienobenzene rings.

In the formula (2), examples of the alicyclic ring represented by Ar include cycloalkane groups such as cyclopentane and cyclohexane rings, cycloalkoxy groups such as cyclopentyloxy and cyclohexyloxy groups, cycloalkylthio group such as cyclopentylthio and cyclohexylthio groups, a cyclohexylaminosulfonyl group, and tetrahydronaphthalene, 9,10-dihydroanthracene, and biphenylene rings.

In the formula (2), examples of the heteroalicyclic ring represented by Ar include epoxy, aziridine, thiirane, oxetane, azetidine, thietane, tetrahydrofuran, dioxolane, pyrrolidine, pyrazolidine, imidazolidine, oxazolidine, tetrahydrothiophene, sulfolane, thiazolidine, ε-caprolactone, ε-caprolactam, piperidine, hexahydropyridazine, hexahydropyrimidine, piperazine, morpholine, tetrahydropyran, 1,3-dioxane, 1,4-dioxane, trioxane, tetrahydrothiopyran, thiomorpholine, thiomorpholine-1,1-dioxide, pyranose, diazabicyclo[2,2,2]-octane, phenoxazine, phenothiazine, oxanthrene, thioxanthene, and phenoxathiin rings.

These rings represented by Ar in the formula (2) may further include the following substituents (hereinafter, each referred to as substituent Rx), and such substituents may be bonded to each other to form a ring.

Examples of the substituent Rx include alkyl groups (e.g., methyl, ethyl, propyl, isopropyl, tert-butyl, pentyl, hexyl, octyl, dodecyl, tridecyl, tetradecyl, and pentadecyl groups), alkenyl groups (e.g., vinyl and aryl groups), alkynyl groups (e.g., ethynyl and propargyl groups), alicyclic groups (for example, cycloalkyl groups (e.g., cyclopentyl and cyclohexyl groups), cycloalkoxy groups (e.g., cyclopentyloxy and cyclohexyloxy groups), cycloalkylthio groups (e.g., cyclopentylthio and cyclohexylthio groups), and monovalent groups derived from, for example, tetrahydronaphthalene, 9,10-dihydroanthracene, and biphenylene rings), heteroalicyclic groups (e.g., monovalent groups derived from, for example, epoxy, aziridine, thiirane, oxetane, azetidine, thietane, tetrahydrofuran, dioxolane, pyrrolidine, pyrazolidine, imidazolidine, oxazolidine, tetrahydrothiophene, sulfolane, thiazolidine, ε-caprolactone, ε-caprolactam, piperidine, hexahydropyridazine, hexahydropyrimidine, piperazine, morpholine, tetrahydropyran, 1,3-dioxane, 1,4-dioxane, trioxane, tetrahydrothiopyran, thiomorpholine, thiomorpholine-1,1-dioxide, pyranose, diazabicyclo[2,2,2]-octane, phenoxazine, phenothiazine, oxanthrene, thioxanthene, and phenoxathiin rings), aromatic hydrocarbon groups (e.g., monovalent groups derived from, for example, benzene, biphenyl, naphthalene, azulene, anthracene, phenanthrene, pyrene, chrysene, naphthacene, triphenylene, o-terphenyl, m-terphenyl, p-terphenyl, acenaphthene, coronene, fluorene, fluoranthrene, naphthacene, pentacene, perylene, pentaphene, picene, pyrene, pyranthrene, and anthranthrene rings), aromatic heterocyclic groups (e.g., monovalent groups derived from, for example, silole, furan, thiophene, oxazole, pyrrole, pyridine, pyridazine, pyrimidine, pyrazine, triazine, oxadiazole, triazole, imidazole, pyrazole, thiazole, indole, benzimidazole, benzothiazole, benzoxazole, quinoxaline, quinazoline, phthalazine, thienothiophene, and carbazole rings, and azacarbazole rings (refer to rings each having one or more nitrogen atoms substituted for carbon atom(s) on a carbazole ring), and dibenzosilole, dibenzofuran, dibenzothiophene, and benzothiophene rings, and rings each having one or more nitrogen atoms substituted for carbon atom(s) on a dibenzofuran ring, and benzodifuran, benzodithiophene, acridine, benzoquinoline, phenazine, phenanthridine, phenanthroline, cyclazine, quindoline, thebenidine, quinindoline, triphenodithiazine, triphenodioxazine, phenanthrazine, anthrazine, perimidine, naphthofuran, naphthothiophene, naphthodifuran, naphthodithiophene, anthrafuran, anthradifuran, anthrathiophene, anthradithiophene, thianthrene, phenoxathiin, dibenzocarbazole, indolocarbazole, and dithienobenzene rings), alkoxy groups (e.g., methoxy, ethoxy, propyloxy, pentyloxy, hexyloxy, octyloxy, and dodecyloxy groups), aryloxy groups (e.g., phenoxy and naphthyloxy groups), alkylthio groups (e.g., methylthio, ethylthio, propylthio, pentylthio, hexylthio, octylthio, and dodecylthio groups), arylthio groups (e.g., phenylthio, and naphthylthio groups), alkoxycarbonyl groups (e.g., methyloxycarbonyl, ethyloxycarbonyl, butyloxycarbonyl, octyloxycarbonyl, and dodecyloxycarbonyl groups), aryloxycarbonyl groups (e.g., phenyloxycarbonyl and naphthyloxycarbonyl groups), sulfamoyl groups (e.g., aminosulfonyl, methylaminosulfonyl, dimethylaminosulfonyl, butylaminosulfonyl, hexylaminosulfonyl, cyclohexylaminosulfonyl, octylaminosulfonyl, dodecylaminosulfonyl, phenylaminosulfonyl, naphthylaminosulfonyl, and 2-pyridylaminosulfonyl groups), acyl groups (e.g., acetyl, ethylcarbonyl, propylcarbonyl, pentylcarbonyl, cyclohexylcarbonyl, octylcarbonyl, 2-ethylhexylcarbonyl, dodecylcarbonyl, phenylcarbonyl, naphthylcarbonyl, and pyridylcarbonyl groups), acyloxy groups (e.g., acetyloxy, ethylcarbonyloxy, butylcarbonyloxy, octylcarbonyloxy, dodecylcarbonyloxy, and phenylcarbonyloxy groups), amido groups (e.g., methylcarbonylamino, ethylcarbonylamino, dimethylcarbonylamino, propylcarbonylamino, pentylcarbonylamino, cyclohexylcarbonylamino, 2-ethylhexylcarbonylamino, octylcarbonylamino, dodecylcarbonylamino, phenylcarbonylamino, and naphthylcarbonylamino groups), carbamoyl groups (e.g., aminocarbonyl, methylaminocarbonyl, dimethylaminocarbonyl, propylaminocarbonyl, pentylaminocarbonyl, cyclohexylaminocarbonyl, octylaminocarbonyl, 2-ethylhexylaminocarbonyl, dodecylaminocarbonyl, phenylaminocarbonyl, naphthylaminocarbonyl, and 2-pyridylaminocarbonyl groups), ureido groups (e.g., methylureido, ethylureido, pentylureido, cyclohexylureido, octylureido, dodecylureido, phenylureido, naphthylureido, and 2-pyridylaminoureido groups), sulfinyl groups (e.g., methylsulfinyl, ethylsulfinyl, butylsulfinyl, cyclohexylsulfinyl, 2-ethylhexylsulfinyl, dodecylsulfinyl, phenylsulfinyl, naphthylsulfinyl, and 2-pyridylsulfinyl groups), alkylsulfonyl groups (e.g., methylsulfonyl, ethylsulfonyl, butylsulfonyl, cyclohexylsulfonyl, 2-ethylhexylsulfonyl, and dodecylsulfonyl groups), arylsulfonyl or heteroarylsulfonyl groups (e.g., phenylsulfonyl, naphthylsulfonyl, and 2-pyridylsulfonyl groups), amino groups (e.g., amino, ethylamino, dimethylamino, butylamino, cyclopentylamino, 2-ethylhexylamino, dodecylamino, anilino, naphthylamino, and 2-pyridylamino groups), halogen atoms (e.g., fluorine, chlorine, and bromine atoms), fluorohydrocarbon groups (e.g., fluoromethyl, trifluoromethyl, pentafluoroethyl, and pentafluorophenyl groups), a cyano group, a nitro group, a hydroxy group, a mercapto group, silyl groups (e.g., trimethylsilyl, triisopropylsilyl, triphenylsilyl, and phenyldiethylsilyl groups), and a phosphono group.

Ar is preferably an aromatic hydrocarbon ring or an aromatic heterocycle, more preferably an aromatic hydrocarbon ring, and most preferably a benzene ring.

In the formula (2), $R_2$ and $R_3$ each independently represent a hydrogen atom, a halogen atom, a cyano, an alkyl group, an alkenyl group, an alkynyl group, an alkoxy group, an amino group, a silyl group, an arylalkyl group, an aryl group, a heteroaryl group, an alicyclic group, or a heteroalicyclic group and may have a substituent. At least one of the $R_2$ and $R_3$ is an alkyl or cycloalkyl group having two or more carbon atoms.

Examples of the aryl group and the heteroaryl group represented by $R_2$ or $R_3$ in the formula (2) include monovalent groups derived from aromatic hydrocarbon or aromatic heterocyclic rings represented by Ar in the formula (2).

Examples of the alicyclic group and the heteroalicyclic group represented by $R_2$ or $R_3$ in the formula (2) include monovalent groups derived from alicyclic or heteroalicyclic rings represented by Ar in the formula (2).

$R_2$ and $R_3$ are preferably both alkyl or cycloalkyl groups having two or more carbon atoms. Alternatively, at least one of the $R_2$ and $R_3$ is also preferably a branched alkyl group having three or more carbon atoms. More preferably, $R_2$ and $R_3$ are both branched alkyl groups having three or more carbon atoms.

In the formula (2), Ra, Rb, and Rc each independently represent a hydrogen atom, a halogen atom, a cyano group, an alkyl group, an alkenyl group, an alkynyl group, an alkoxy group, an amino group, a silyl group, an arylalkyl group, an aryl group, a heteroaryl group, an alicyclic group, or a heteroalicyclic group and may have a substituent.

Examples of the aryl group and the heteroaryl group represented by Ra, Rb, or Rc in the formula (2) include monovalent groups derived from aromatic hydrocarbon or aromatic heterocyclic rings represented by Ar in the formula (2).

Examples of the alicyclic group and the heteroalicyclic group represented by Ra, Rb, or Rc in the formula (2) include monovalent groups derived from alicyclic and heteroalicyclic rings represented by Ar in the formula (2).

In the formula (2), na and nc each independently represent 1 or 2; and nb represents an integer of 1 to 4.

The phosphorescent light-emitting dopant compounds represented by the formula (2) according to the present invention are preferably those represented by the formula (3) or the formula (3-1).

(Phosphorescent Light-Emitting Dopant Compound (Organic Metal Complex) Represented by the Formula (3) or Formula (3-1))

In the formulae (3) and (3-1), Ar, R2, R3. Ra, Rb, Rc, na, nb, and nc are synonymous with Ar, R2, R3, Ra, Rb, Rc, na, nb, and nc in the formula (2). In the formula (3), rings A and B are synonymous with rings A and B in the formula (2).

Examples of the monoanionic bidentate ligand coordinated to M, represented by L, in the formulae (3) and (3-1) include the following ligands:

[Chem. 6]

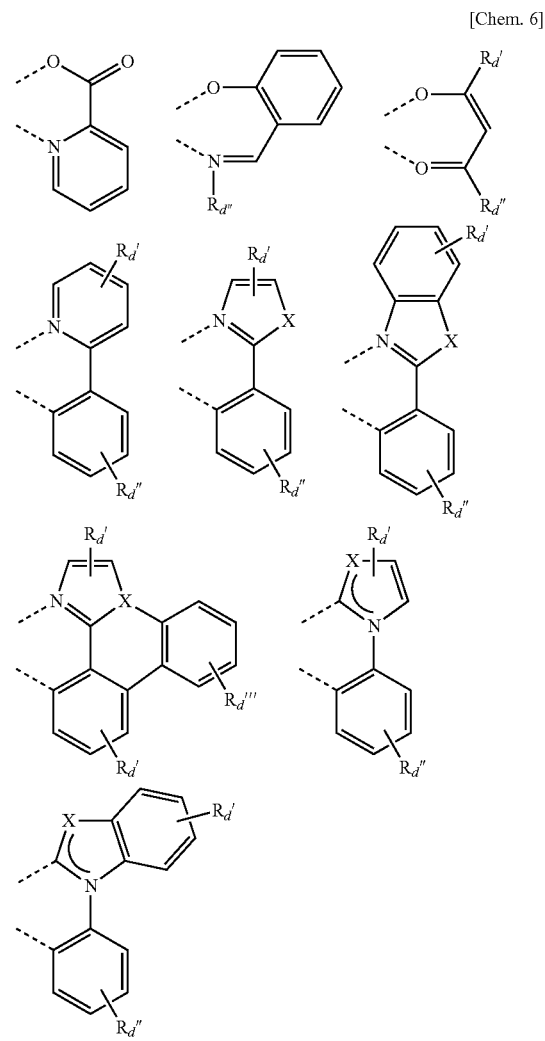

where Rd', Rd'', and Rd''' each independently represent a hydrogen atom or a substituent. Examples of the substituent represented by Rd', Rd'', or Rd''' include those exemplified as the substituent Rx represented by Ar in the formula (2).

In the formulae (3) and (3-1), M is a transition metal atom having an atomic number of 40 or more and belonging to any one of groups 8 to 10 of the periodic table and is preferably Os, Ir, or Pt and more preferably Ir.

In the formulae (3) and (3-1), m represents an integer of 0 to 2; n represents 1 or more; and m+n is 2 or 3. Preferably, n is 3 or 2, and also m is 0.

The compounds represented by the formula (2), (3), or (3-1) according to the present invention can be synthesized in accordance with a known method, as is described in International Patent Publication No. WO2006-121811.

Non-limiting examples of the phosphorescent light-emitting dopant compound that can be preferably used in the present invention are shown below:

[Chem. 7]
DP-1 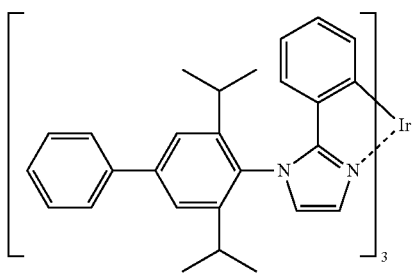 DP-2 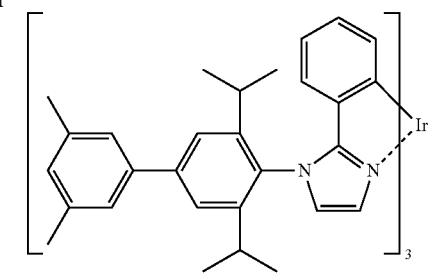
DP-3 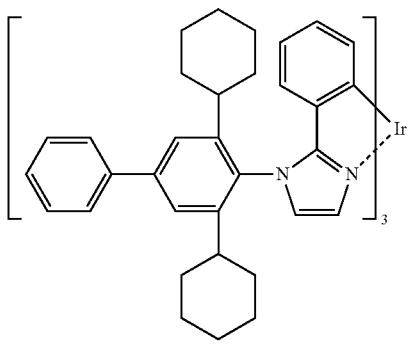 DP-4 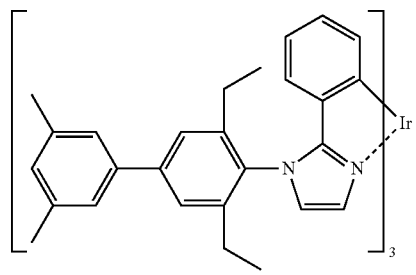
DP-5 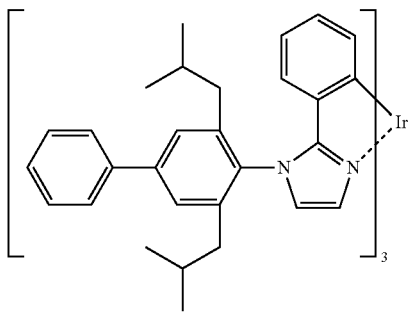 DP-6 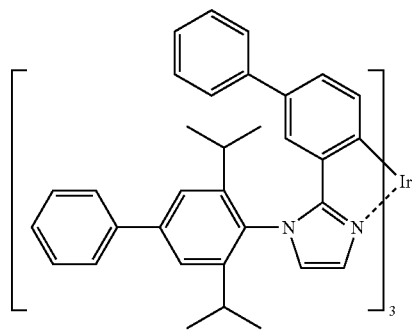
DP-7 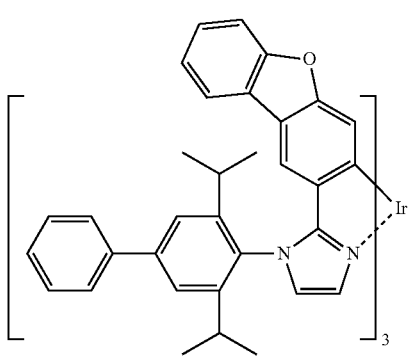 DP-8 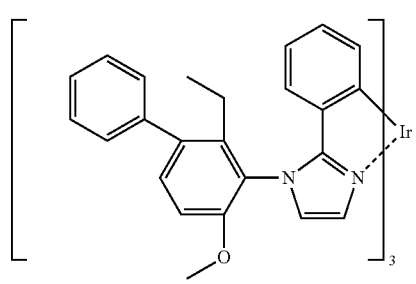

-continued
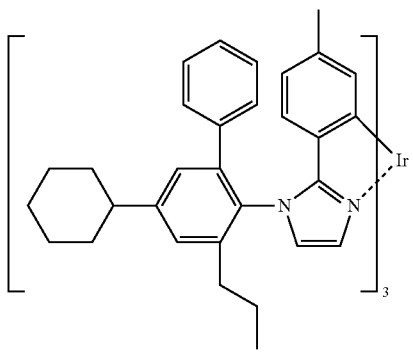
DP-9
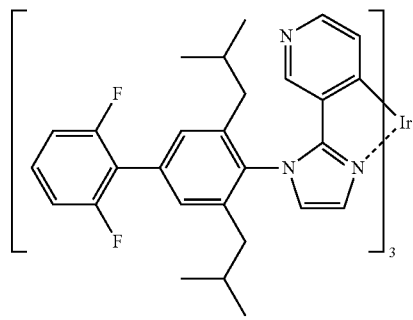
DP-10
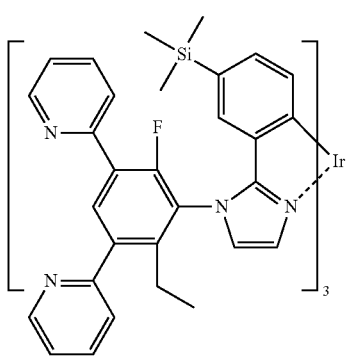
DP-11
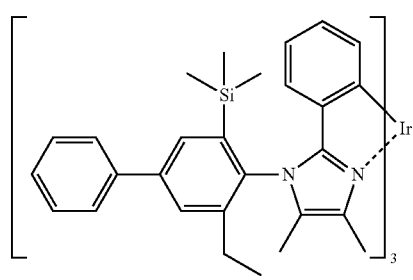
DP-12
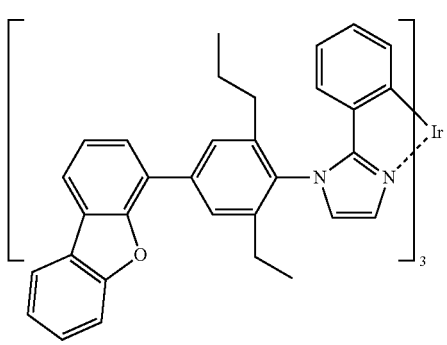
DP-13
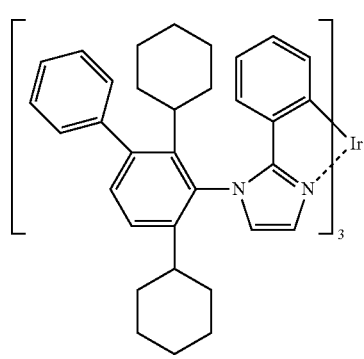
DP-14
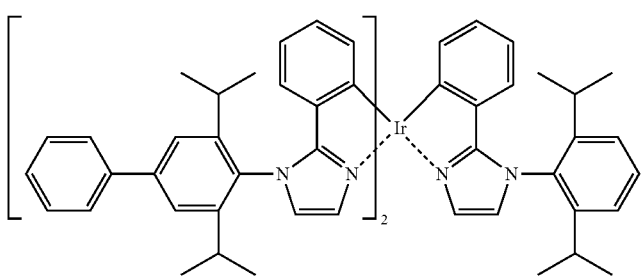
DP-15

-continued
[Chem. 9]
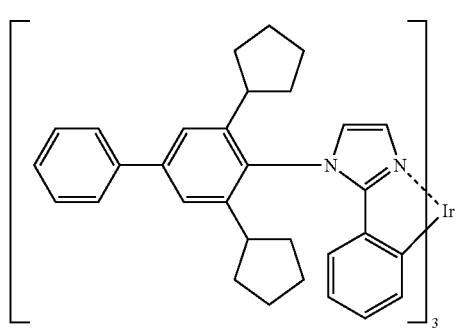
DP-16
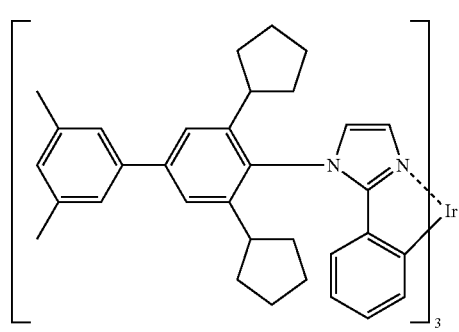
DP-17
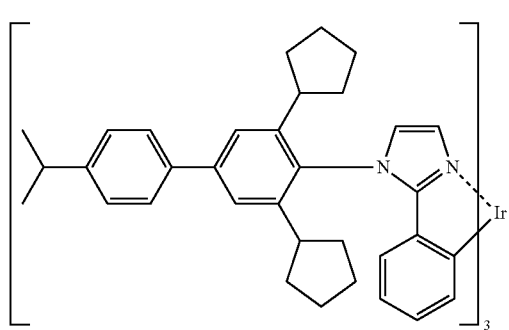
DP-18
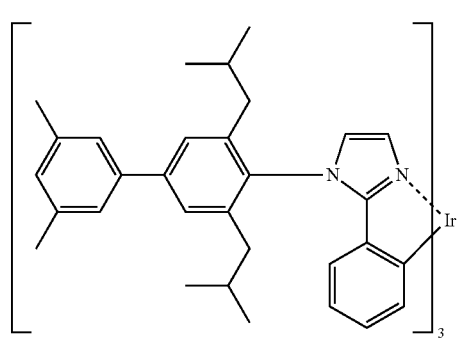
DP-19
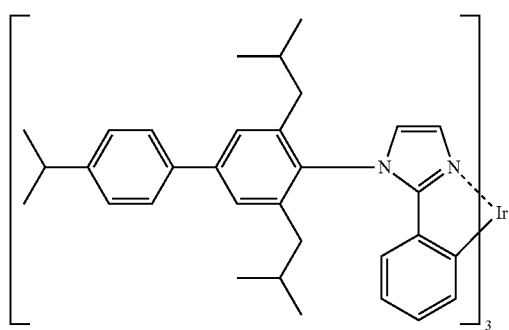
DP-20
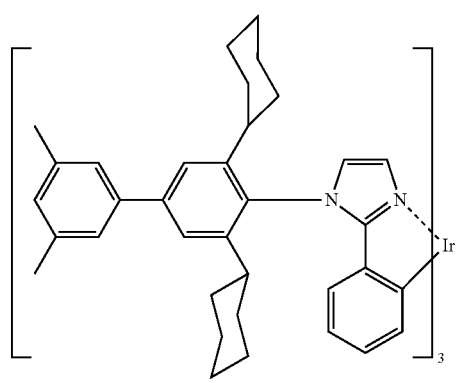
DP-21
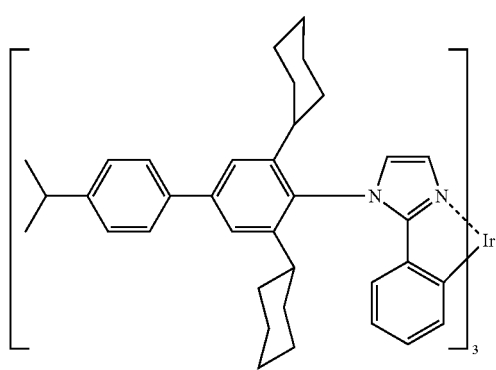
DP-22
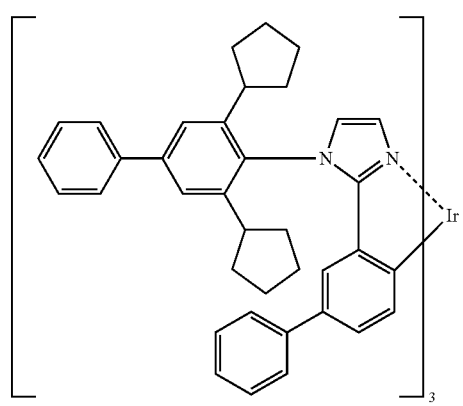
DP-23

-continued
[Chem. 10]
DP-24
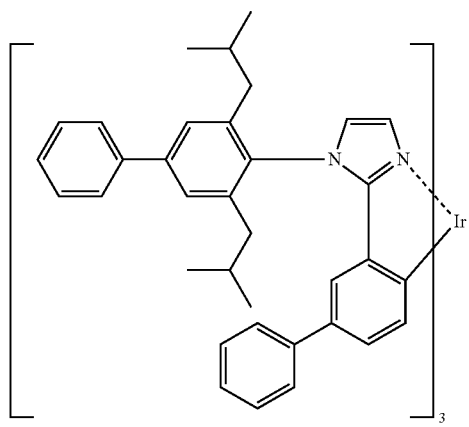
DP-25
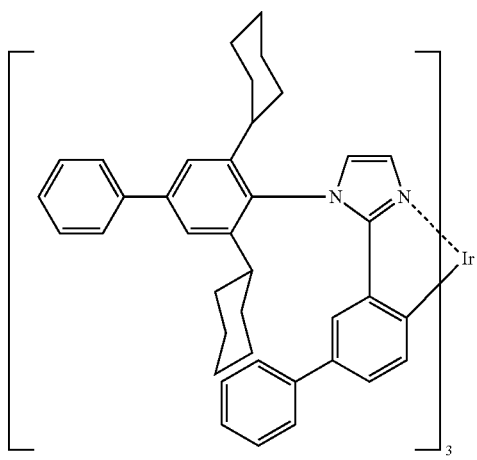
DP-26
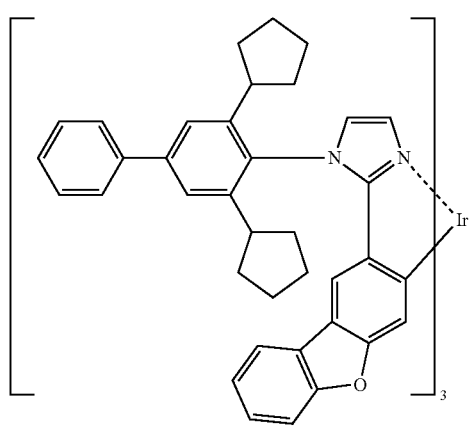
DP-27
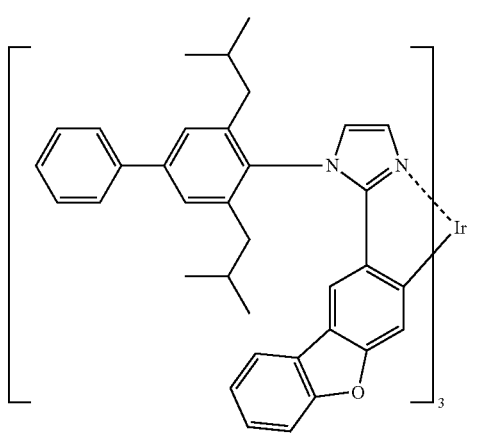
DP-28
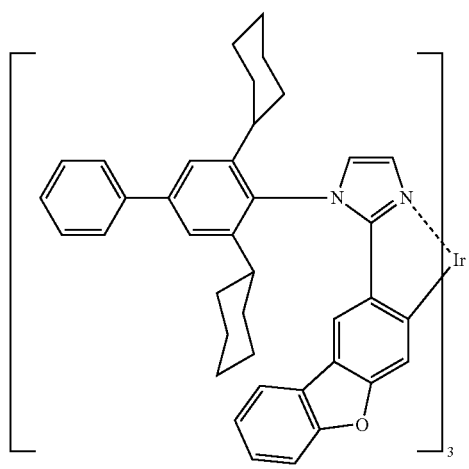
DP-29
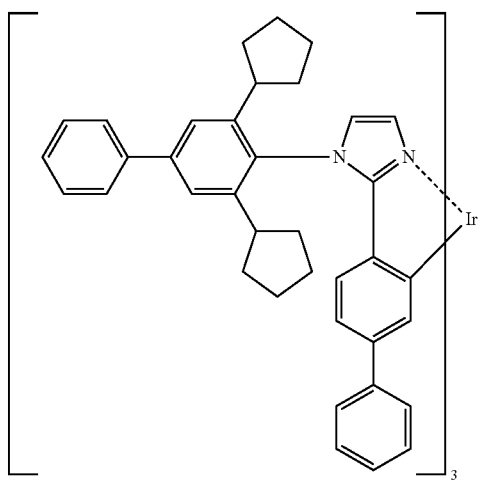

[Chem. 11]
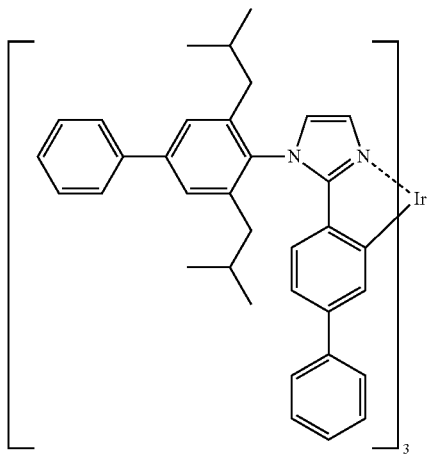
DP-30
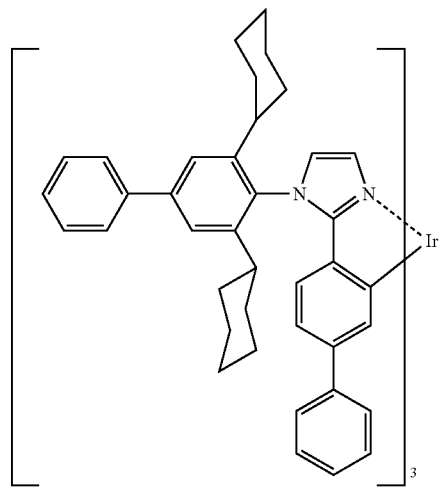
DP-31
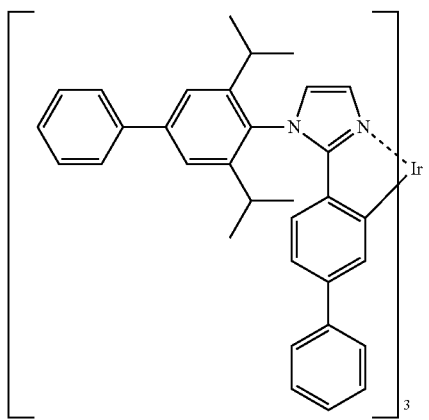
DP-32
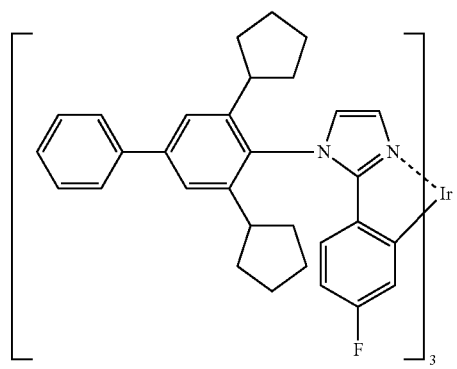
DP-33
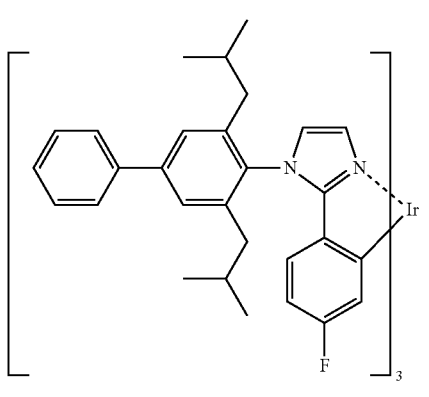
DP-34
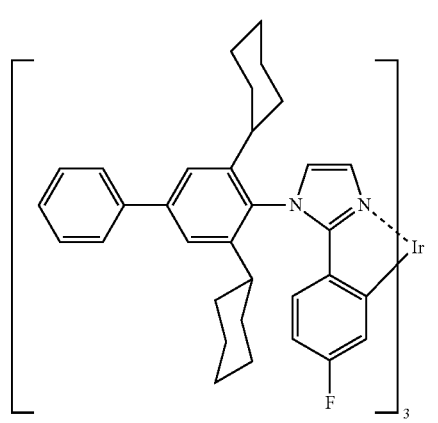
DP-35

[Chem. 12]
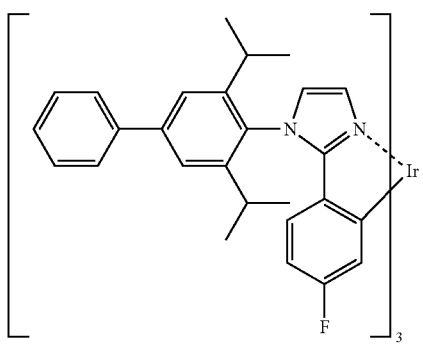
DP-36
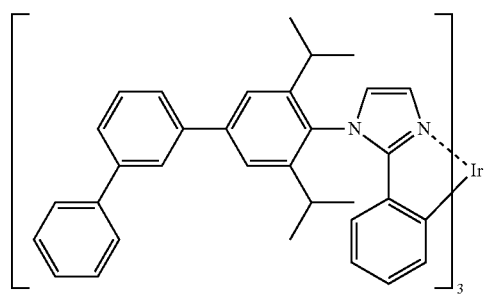
DP-37
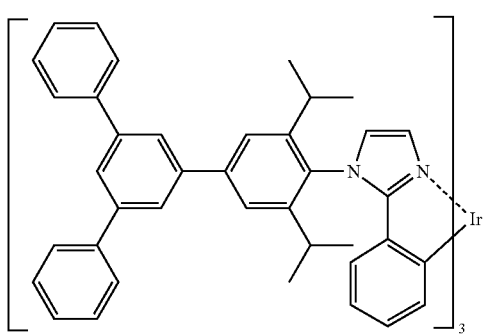
DP-38
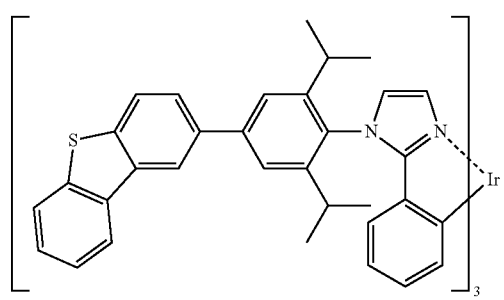
DP-39
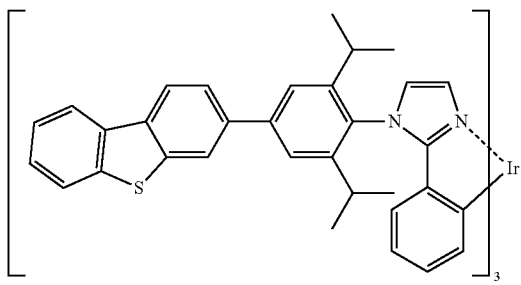
DP-40
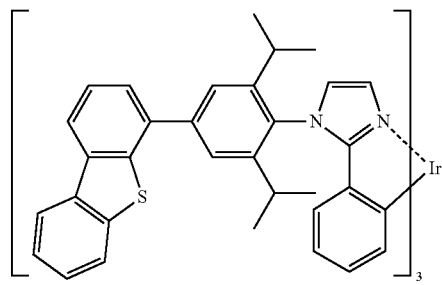
DP-41
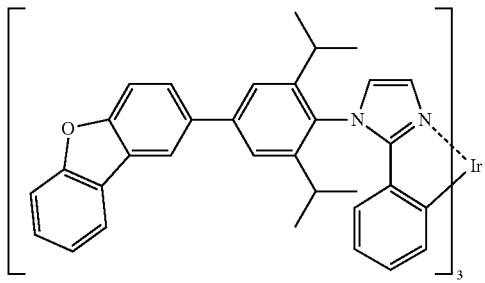
DP-42
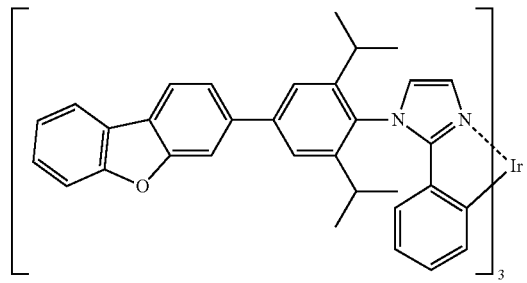
DP-43

[Chem. 13]
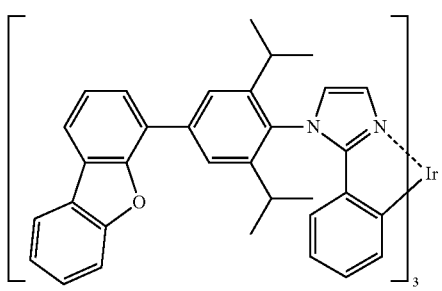
DP-44
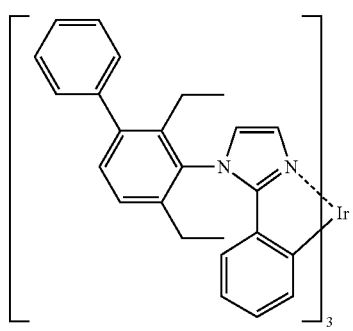
DP-45
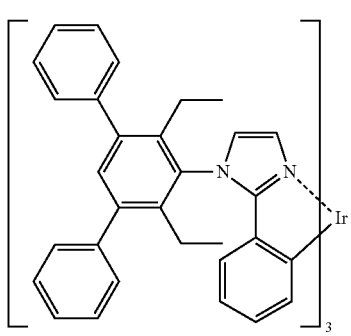
DP-46
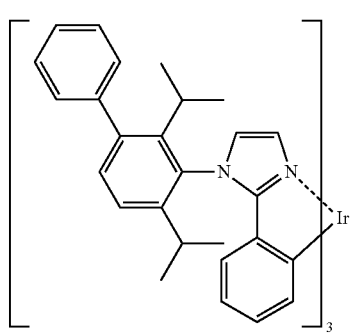
DP-47
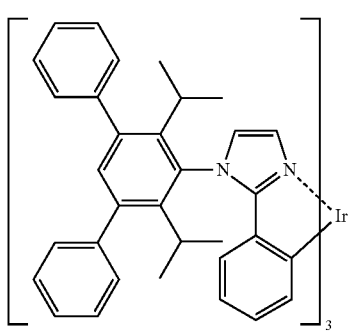
DP-48
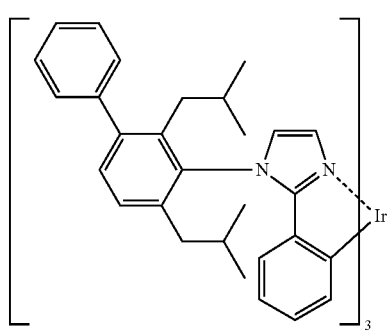
DP-49
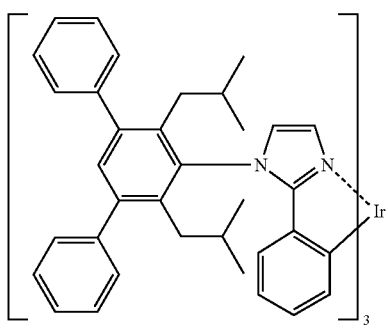
DP-50
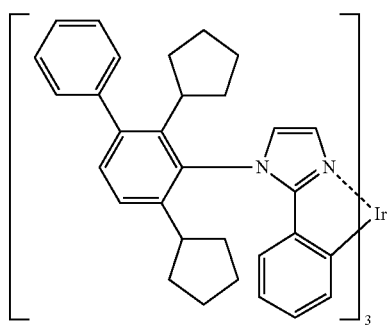
DP-51

-continued
DP-52
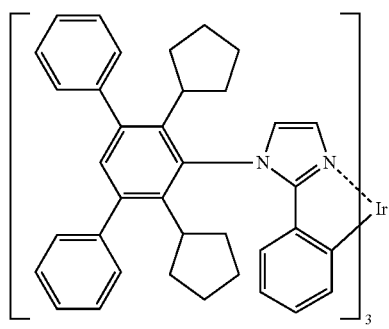
DP-53
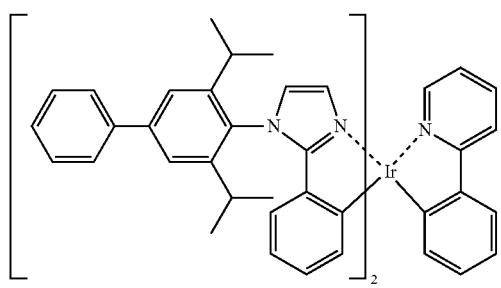
DP-54
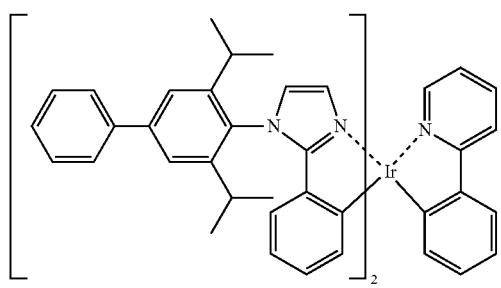
DP-55
DP-56
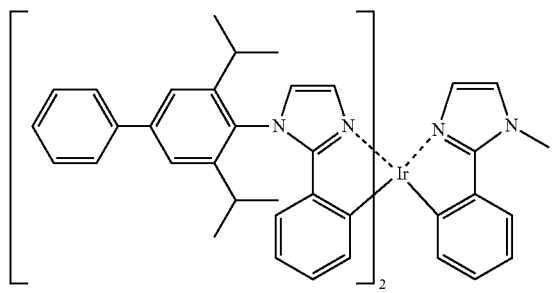
DP-57
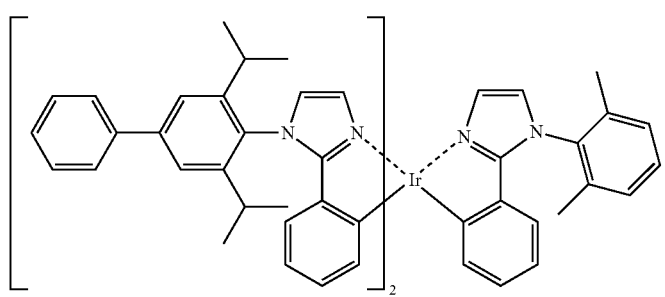
DP-58
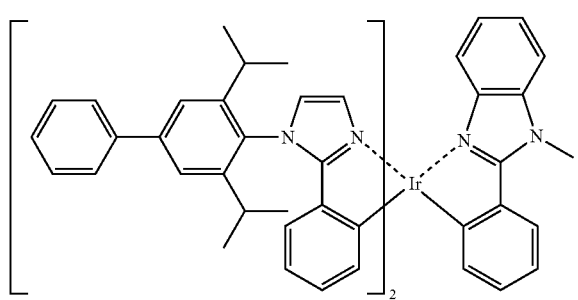

-continued
DP-59
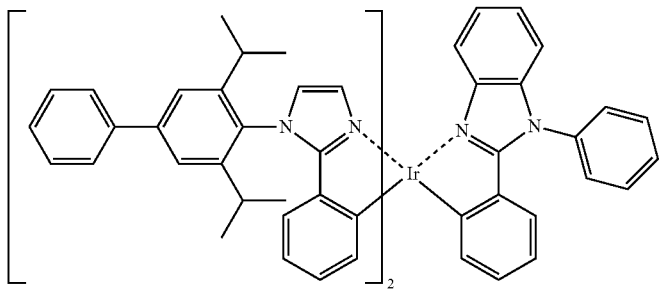
DP-60 DP-61
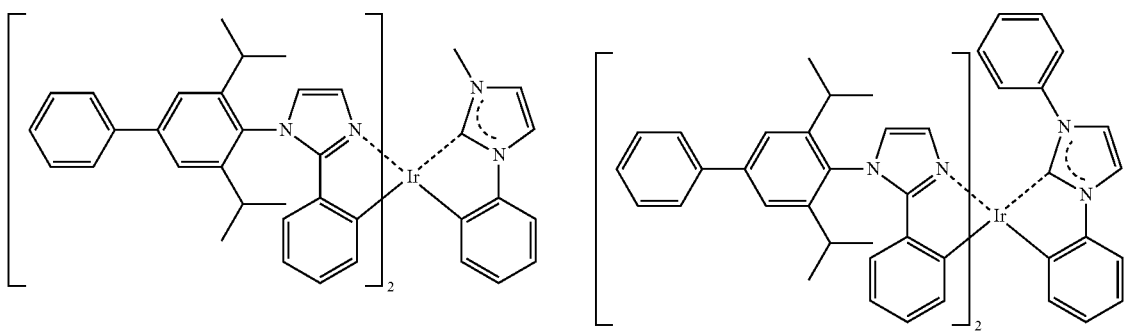
DP-62
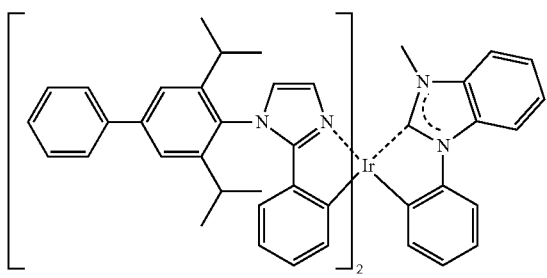
[Chem. 16]
DP-63 DP-64
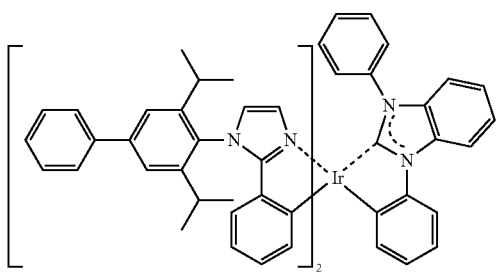

-continued
DP-65
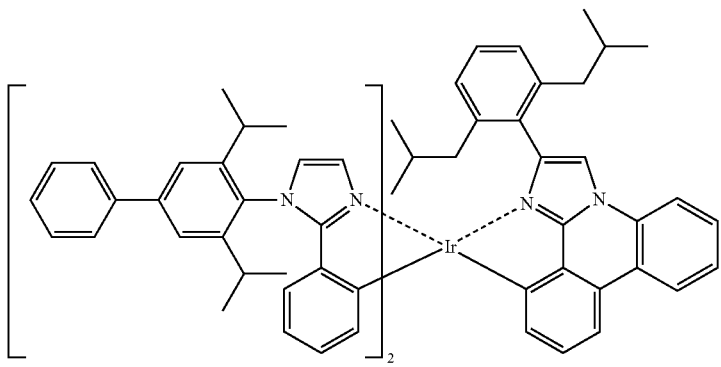
DP-66
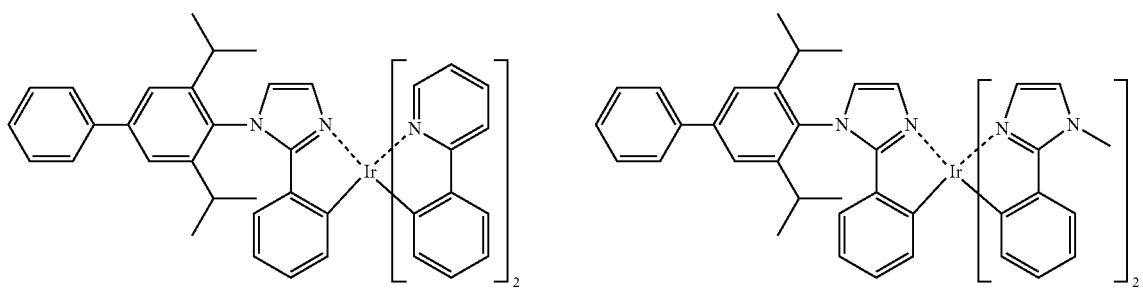
DP-67
[Chem. 17]
DP-68
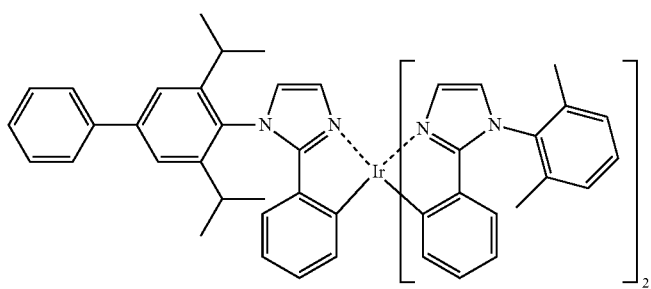
DP-69
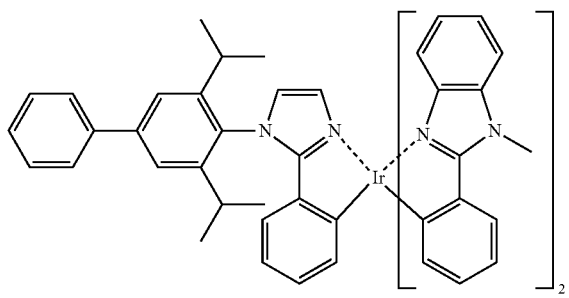
DP-70
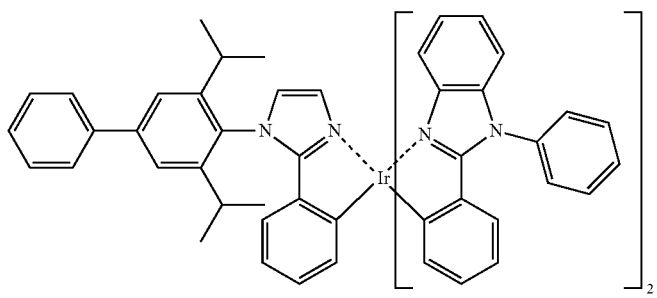

-continued
DP-71
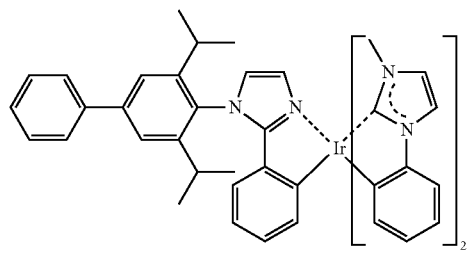
DP-72
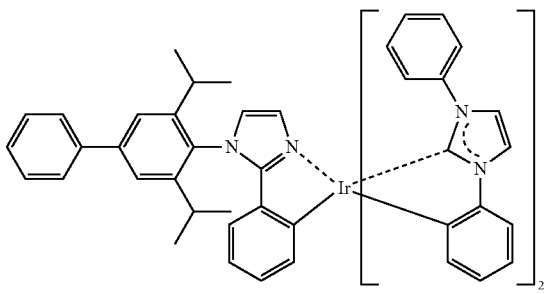
[Chem. 18]
DP-73
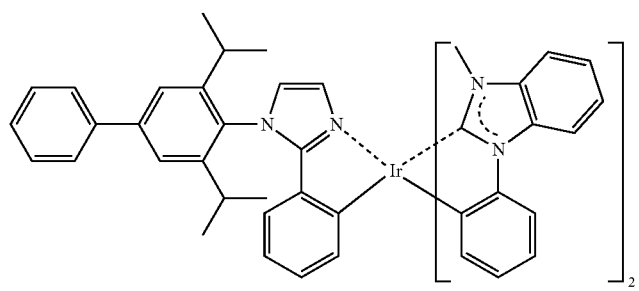
DP-74
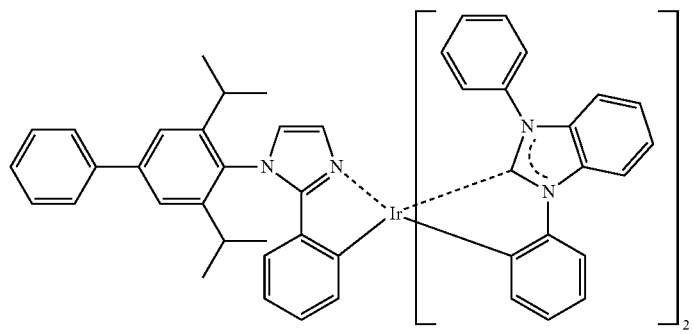
DP-75
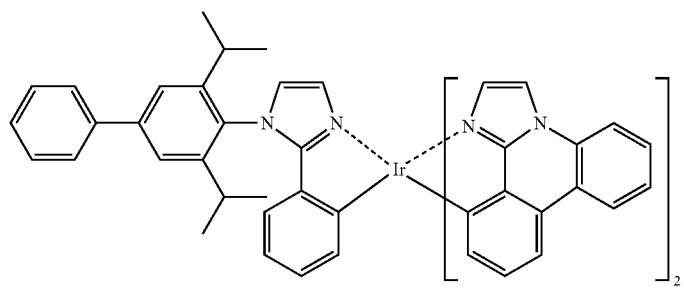

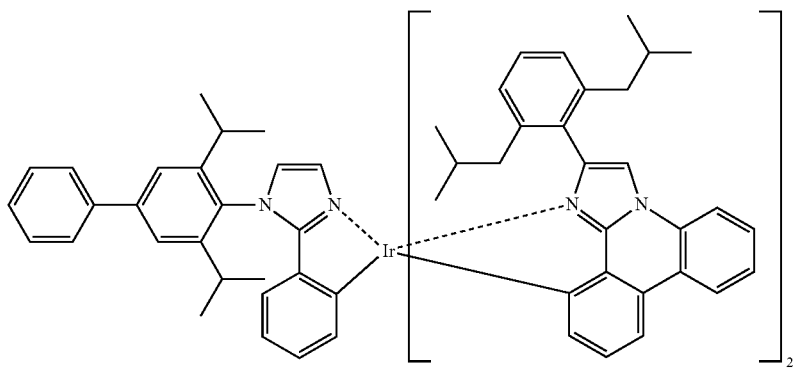

DP-76

(Host Compound Represented by the Formula (4))

In the formula (4), A represents an O or S atom or an $NR_1$ group; and $A_{11}$ to $A_{18}$ each independently represent a N atom or $CR_2$.

In the formula (4), $R_1$ and $R_2$ each independently represent a bonding hand, a hydrogen atom, or a substituent; and if there are a plurality of $CR_2$, they may be the same or different.

Non-limiting examples of the host compound represented by the formula (4) are shown below:

[Chem. 19]

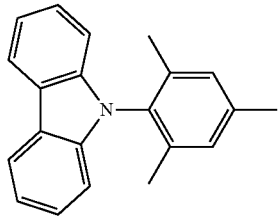

HS-1

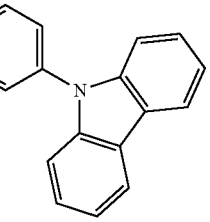

HS-2

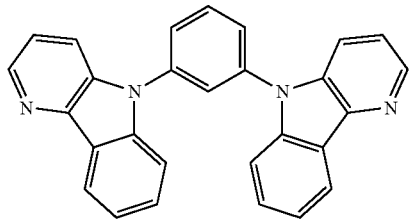

HS-3

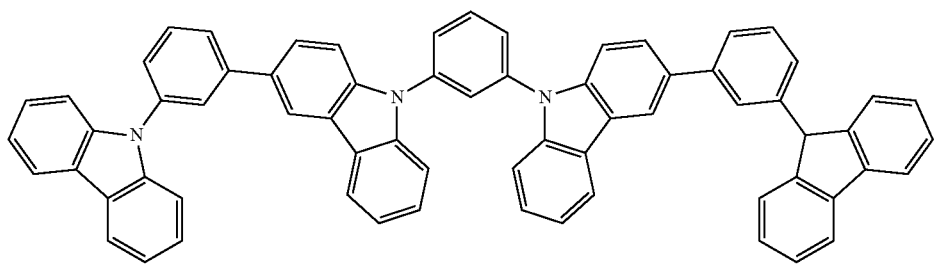

HS-4

-continued
HS-5
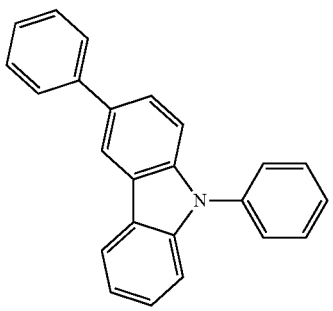
HS-6
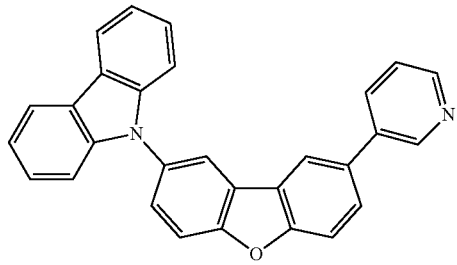
HS-7
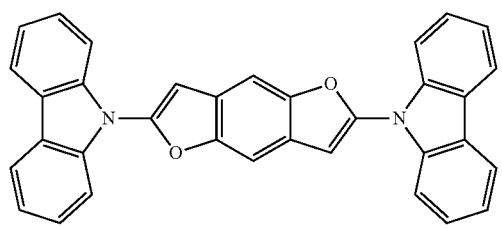
HS-8
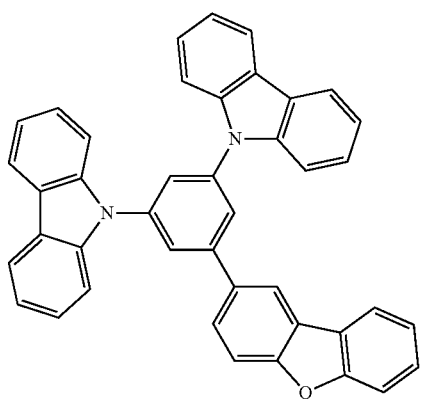
HS-9
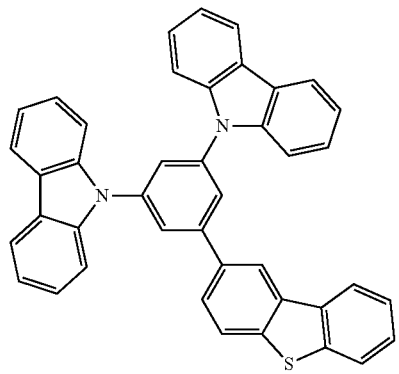
HS-10
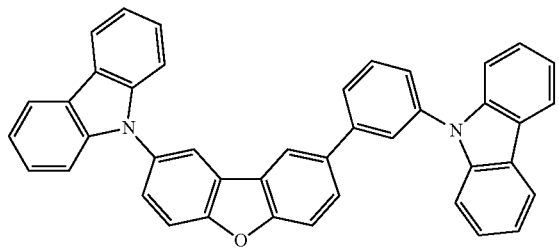
HS-11
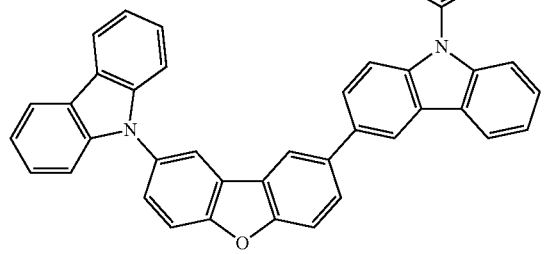
HS-12
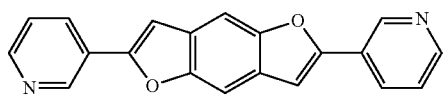

-continued
HS-13
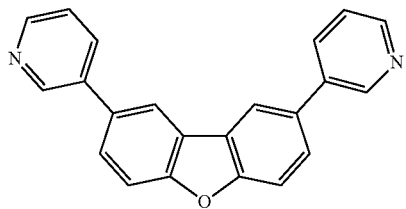
[Chem. 20]
HS-14
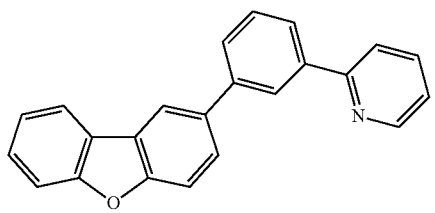
HS-15
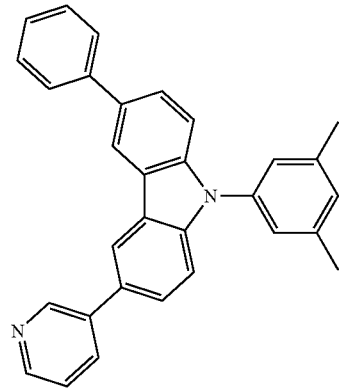
HS-16
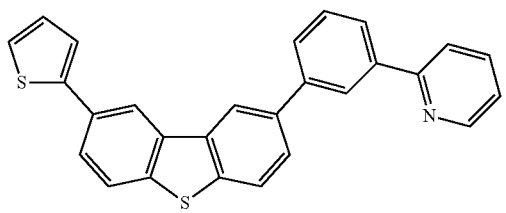
HS-17
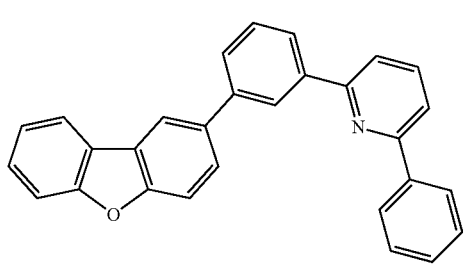
HS-18
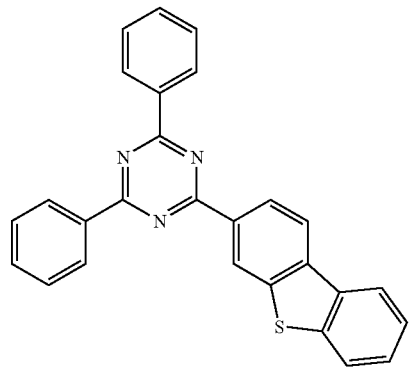
HS-19
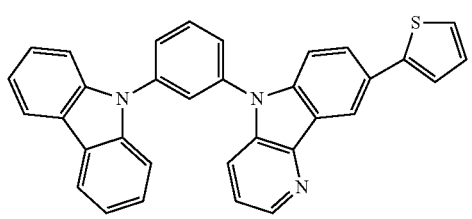
HS-20
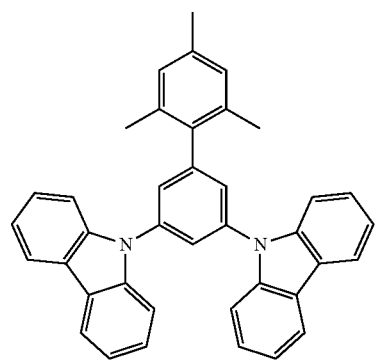

-continued
HS-21
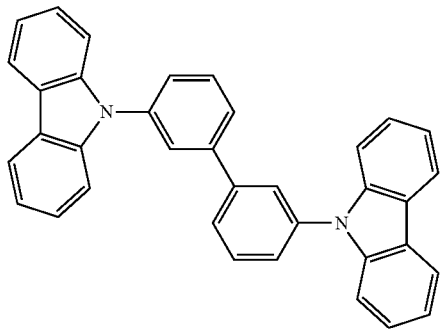
HS-22
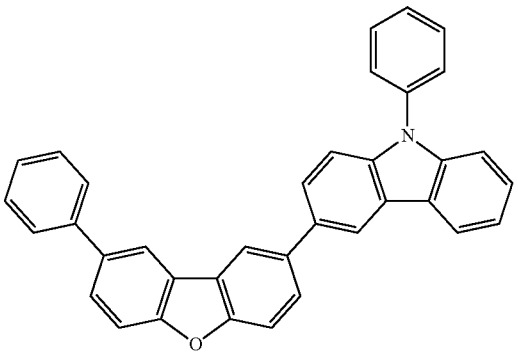
HS-24
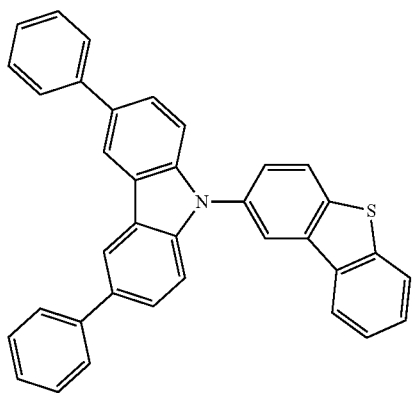
HS-25
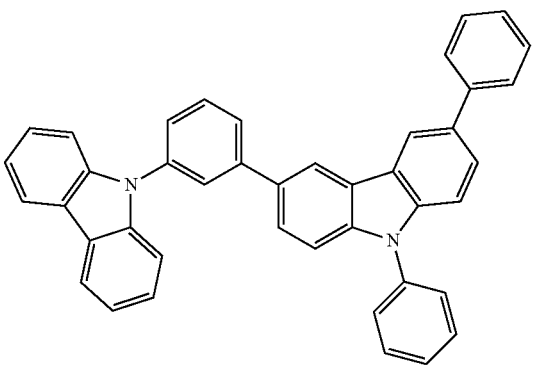
HS-26
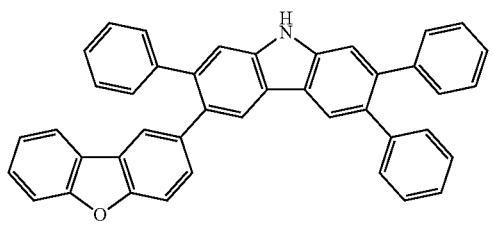
HS-27
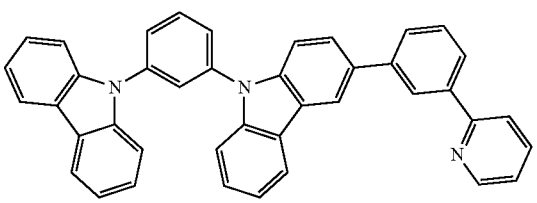
[Chem. 21]
HS-28
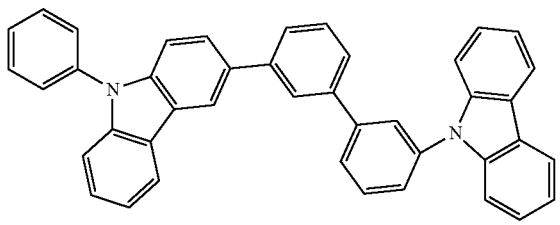

-continued
HS-29
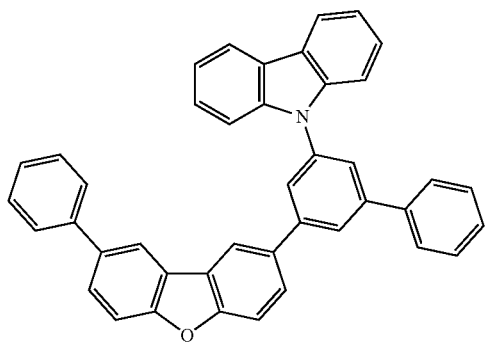
HS-30
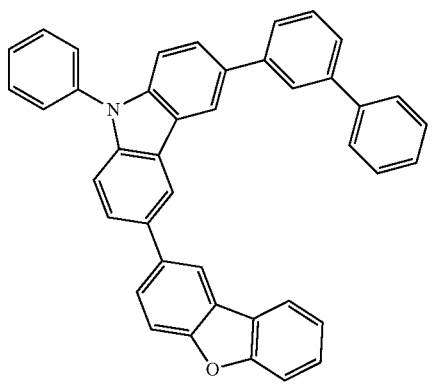
HS-31
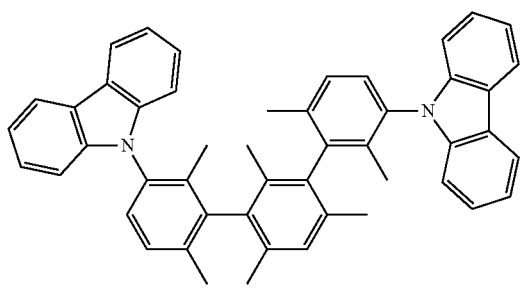
HS-32
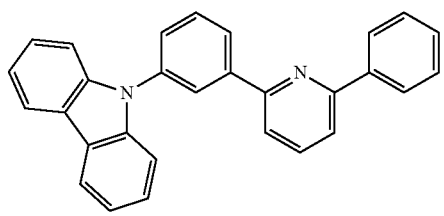
HS-33
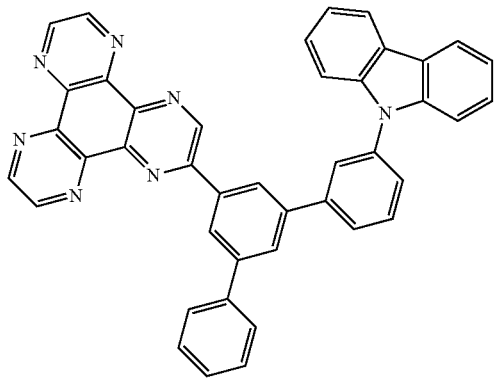
HS-34
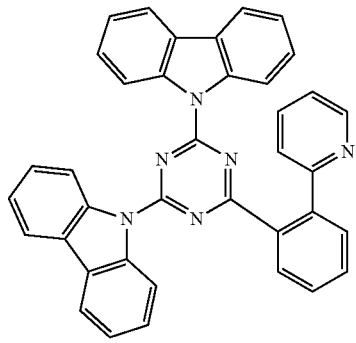
HS-35
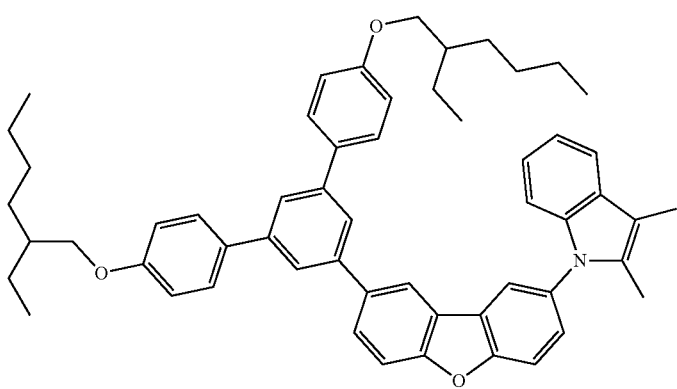

-continued
HS-36
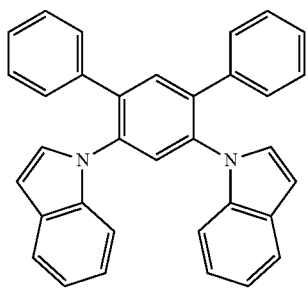
HS-37
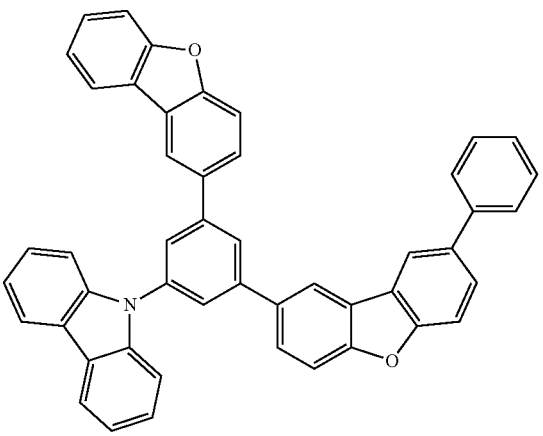
HS-38
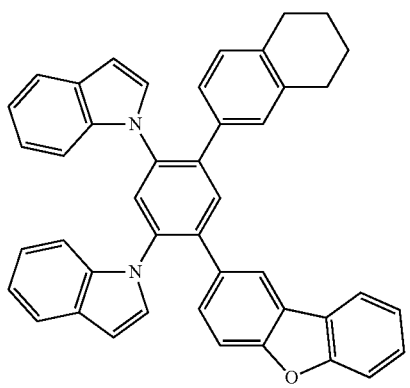
HS-39
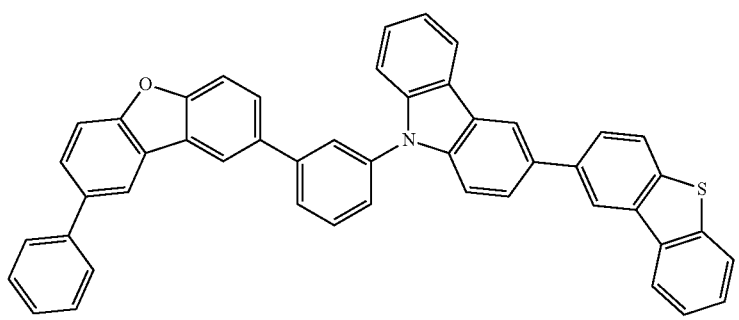
[Chem. 22]
HS-40
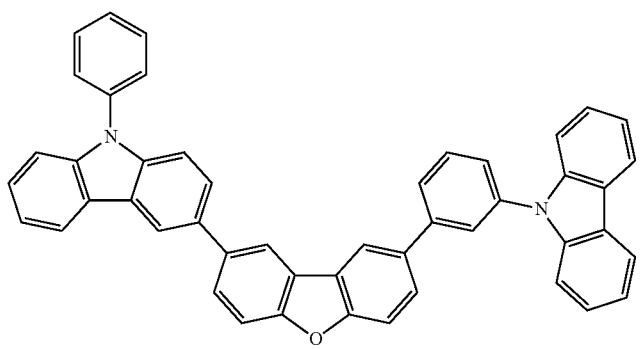

-continued
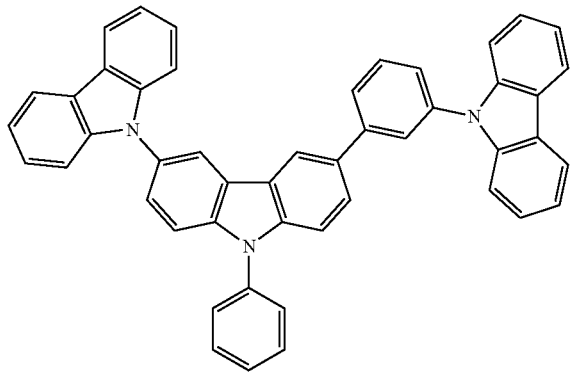
HS-41
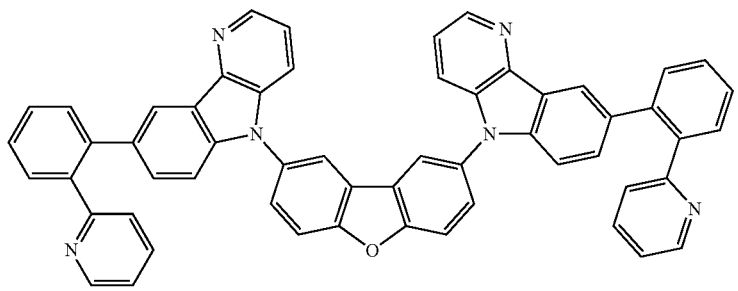
HS-42
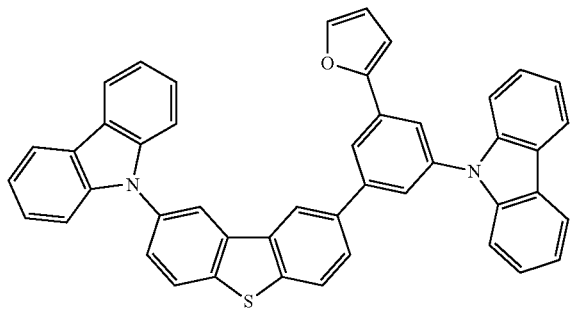
HS-43
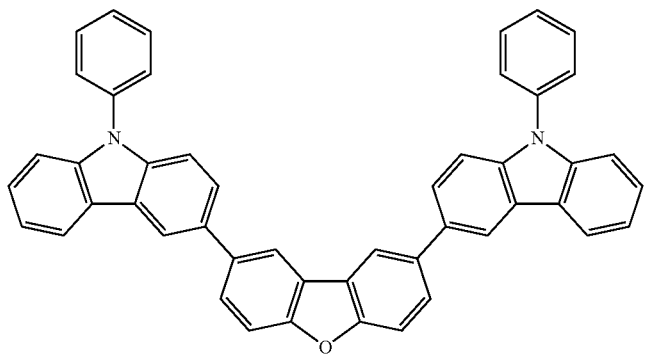
HS-44

-continued
HS-45
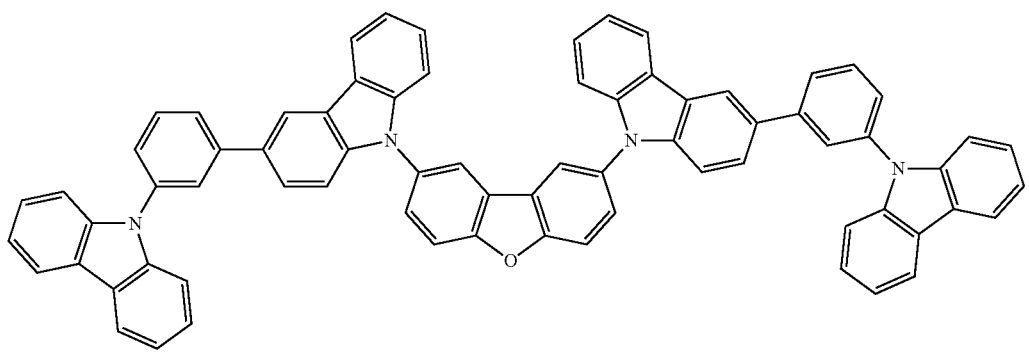
HS-46
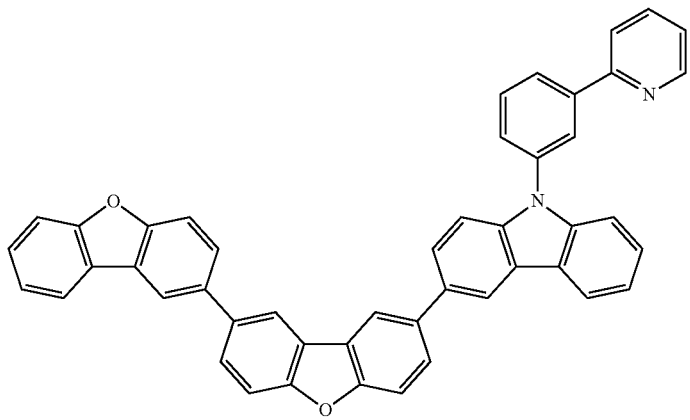
HS-47
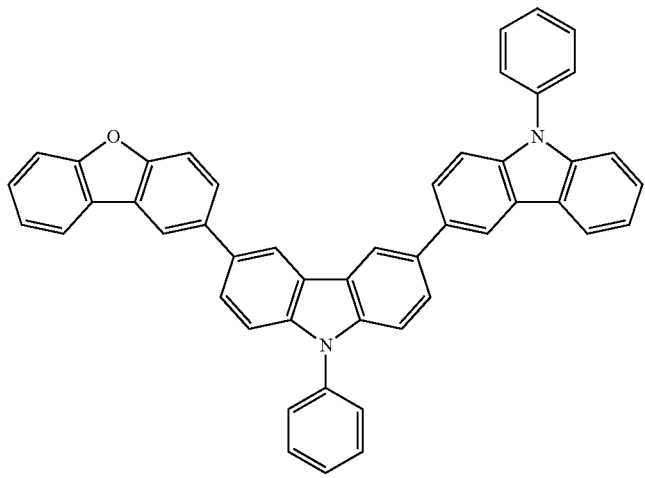
HS-48
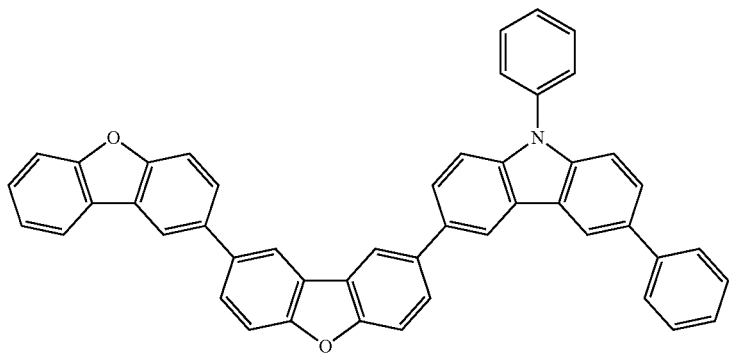

[Chem. 23]
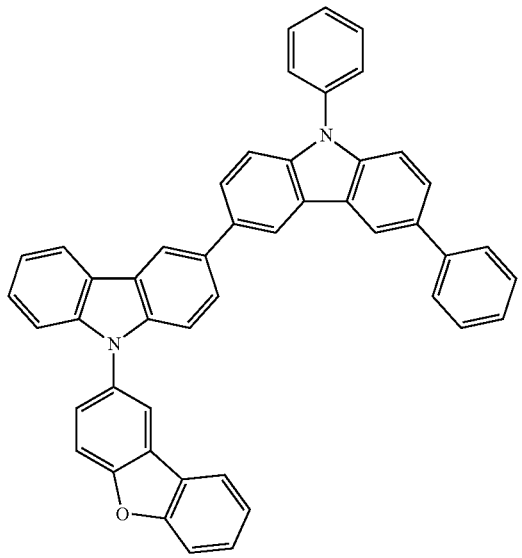
HS-49
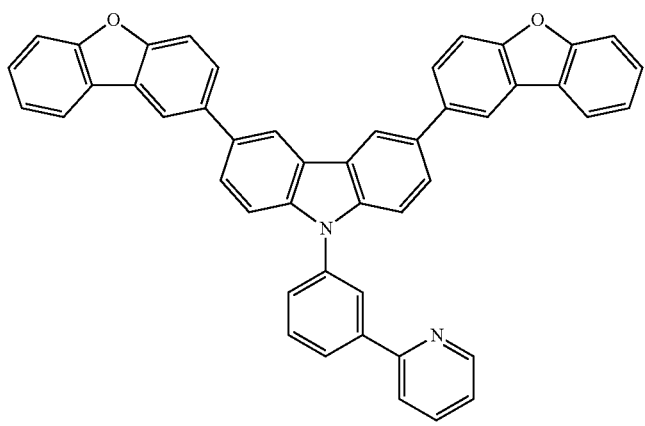
HS-50
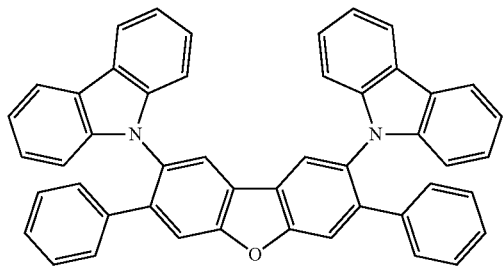
HS-51

-continued
HS-52
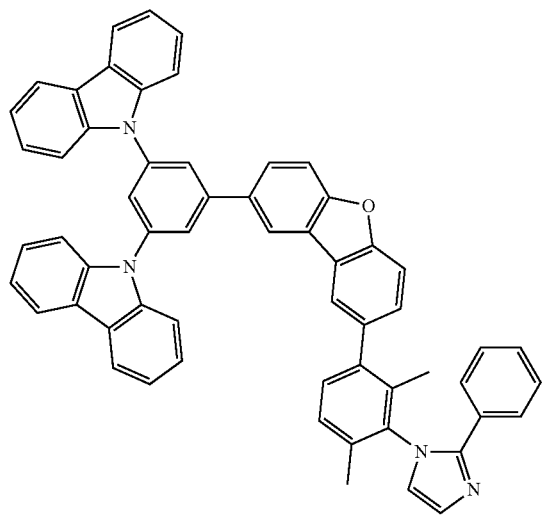
HS-53
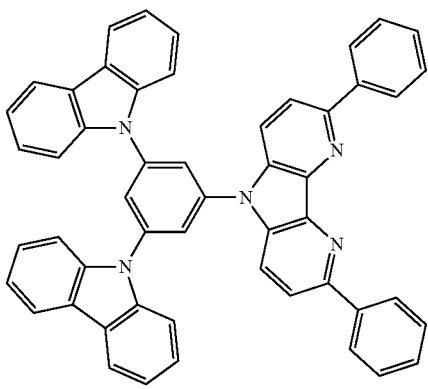
HS-54
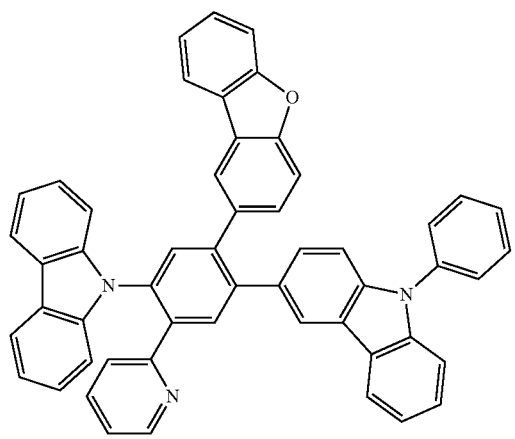
HS-55
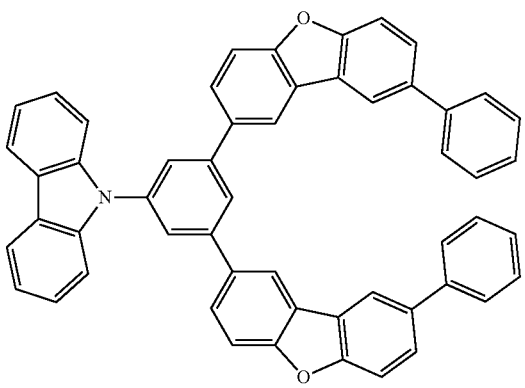
HS-56
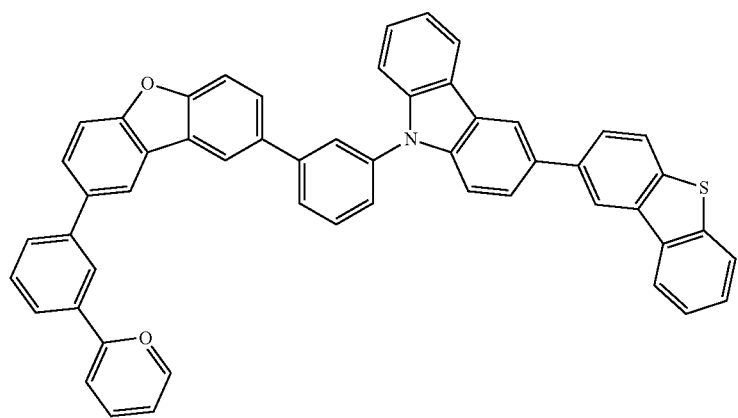

-continued
HS-57
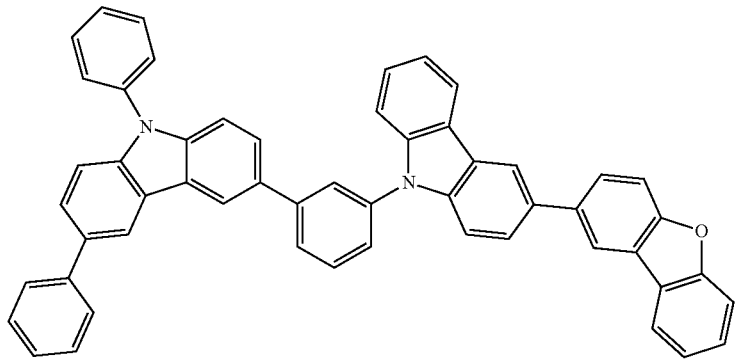
HS-58
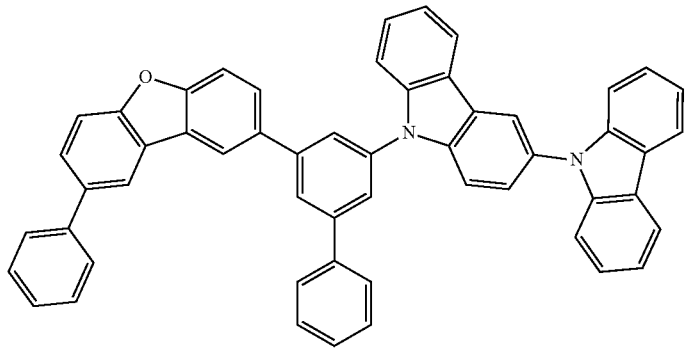
HS-59
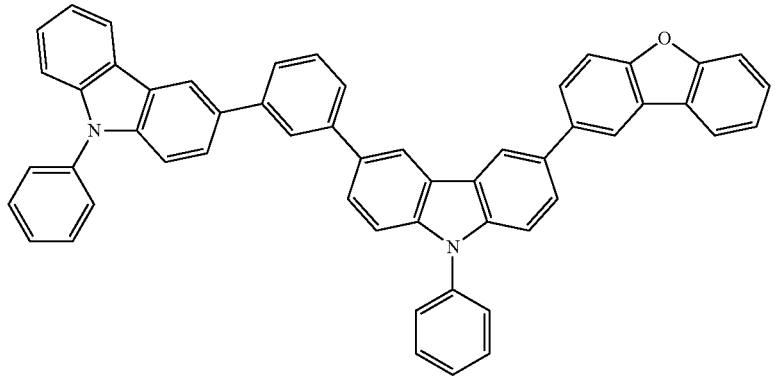
[Chem. 24]
HS-60
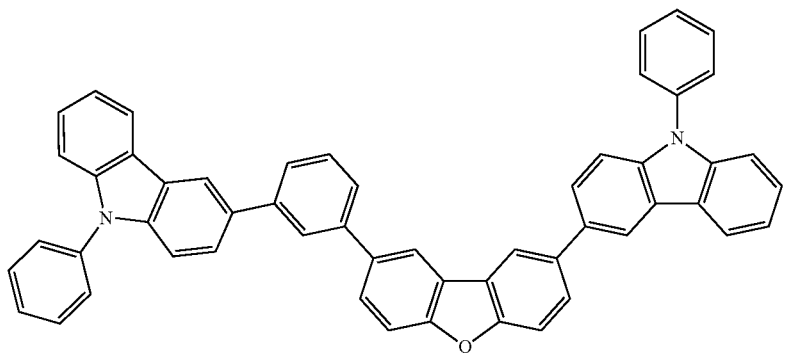

-continued
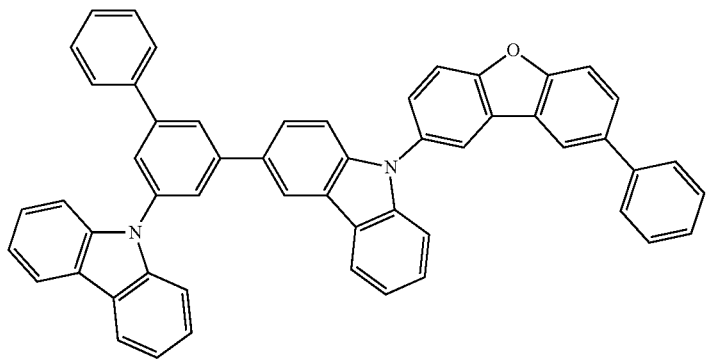
HS-61
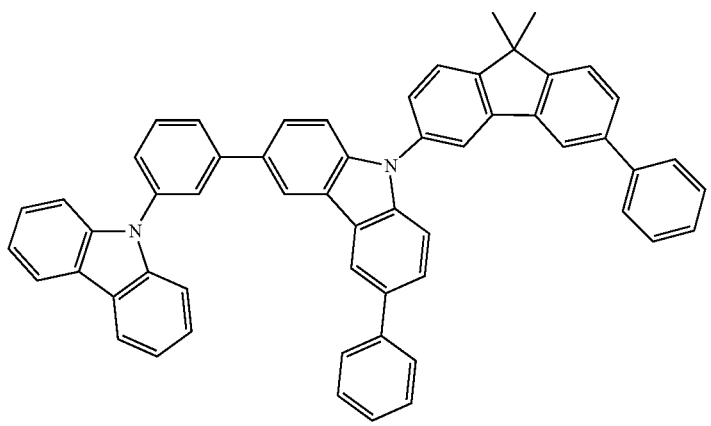
HS-62
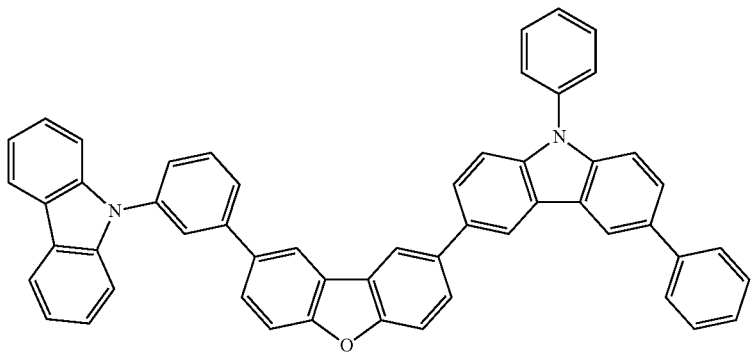
HS-63
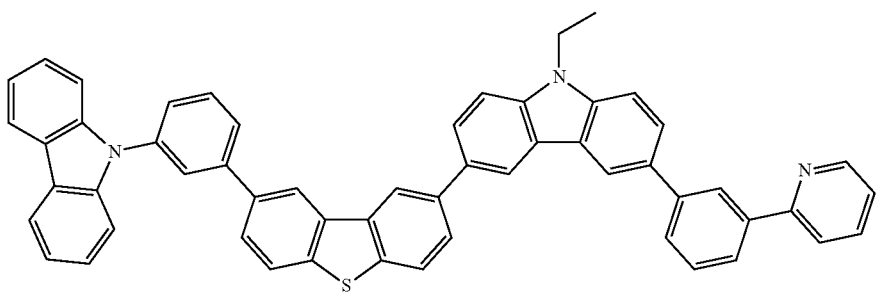
HS-64

-continued
HS-65
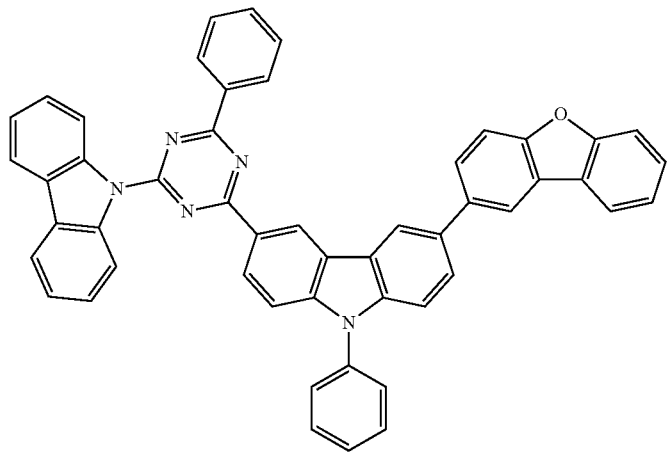
HS-66
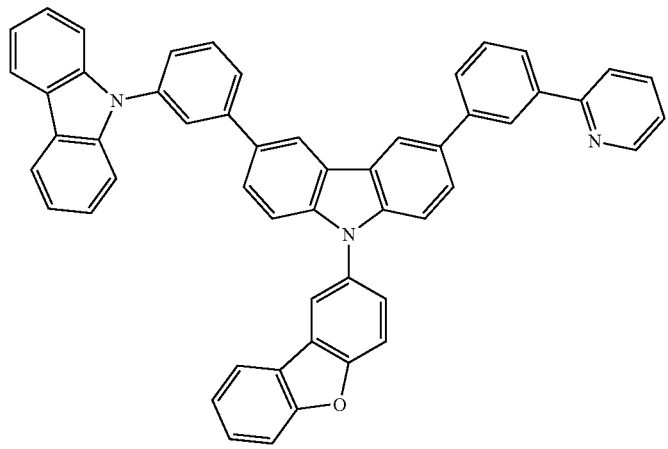
HS-67
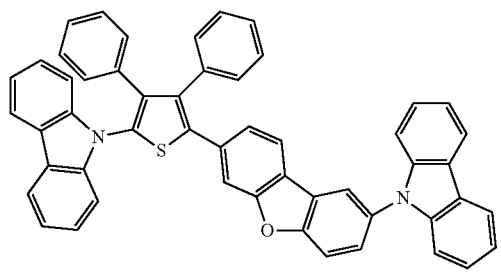
HS-68
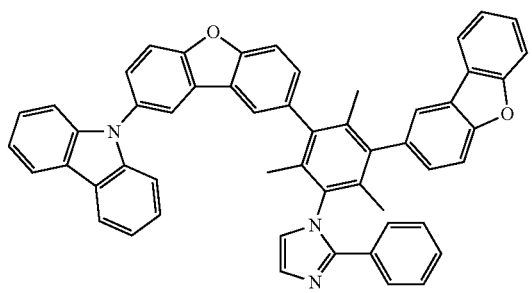
[Chem. 25]
HS-69
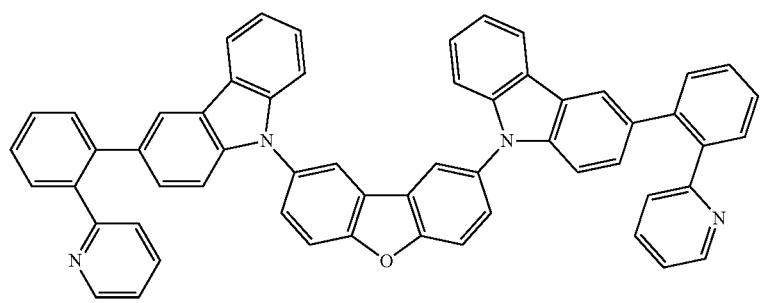

HS-70
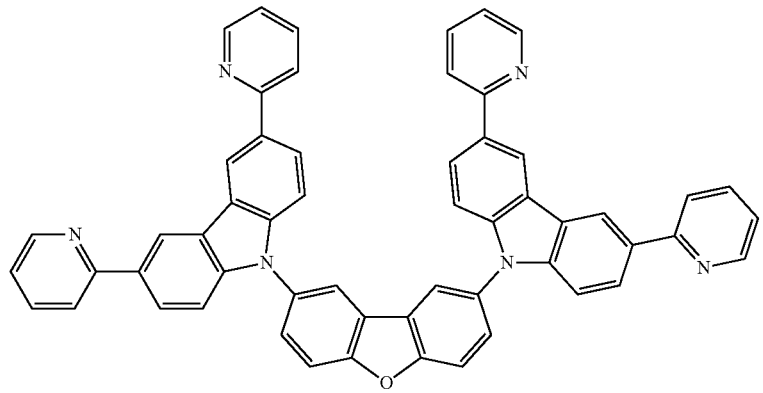
HS-71
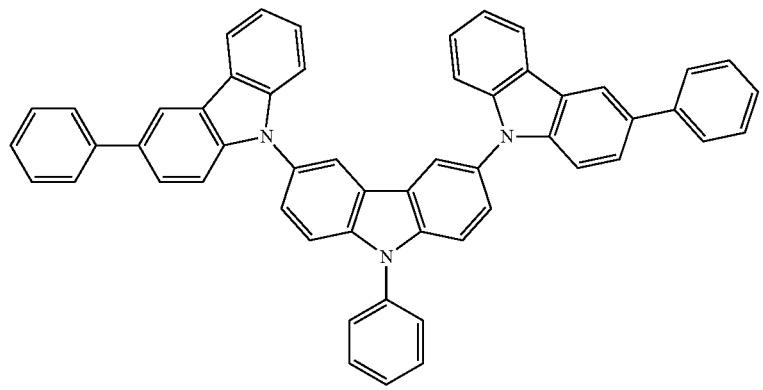
HS-72
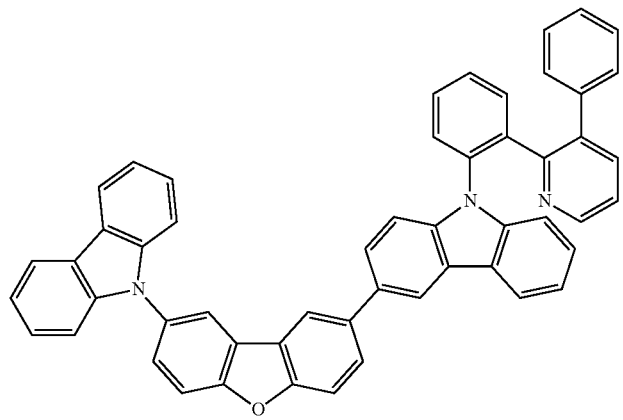
HS-73
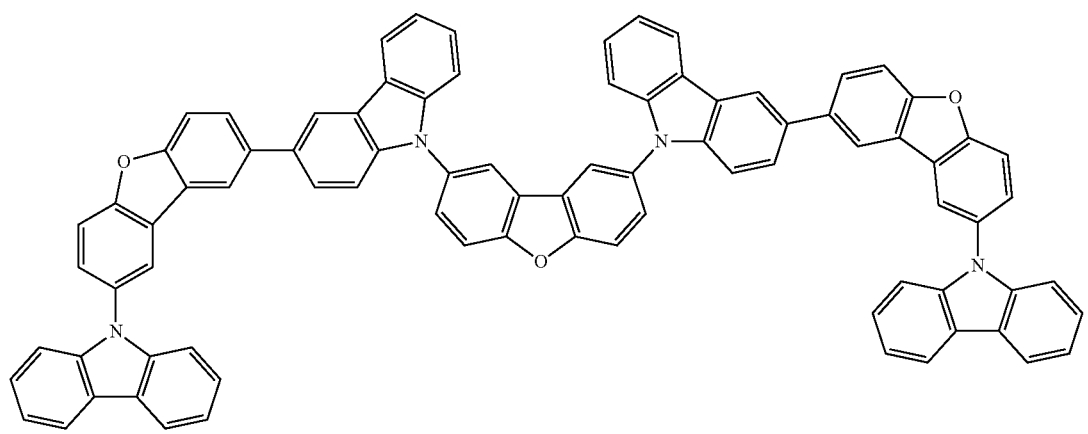

-continued
HS-74
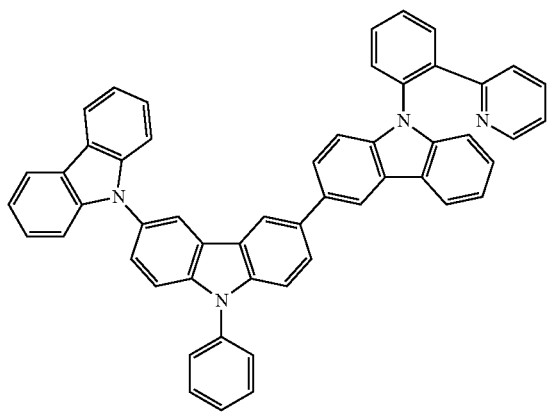
HS-75
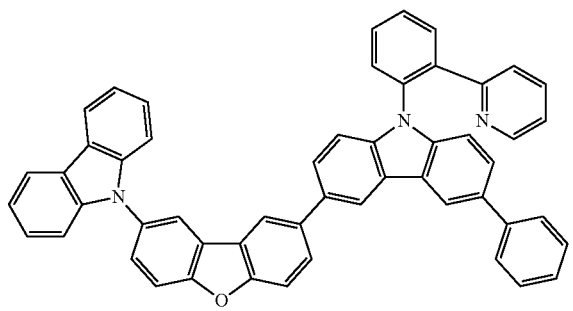
HS-76
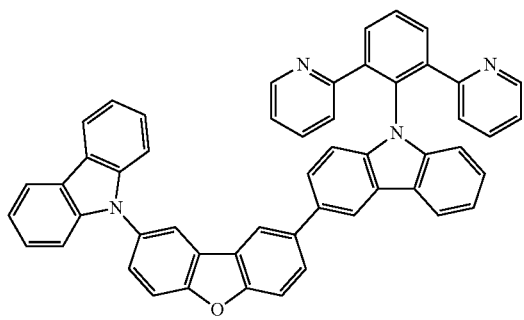
HS-77
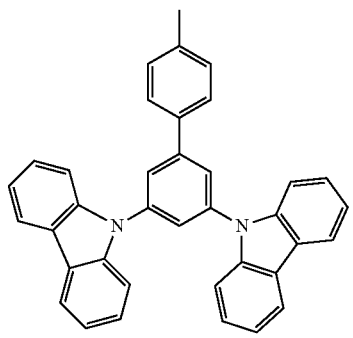
HS-78
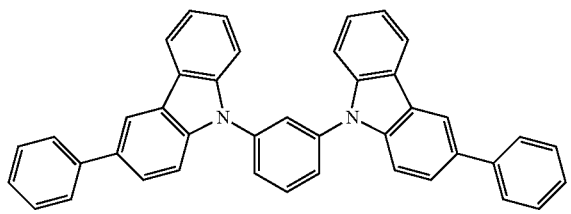
[Chem. 26]
HS-79
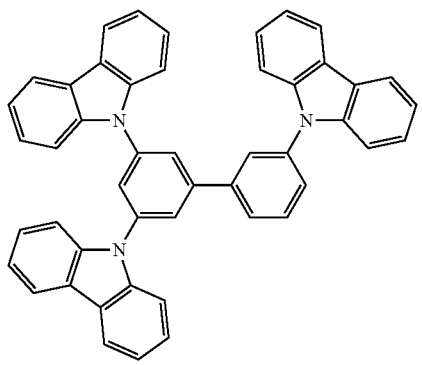
HS-80
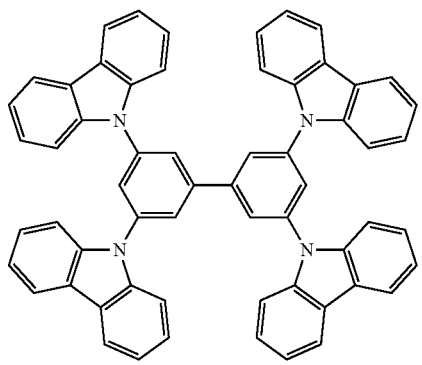

-continued
HS-81
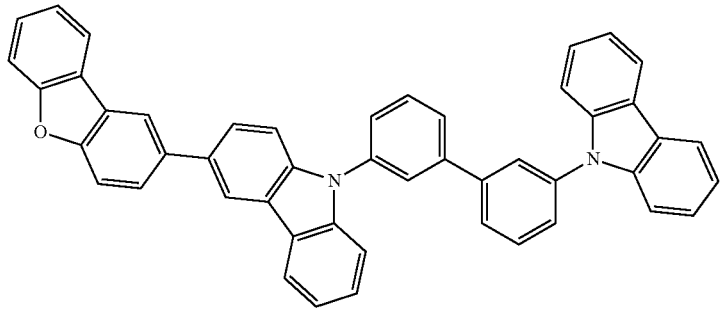
HS-82
HS-83
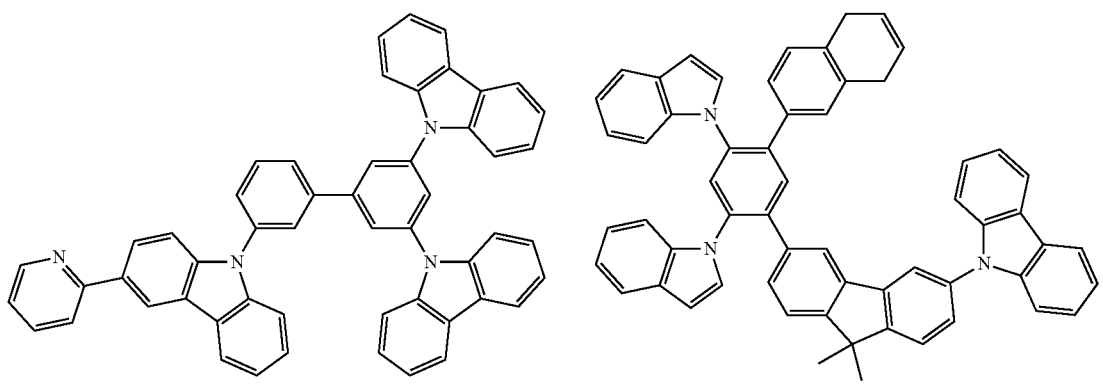
HS-84
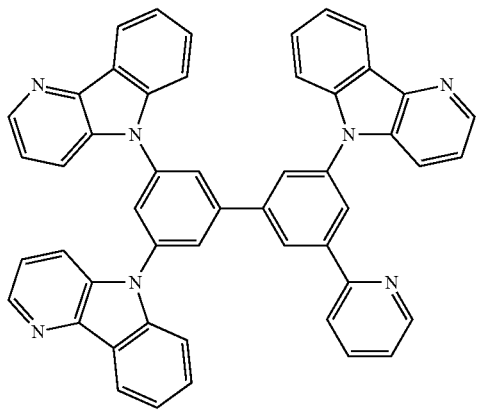
HS-85
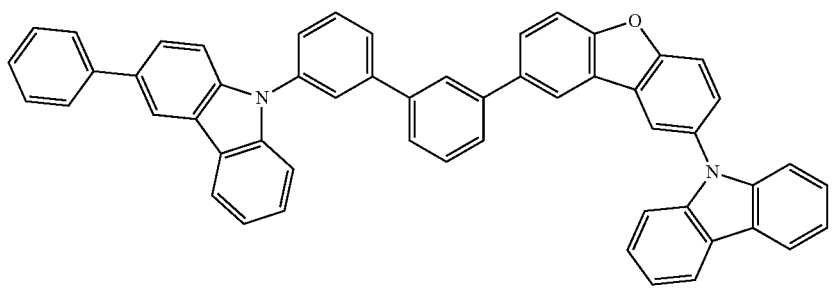

-continued
HS-86
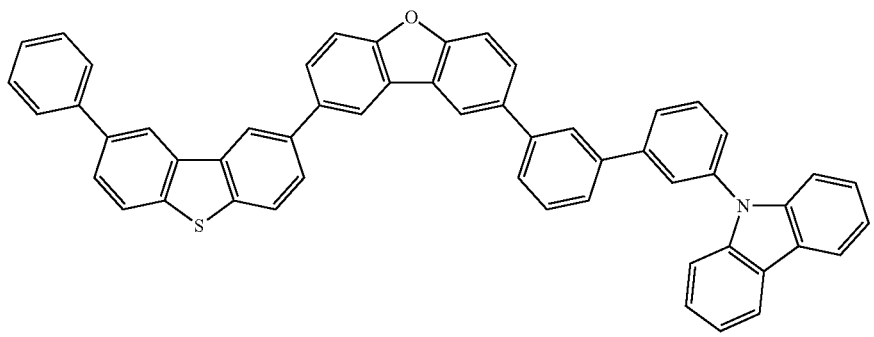
HS-87
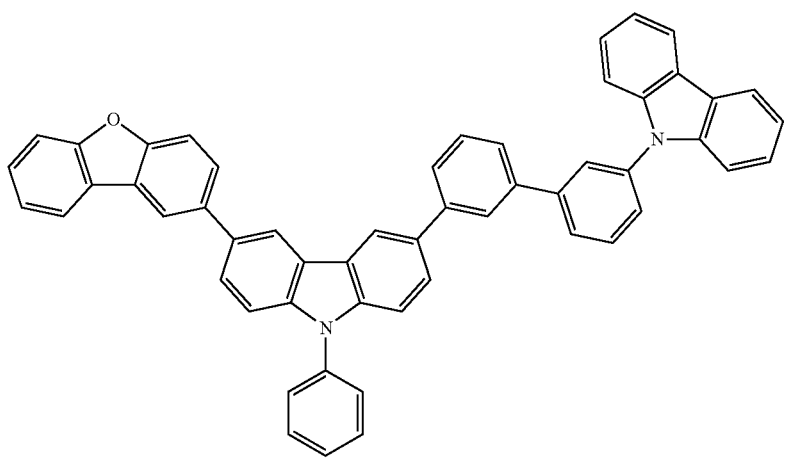
[Chem. 27]
HS-88
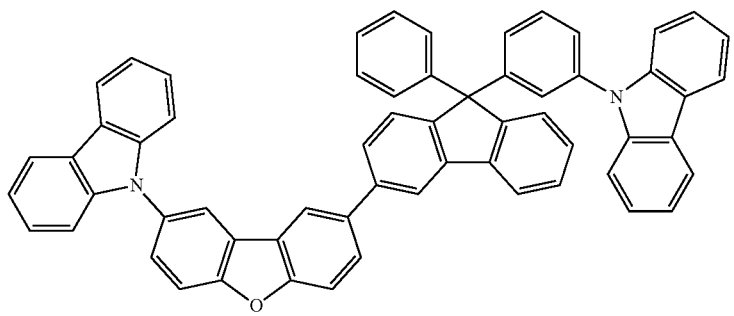
HS-89
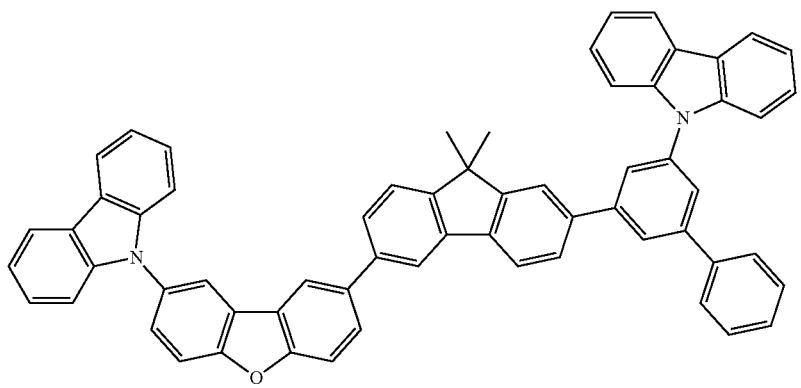

-continued
HS-90
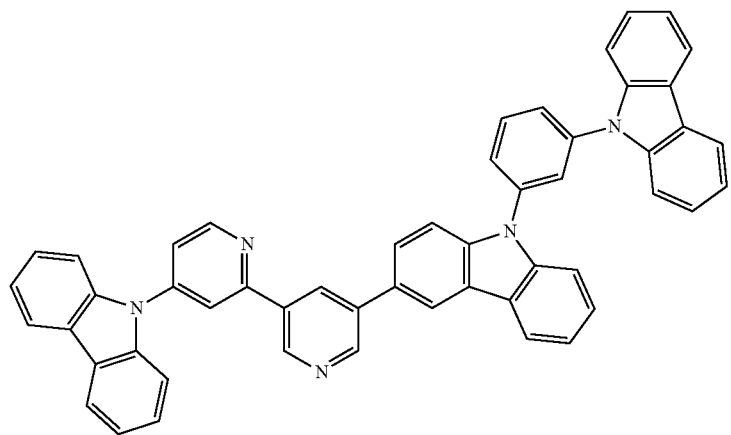
HS-91
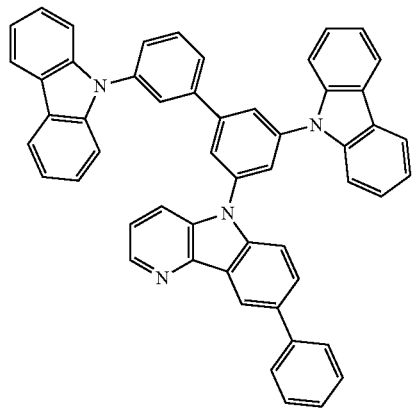
HS-92
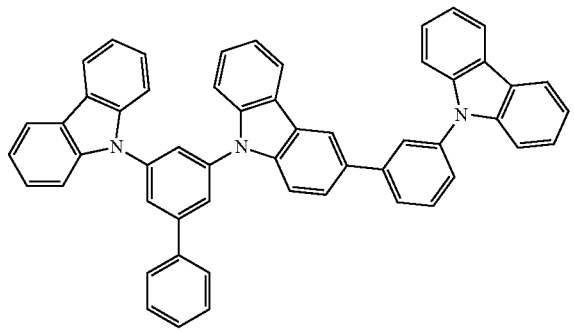
HS-93
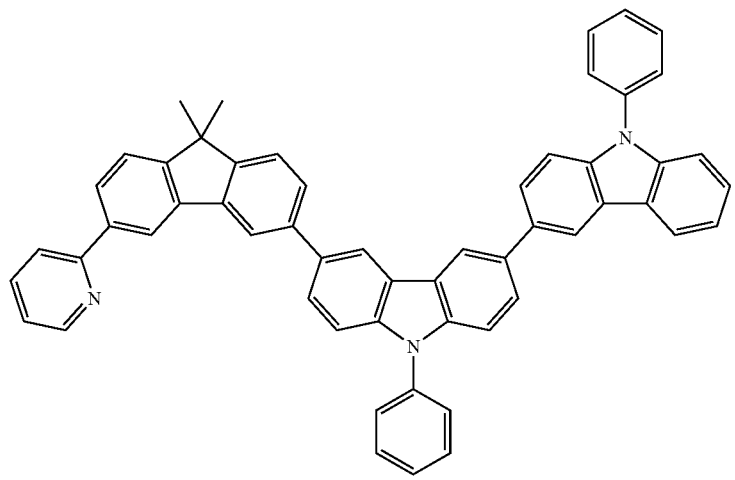

-continued
HS-94
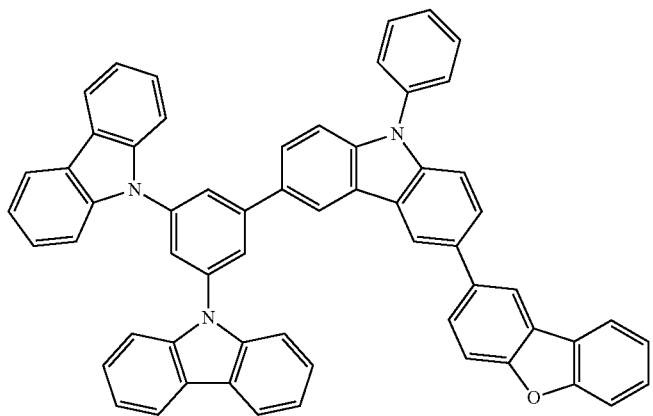
HS-95
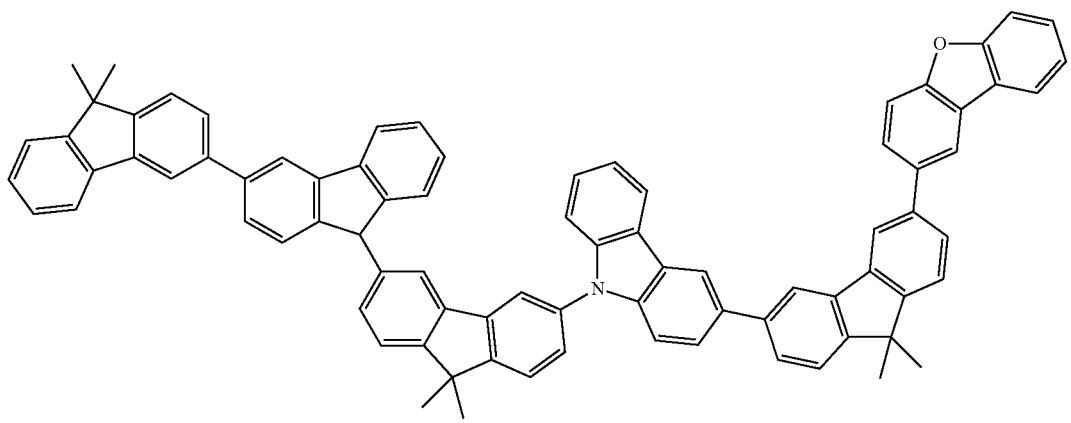
HS-96
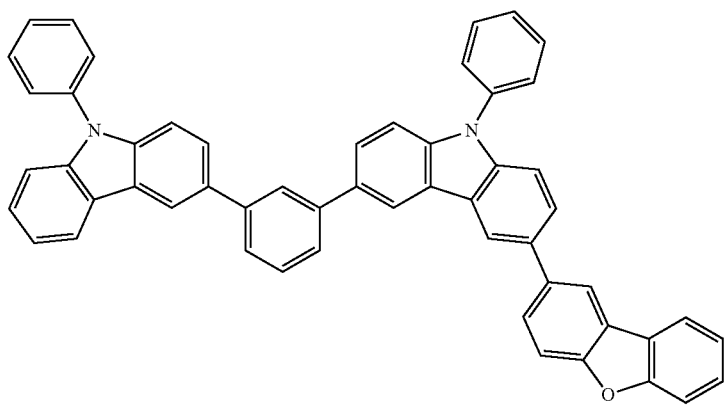

[Chem. 28]
HS-97
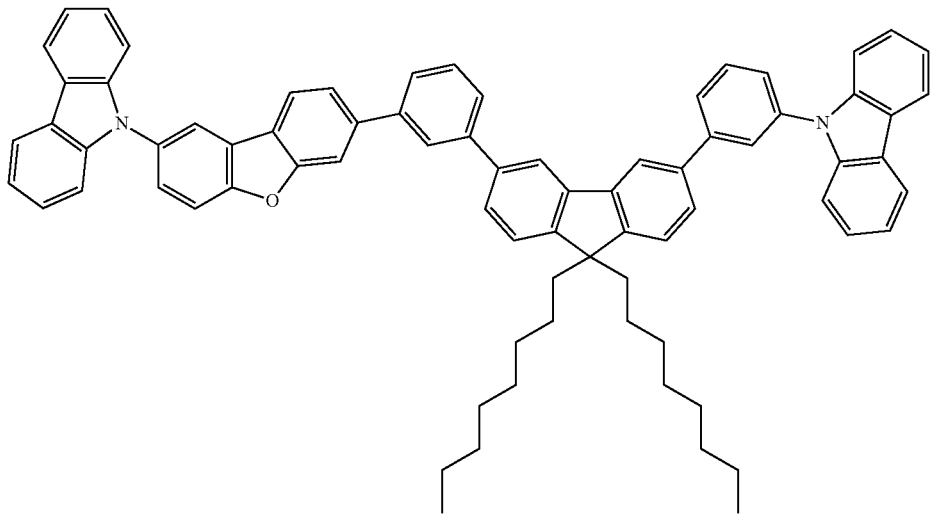
HS-98
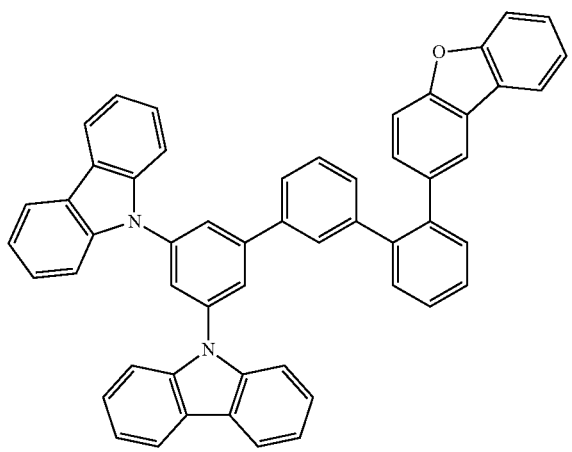
HS-99
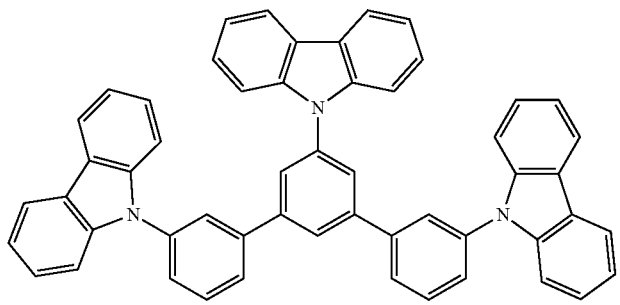

HS-100
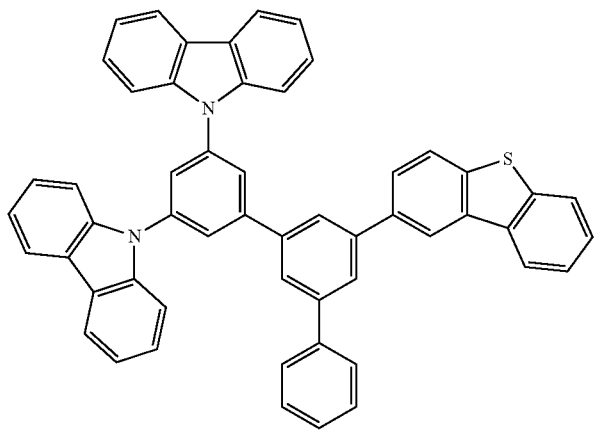
HS-101
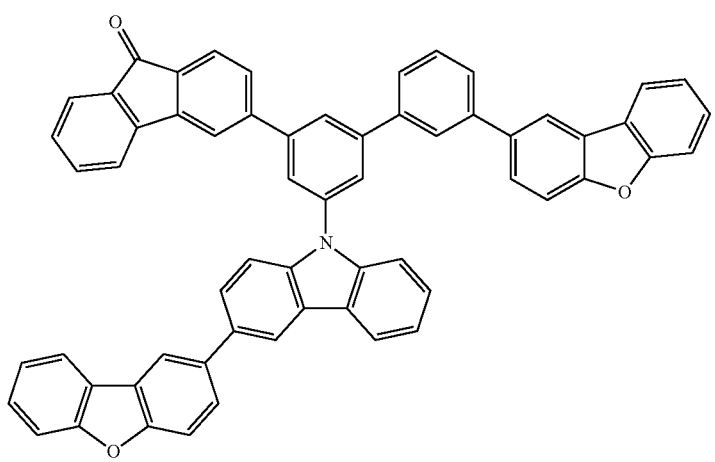
[Chem. 29]
Host-1
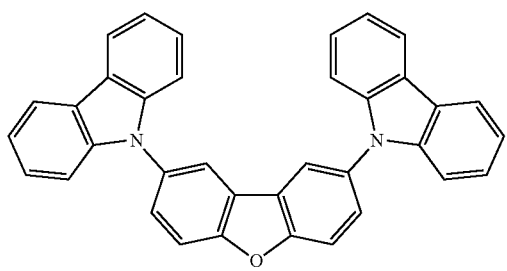
Host-2
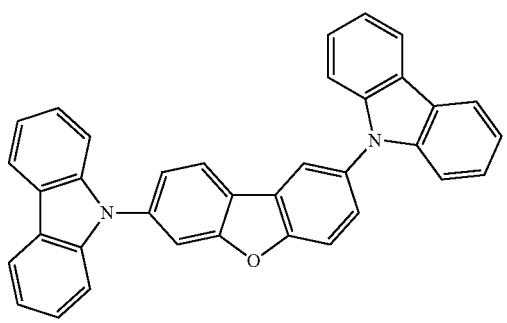

-continued
Host-3
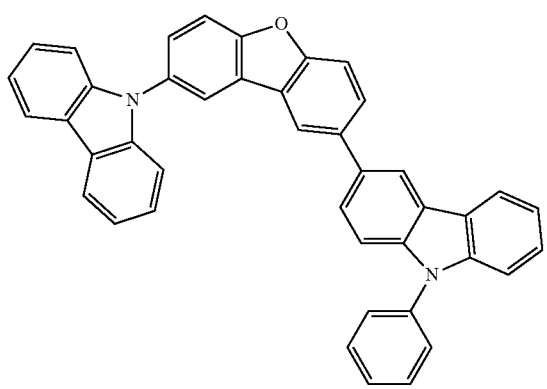
Host-4
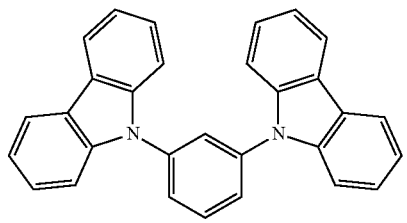
Host-5
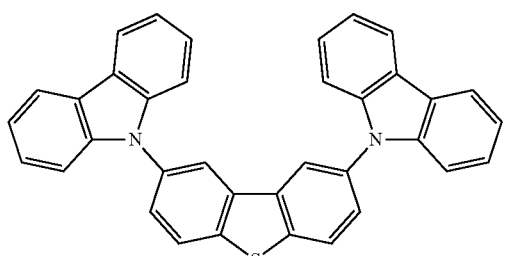
Host-6
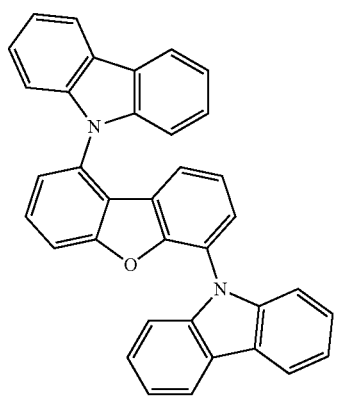
Host-7
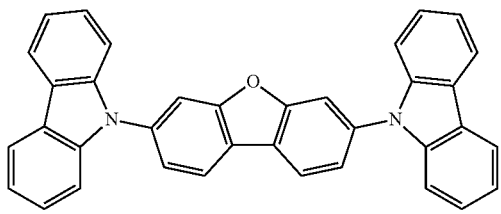
Host-8
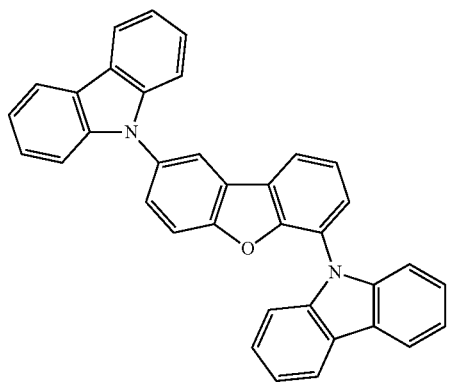
Host-9
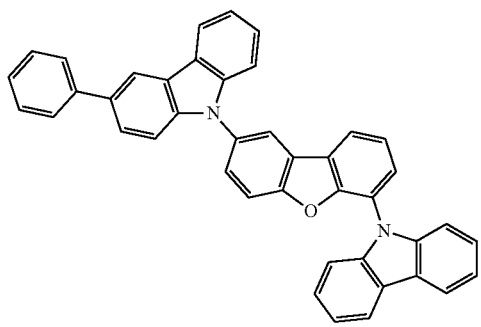
Host-10
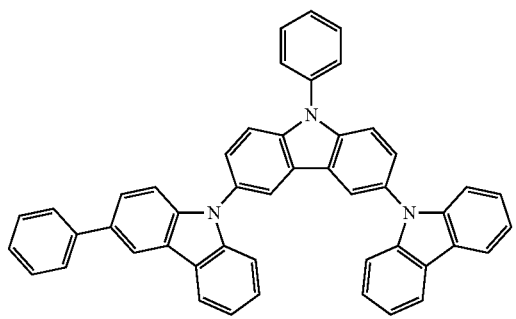

Host-11

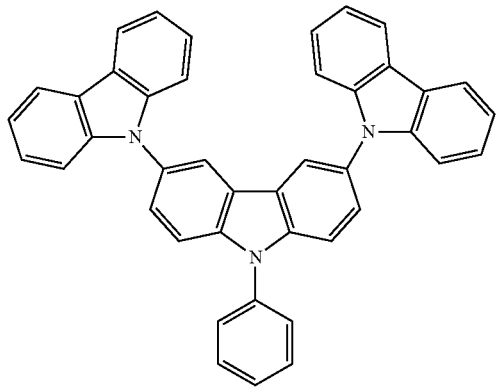

Host-12

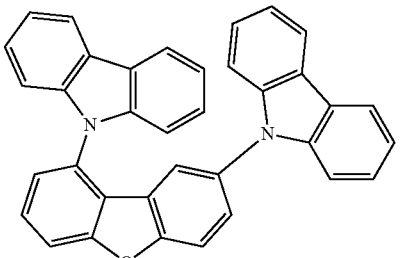

Host-13

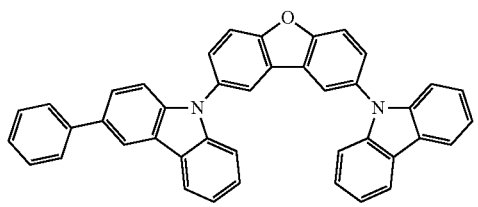

Host-14

(Structural Layers of Organic EL Element)

The structural layers of the organic EL element of the present invention will now be described. Non-limiting examples of the preferred layer structure of the organic EL element in the present invention are shown below:

(i) anode/light-emitting layer/electron-transporting layer/cathode;

(ii) anode/hole-transporting layer/light-emitting layer/electron-transporting layer/cathode;

(iii) anode/hole-transporting layer/light-emitting layer/hole-blocking layer/electron-transporting layer/cathode;

(iv) anode/hole-transporting layer/light-emitting layer/hole-blocking layer/electron-transporting layer/cathode buffer layer/cathode;

(v) anode/anode buffer layer hole-transporting layer/light-emitting layer/hole-blocking layer/electron-transporting layer/cathode buffer layer/cathode;

(vi) anode/hole-transporting layer/anode buffer layer/light-emitting layer/hole-blocking layer/electron-transporting layer/cathode buffer layer/cathode; and (vii) anode/anode buffer layer/hole-transporting layer/light-emitting layer/electron-transporting layer/cathode buffer layer/cathode.

In the case of an organic EL element including a plurality of light-emitting layers, a nonluminescent intermediate layer may be disposed between any two light-emitting layers. Among the layer structures mentioned above, organic layers including the light-emitting layer (other than the anode and cathode) are collectively defined as a light-emitting unit; and a plurality of light-emitting units may be stacked. The stacked light-emitting units may include a nonluminescent intermediate layer between any two light-emitting units. The intermediate layer may further include a charge-generating layer.

The organic EL element of the present invention is preferably a white light-emitting layer. The lighting device preferably includes the element.

Each layer of the organic EL element of the present invention will be described.

(Light-Emitting Layer)

The light-emitting layer according to the present invention emits light by recombination of electrons and holes injected from electrodes or an electron-transporting layer and a hole-transporting layer. The light emission site may be inside the light-emitting layer or may be the interface between the light-emitting layer and an adjoining layer thereof.

The light-emitting layer may have any total thickness, which is preferably controlled within a range of 2 nm to 5 μm, more preferably 2 to 200 nm, and most preferably 5 to 100 nm, from the viewpoints of homogeneity of the film, a decrease in voltage applied during luminescence, and an improvement in stability of emission color regardless of a variable driving current.

The light-emitting layer can be produced by forming a thin film from a luminescent dopant or a host compound described below by, for example, vacuum deposition or a wet method (also referred to as wet process) such as spin coating, casting, die coating, blade coating, roll coating, ink jetting, printing, spray coating, curtain coating, or Langmuir Blodgett method (LB deposition).

The light-emitting layer of the organic EL element of the present invention contains a luminescent dopant (e.g., a phosphorescent light-emitting dopant compound (also referred to as phosphorescent dopant or phosphorescent light-emitting dopant group) or a fluorescent dopant) and a host compound. In the present invention, the host compound and the phosphorescent light-emitting organic metal complex as the phosphorescent light-emitting dopant have a difference of 0 to −0.5 debye in relative dielectric constant and have a difference of 0 to −5.5 debye in dipole moment. The difference in dipole moment is more preferably 0 to 4 debye.

Specifically, at least one phosphorescent light-emitting organic metal complex is represented by the formula (2)

(i.e., phosphorescent light-emitting organic metal complex having a metal atom coordinated with a ligand represented by the formula (1)), and the host compound is represented by the formula (4).

(Luminescent Dopant Compound)

The luminescent dopant compound (also referred to as luminescent dopant) according to the present invention will be described.

The luminescent dopant may be a fluorescent dopant (also referred to as fluorescent compound) or a phosphorescent dopant (also referred to as phosphorescent light-emitting dopant compound, phosphorescent material, phosphorescent compound, or phosphorescent light-emitting compound).

(Phosphorescent Dopant (Also Referred to as Phosphorescent Light-Emitting Dopant Compound))

A phosphorescent dopant according to the present invention will be described.

The phosphorescent dopant according to the present invention is a compound that emits light from the excited triplet, specifically, a compound that emits phosphorescence at room temperature (25° C.) and is defined as a compound having a phosphorescence quantum yield of 0.01 or more at 25° C. The phosphorescence quantum yield is preferably 0.1 or more.

The phosphorescence quantum yield can be measured by the method described in page 398 of Bunkoh II of Dai 4 Han Jikken Kagaku Koza 7 (Spectroscopy II of Experimental Chemistry 7, $4^{th}$ edition) (1992, published by Maruzen Co., Ltd.). The phosphorescence quantum yield in a solution can be measured using appropriate solvents. The only requirement for the phosphorescent dopant according to the present invention is to achieve the above-mentioned phosphorescence quantum yield (0.01 or more) in any one of solvents.

There are two principles for emission by a phosphorescent dopant. One is an energy transfer-type, in which the recombination of carriers occurs on a host compound onto which the carriers are transferred to produce an excited state of the luminescent host compound, and then emission occurs from the phosphorescent dopant via transfer of this energy to a phosphorescent dopant. The other is a carrier trap-type, in which a phosphorescent dopant serves as a carrier trap to cause recombination of carriers on the phosphorescent dopant, and thereby emission from the phosphorescent dopant occurs. In each type, it is essential that the energy in the excited state of the phosphorescent dopant be lower than that in the excited state of the host compound.

The phosphorescent dopant according to the present invention preferably has an emission wavelength of 480 nm or less.

The phosphorescent dopant according to the present invention is a phosphorescent light-emitting organic metal complex represented by the formula (2) (i.e., phosphorescent light-emitting organic metal complex having a metal atom coordinated with a ligand having a structure represented by the formula (1)). The phosphorescent dopant may be used together with any other compound, such as compounds described in the following patent documents:

For example, International Patent Publication No. WO00/70655, Japanese Patent Laid-Open Nos. 2002-280178, 2001-181616, 2002-280179, 2001-181617, 2002-280180, 2001-247859, 2002-299060, 2001-313178, 2002-302671, 2001-345183, and 2002-324679, International Patent Publication No. WO02/15645, Japanese Patent Laid-Open Nos. 2002-332291, 2002-50484, 2002-332292, and 2002-83684, National Publication of International Patent Application No. 2002-540572, Japanese Patent Laid-Open Nos. 2002-117978, 2002-338588, 2002-170684, and 2002-352960, International Patent Publication No. WO01/93642, Japanese Patent Laid-Open Nos. 2002-50483, 2002-100476, 2002-173674, 2002-359082, 2002-175884, 2002-363552, 2002-184582, and 2003-7469, National Publication of International Patent Application No. 2002-525808, Japanese Patent Laid-Open No. 2003-7471, National Publication of International Patent Application No. 2002-525833, Japanese Patent Laid-Open Nos. 2003-31366, 2002-226495, 2002-234894, 2002-235076, 2002-241751, 2001-319779, 2001-319780, 2002-62824, 2002-100474, 2002-203679, 2002-343572, and 2002-203678.

(Fluorescent Dopant (Also Referred to as Fluorescent Compound))

Examples of the fluorescent dopant include coumarin dyes, pyran dyes, cyanine dyes, chloconium dyes, squarylium dyes, oxobenzanthracene dyes, fluorescein dyes, rhodamine dyes, pyrylium dyes, perylene dyes, stilbene dyes, polythiophene dyes, and compounds having high fluorescence quantum yields such as rare earth fluorescent complexes and laser dyes.

The luminescent dopant according to the present invention may be used together with a plurality of other compounds. A combination of phosphorescent dopants having different structures or a combination of a phosphorescent dopant and a fluorescent dopant may be employed.

Non-limiting examples of known phosphorescent dopant compound that can be preferably used in the present invention are shown below:

[Chem. 30]

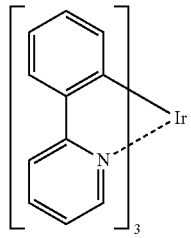

D-1

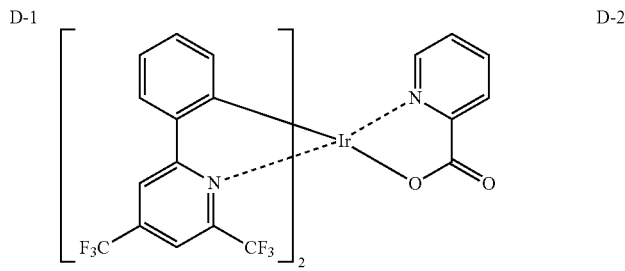

D-2

-continued
D-3
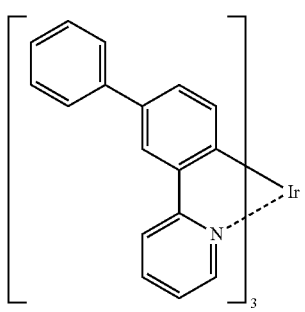
D-4
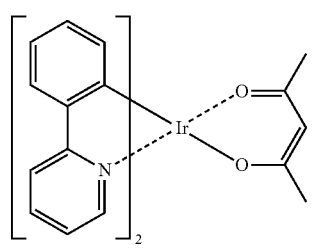
D-5
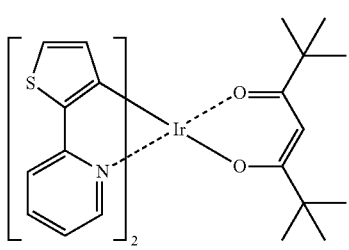
D-6
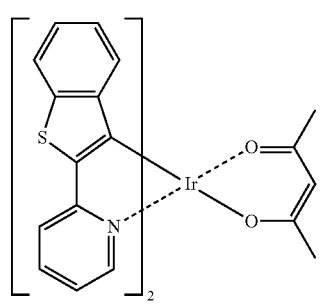
D-7
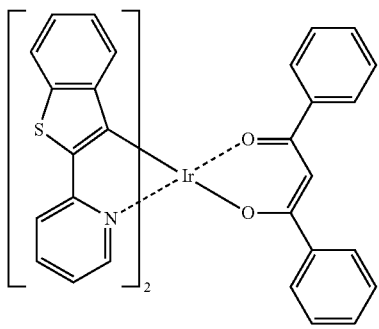
D-8
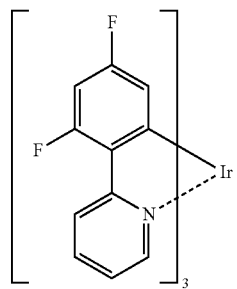
D-9
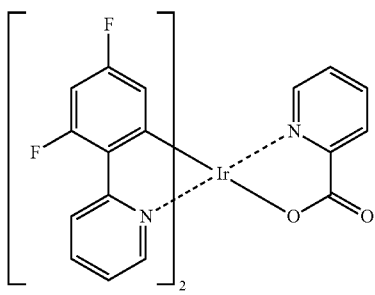
D-10
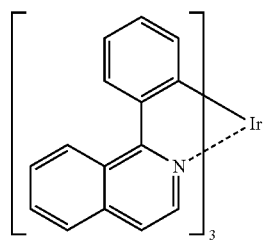
D-11
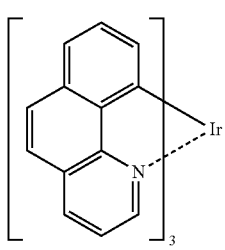
D-12
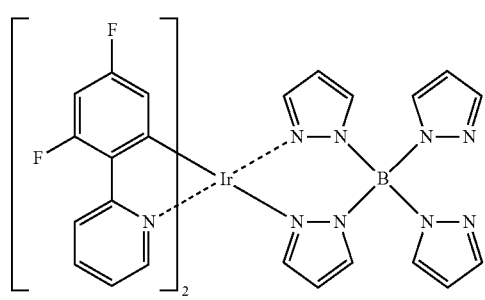

[Chem. 31]
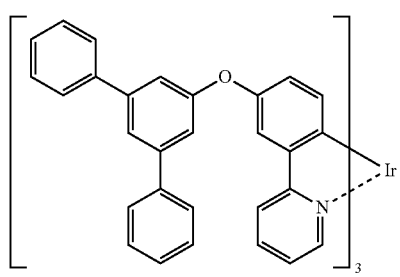
D-13
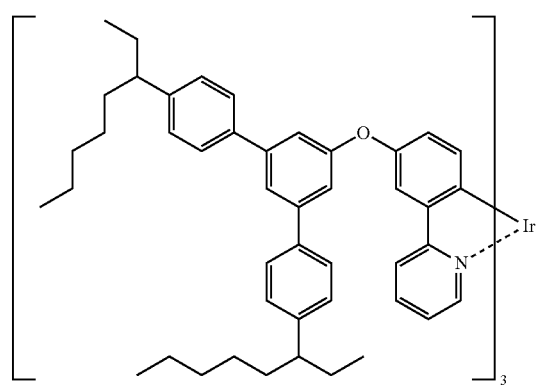
D-14
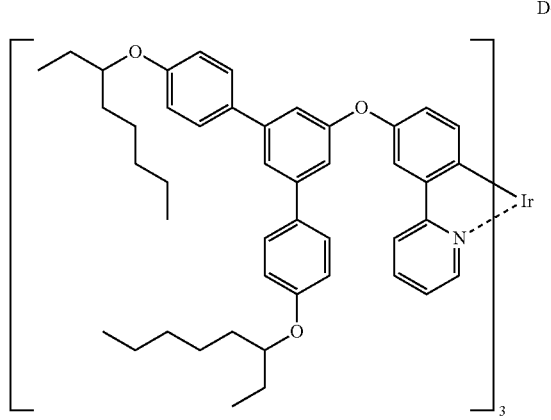
D-15
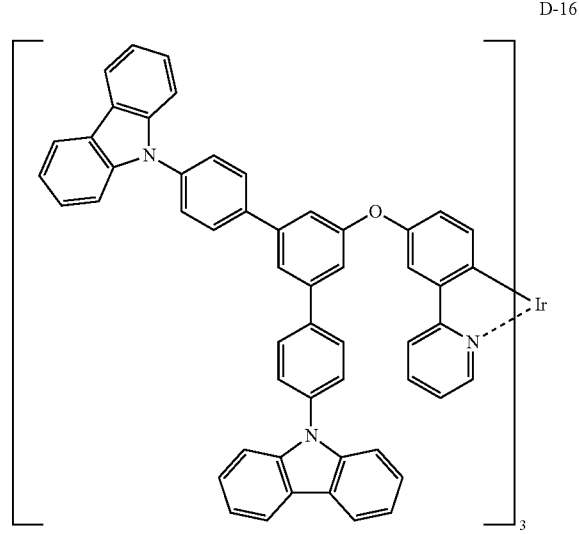
D-16
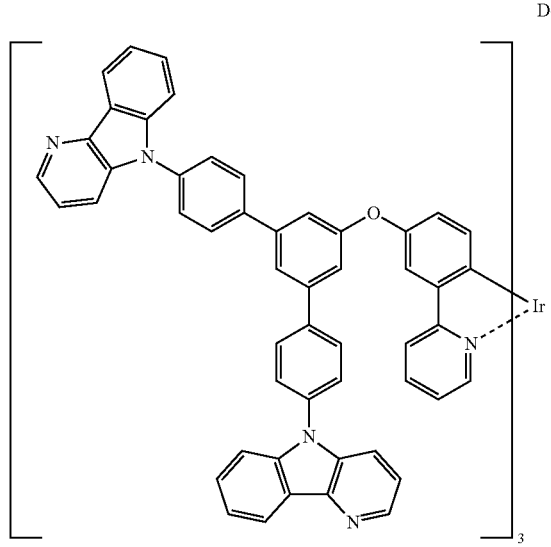
D-17
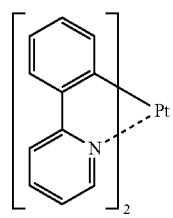
D-18

-continued
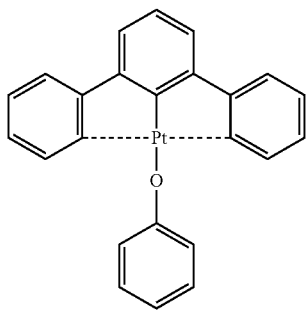
[Chem. 32]
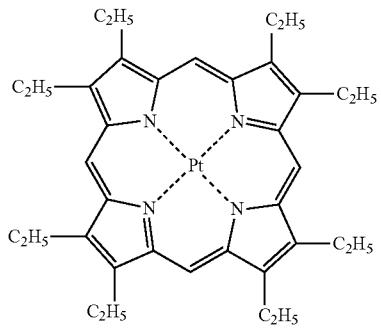
D-19
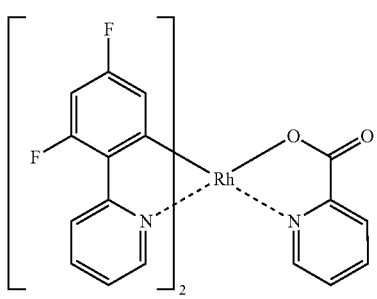
D-20
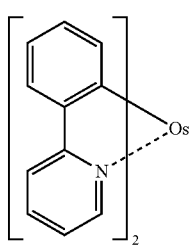
D-21
D-22
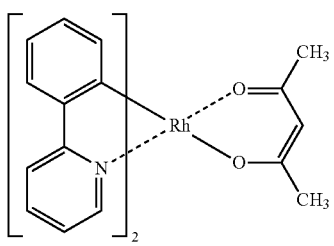
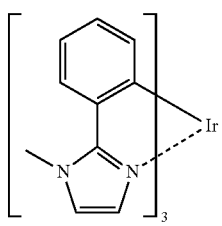
D-23
D-24
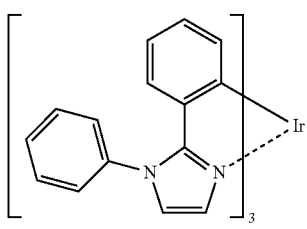
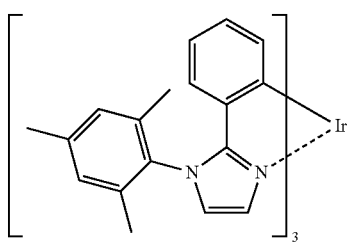
D-25
D-26
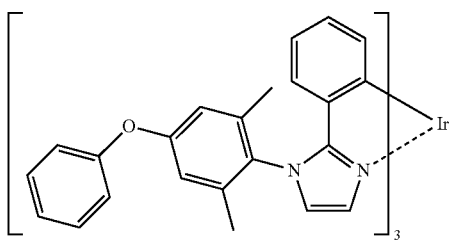
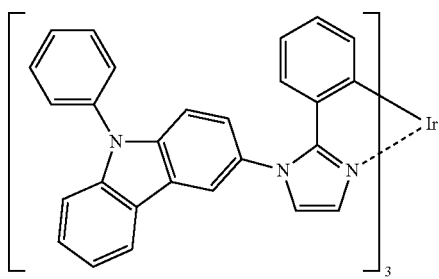
D-27
D-28

-continued
D-29
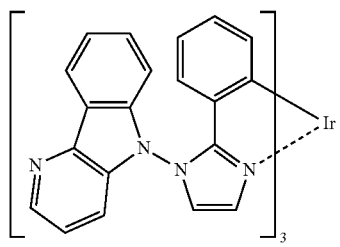
D-30
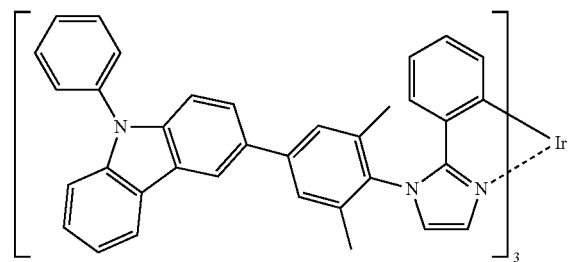
D-31
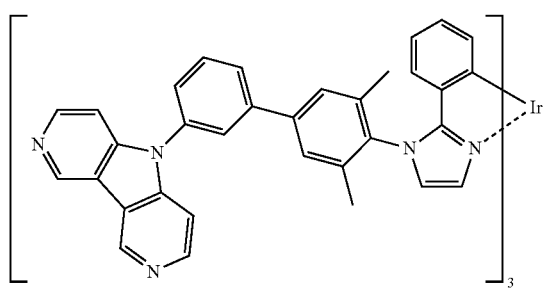
[Chem. 33]
D-32
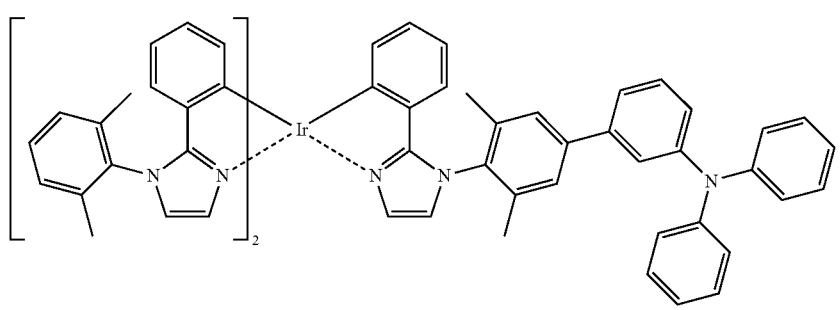
D-33
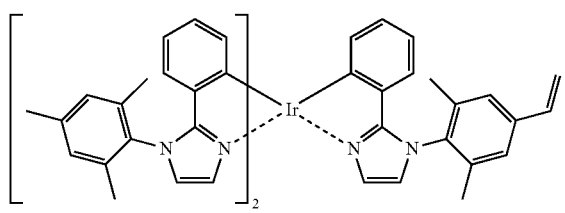
D-34
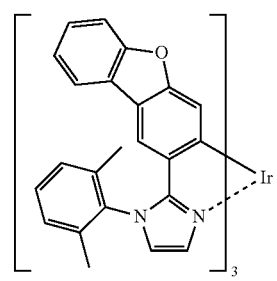
D-35
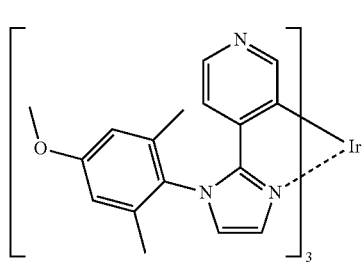
D-36
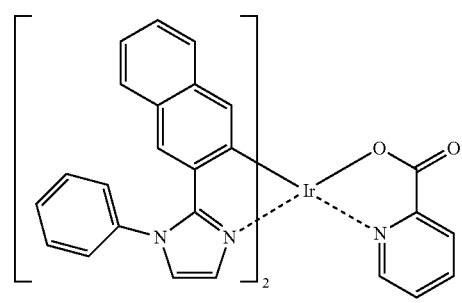

-continued
D-37
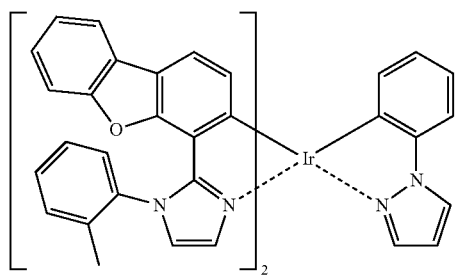
D-38
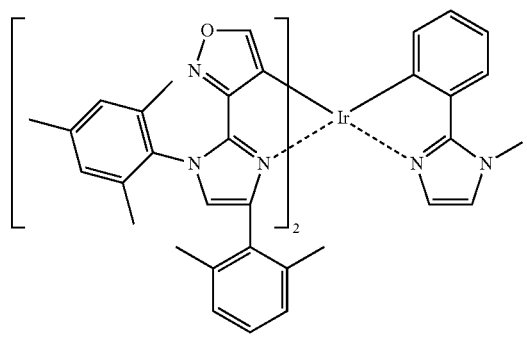
D-39
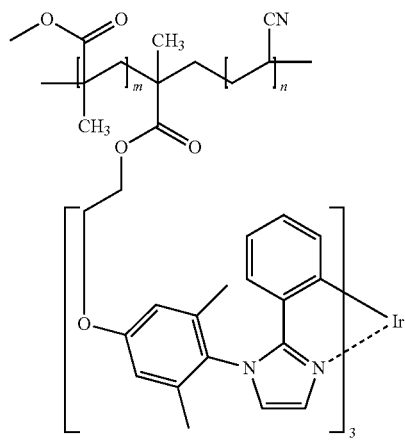
D-40
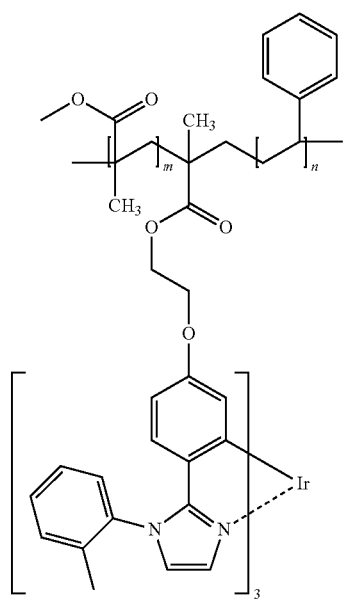
[Chem. 34]
D-41
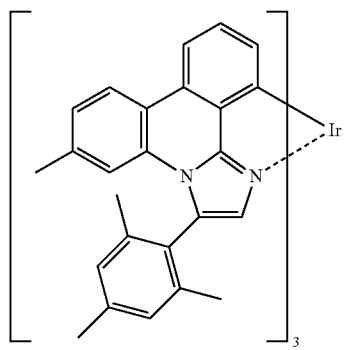
D-42
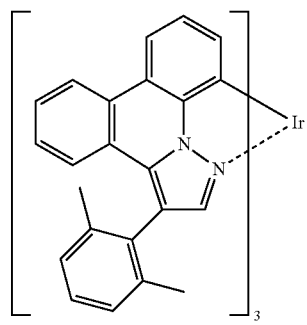

-continued

D-43
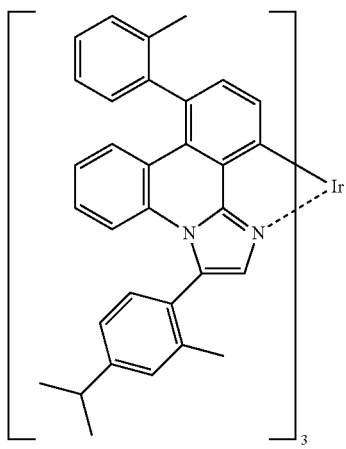

D-44
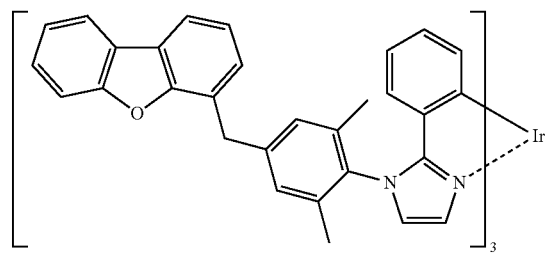

D-45
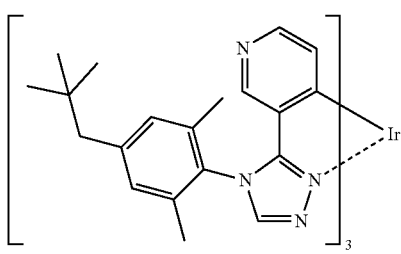

D-46
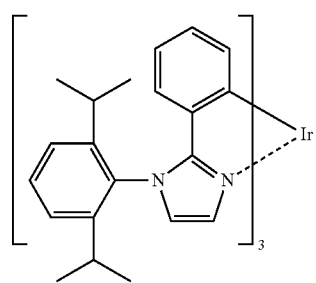

D-47
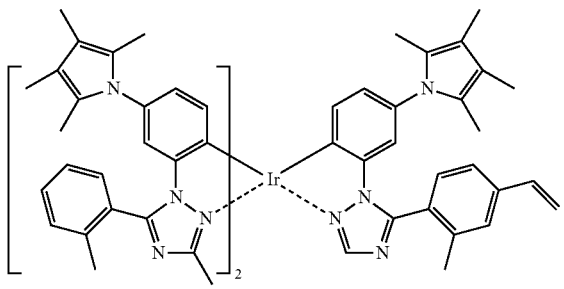

D-48
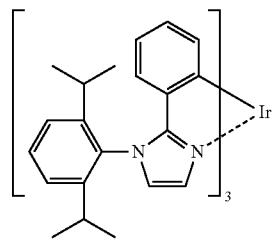

D-49
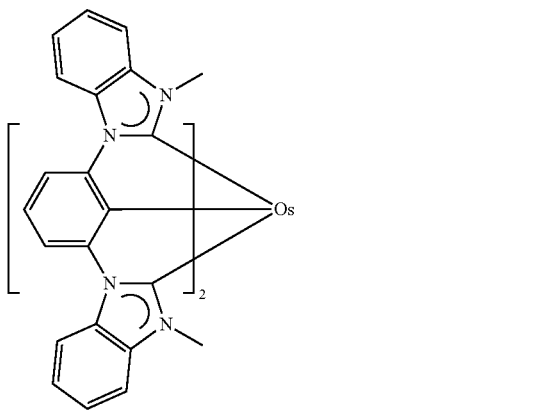

(Luminescent Host Compound (Also Referred to as Luminescent Host))

The host compound in the present invention is defined as a compound that is contained in the light-emitting layer in an amount of 20% by mass or more based on the layer and that has a phosphorescence quantum yield of phosphorescent light emission of less than 0.1, preferably less than 0.01, at room temperature (25° C.). The proportion of the host compound is preferably 20% by mass or more in the light-emitting layer.

The specific host compounds that can be used in the present invention are represented by the formula (4).

The host compound may be a mixture of the compound represented by the formula (4) and any other known compound.

Typical examples of the known compound that can be used include carbazole derivatives, triarylamine derivatives, aromatic compounds, nitrogen-containing heterocyclic compounds, thiophene derivatives, furan derivatives, compounds having basic skeletons of, for example, oligoarylene compounds, carboline derivatives, and diazacarbazole derivatives (herein, the diazacarbazole derivative is a compound having at least one nitrogen atom substituted for any of the carbon atoms on the hydrocarbon ring constituting the carboline ring of a carboline derivative).

The known luminescent host that can be used in the present invention is preferably a compound having hole transportability and electron transportability, preventing the shift of luminescence to the longer wavelength side, and having a high glass transition temperature (Tg). The Tg is more preferably 100° C. or more.

Use of a plurality of luminescent hosts allows the control of the transportation of charge and the increase in the efficiency of the organic EL element.

Furthermore, use of a plurality of known compounds as the phosphorescent dopants allows mixing of different luminescent colors and thereby the generation of any intended emission color.

The luminescent host used in the present invention may be a low-molecular-weight compound, a high-molecular-weight compound having a repeating unit, a low-molecular-weight compound having a polymerizable group such as a vinyl group or an epoxy group (polymerizable luminescent host), or a mixture thereof.

Examples of the known luminescent host are described in the following documents:

Japanese Patent Laid-Open Nos. 2001-257076, 2002-308855, 2001-313179, 2002-319491, 2001-357977, 2002-334786, 2002-8860, 2002-334787, 2002-15871, 2002-334788, 2002-43056, 2002-334789, 2002-75645, 2002-338579, 2002-105445, 2002-343568, 2002-141173, 2002-352957, 2002-203683, 2002-363227, 2002-231453, 2003-3165, 2002-234888, 2003-27048, 2002-255934, 2002-260861, 2002-280183, 2002-299060, 2002-302516, 2002-305083, 2002-305084, and 2002-308837.

(Injecting Layer: Hole-Injecting Layer (Anode Buffer Layer), Electron-Injecting Layer (Cathode Buffer Layer))

Injecting layers, i.e., an electron-injecting layer and a hole-injecting layer, are optionally disposed between the anode and the light-emitting layer or the hole-transporting layer and between the cathode and the light-emitting layer or the electron-transporting layer, as described above.

The injecting layer is provided between the electrode and an organic layer in order to reduce the driving voltage and to improve the luminance and is described in detail in "Denkyoku zairyo (Electrode material)", Div. 2 Chapter 2 (pp. 123-166) of "Yuki EL soshi to sono kogyoka saizensen (Organic EL element and its frontier of industrialization)" (published by NTS Corporation, Nov. 30, 1998). The injecting layer is a hole-injecting layer (anode buffer layer) or an electron-injecting layer (cathode buffer layer).

The anode buffer layer (hole-injecting layer) is also described in detail in Japanese Patent Laid-Open Nos. Hei 9-45479, Hei 9-260062, and Hei 8-288069 for example, and examples thereof include phthalocyanine buffer layers, such as a copper phthalocyanine layer; oxide buffer layers, such as a vanadium oxide layer; amorphous carbon buffer layers; polymer buffer layers containing electroconductive polymers, such as polyaniline (emeraldine) or polythiophene; and ortho-metalated complex layers, such as a tris(2-phenylpyridine)iridium complex layer. In addition, azatriphenylene derivatives described in National Publication of International Patent Application No. 2003-519432 or Japanese Patent Laid-Open No. 2006-135145 for example can be used as hole-injecting materials.

The cathode buffer layer (electron-injecting layer) is also described in detail in Japanese Patent Laid-Open Nos. Hei 6-325871, Hei 9-17574, and Hei 10-74586 for example, and examples thereof include metal buffer layers such as a strontium or aluminum layer; alkali metal compound buffer layers such as a lithium fluoride, sodium fluoride, or potassium fluoride layer; alkali earth metal compound buffer layers such as a magnesium fluoride layer; and oxide buffer layers such as an aluminum oxide layer. The buffer layer (injecting layer) is desirably a significantly thin layer, and preferably has a thickness in a range of 0.1 nm to 5 µm depending on the material.

The materials contained in the anode buffer layer and the cathode buffer layer may be used together with other materials and may be used by being mixed into, for example, the hole-transporting layer or the electron-transporting layer.

(Hole-Transporting Layer)

The hole-transporting layer is composed of a hole-transporting material having hole transportability. The hole-injecting layer and the electron-blocking layer are also categorized into the hole-transporting layer in a broad sense. The hole-transporting layer may have a monolayer or multilayer structure.

The hole-transporting material has a hole injectability or transportability or an electron blockability and may be either an organic material or an inorganic material. Examples of the hole-transporting material include triazole derivatives, oxadiazole derivatives, imidazole derivatives, polyarylalkane derivatives, pyrazoline derivatives, pyrazolone derivatives, phenylenediamine derivatives, arylamine derivatives, amino substituted chalcone derivatives, oxazole derivatives, styryl anthracene derivatives, fluorenone derivatives, hydrazone derivatives, stilbene derivatives, silazane derivatives, aniline copolymers, and electroconductive polymers/oligomers, particularly thiophene oligomers. Azatriphenylene derivatives, such as those described in National Publication of International Patent Application No. 2003-519432 or Japanese Patent Laid-Open No. 2006-135145 for example can also be used as hole-transporting materials.

The hole-transporting materials described above can be used. Preferred are porphyrin compounds, aromatic tertiary amine compounds, and styrylamine compounds, in particular, aromatic tertiary amine compounds.

Typical examples of the aromatic tertiary amine compound and the styrylamine compound include N,N,N',N'-tetraphenyl-4,4'-diaminophenyl; N,N'-diphenyl-N,N'-bis(3-methylphenyl)-(1,1'-biphenyl)-4,4'-diamine (TPD); 2,2-bis(4-di-p-tolylaminophenyl)propane; 1,1-bis(4-di-p-tolylaminophenyl)cyclohexane; N,N,N',N'-tetra-p-tolyl-4,4'-diaminobiphenyl; 1,1-bis(4-di-p-tolylaminophenyl)-4-phenylcyclohexane; bis(4-dimethylamino-2-methylphenyl)phenylmethane; bis(4-di-p-tolylaminophenyl)phenylmethane; N,N'-diphenyl-N,N'-di(4-methoxyphenyl)-

4,4'-diaminobiphenyl; N,N,N',N'-tetraphenyl-4,4'-diaminodiphenyl ether; 4,4'-bis(diphenylamino)quardriphenyl; N,N,N-tri(p-tolyl)amine; 4-(di-p-tolylamino)-4'-[4-(di-p-tolylamino)styryl]stilbene; 4-N,N-diphenylamino-(2-diphenylvinyl)benzene; 3-methoxy-4'-N,N-diphenylaminostylbenzene; N-phenylcarbazole, compounds having two condensed aromatic rings in the molecule, described in U.S. Pat. No. 5,061,569 such as 4,4'-bis[N-(1-naphthyl)-N-phenylamino]biphenyl (NPD), and compounds described in Japanese Patent Laid-Open No. Hei 4-308688 such as 4,4',4"-tris[N-(3-methylphenyl)-N-phenylamino]triphenylamine (MTDATA) in which three triphenylamine units are bonded into a starburst form.

Polymer materials having the compounds mentioned above introduced into their chains or having the compounds as main chains can also be used.

Inorganic compounds such as p-type Si and p-type SiC can also be used as the hole-injecting material or the hole-transporting material.

Cyclo-metalated complexes and ortho-metalated complexes represented by copper phthalocyanine and tris(2-phenylpyridine)iridium complexes can also be used as the hole-transporting material.

So-called p-type hole-transporting materials as described in Japanese Patent Laid-Open No. Hei 11-251067 or in J. Huang, et al., (Applied Physics Letters, 80 (2002), p. 139) can also be used. In the present invention, these materials can provide highly efficient light-emitting elements and, therefore, are preferably used.

The hole-transporting layer can be formed in the form of a thin film prepared from the hole-transporting material by a known method such as vacuum deposition, spin coating, casting, printing including ink jetting, or LB deposition.

The hole-transporting layer may have any thickness, which is usually about 5 nm to 5 μm and preferably 5 to 200 nm. The hole-transporting layer may have a monolayer configuration composed of one or more of the materials mentioned above.

A hole-transporting layer having high p-type properties doped with an impurity can also be used. Examples thereof include those described in, for example, Japanese Patent Laid-Open Nos. Hei 4-297076, 2000-196140, and 2001-102175 and J. Appl. Phys., 95, 5773 (2004).

In the present invention, the use of such hole-transporting layer having high p-type properties is preferred for producing an element with lower power consumption.

Non-limiting examples of the compound that is preferably used in formation of the hole-injecting layer and the hole-transporting layer of the organic EL element of the present invention are shown below:

[Chem. 35]

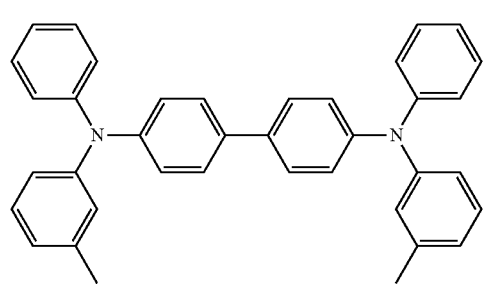

(TPD)

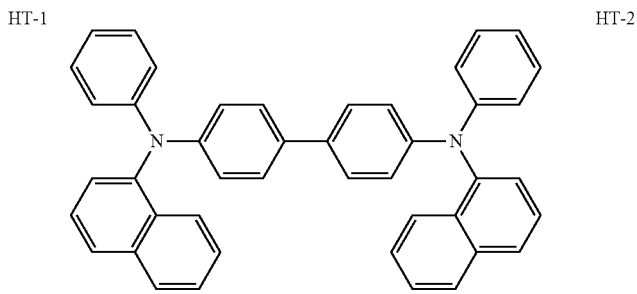

(α-NPD)

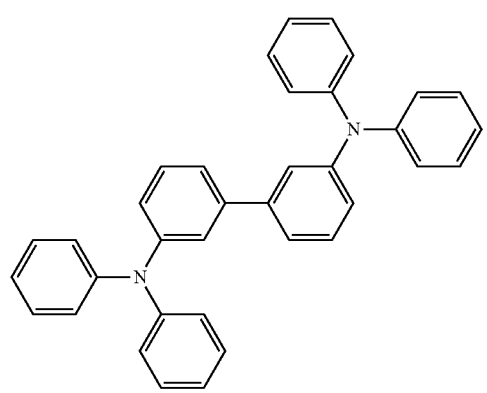

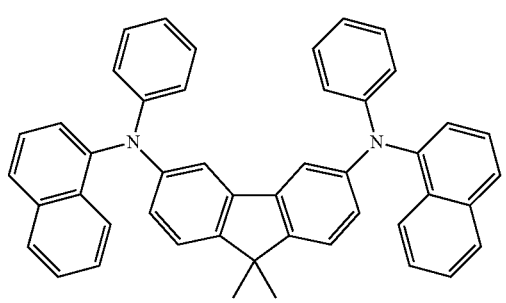

-continued
HT-5
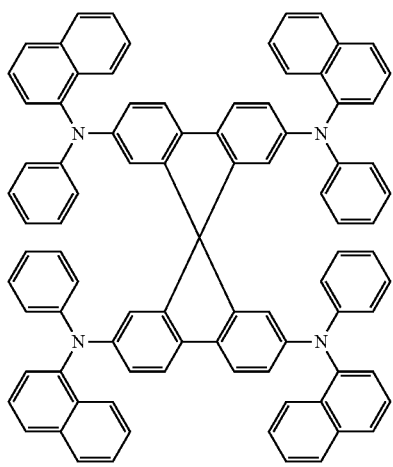
HT-6
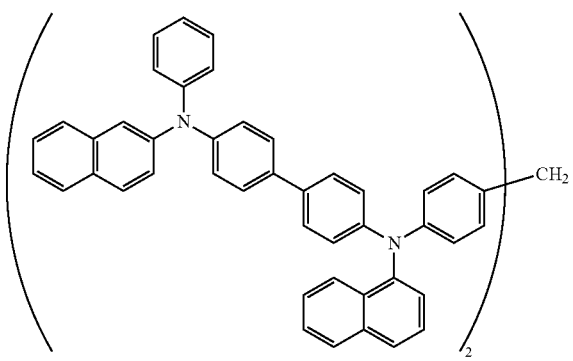
[Chem. 36]
HT-7
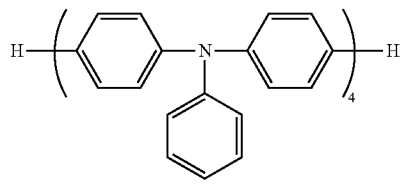
HT-8
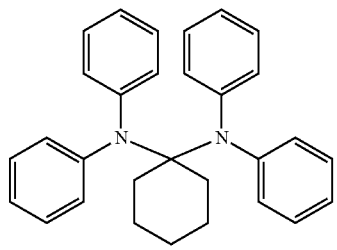
HT-9
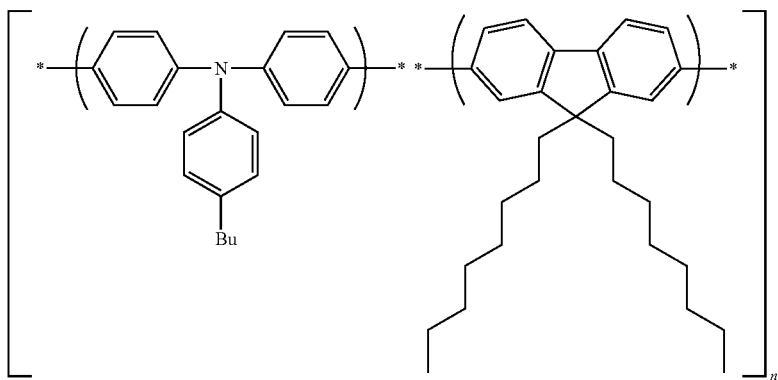
(F8-TFB)
HT-10
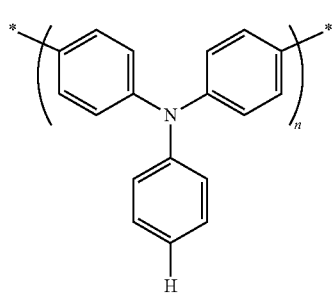
HT-11
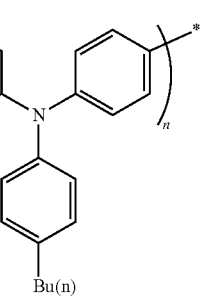

-continued
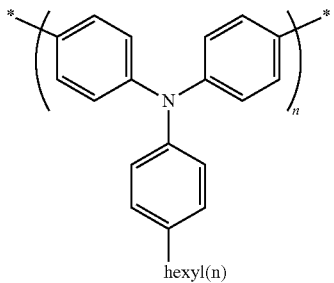
HT-12
[Chem. 37]
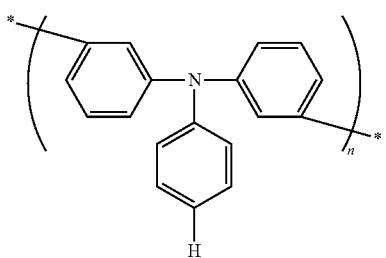
HT-13
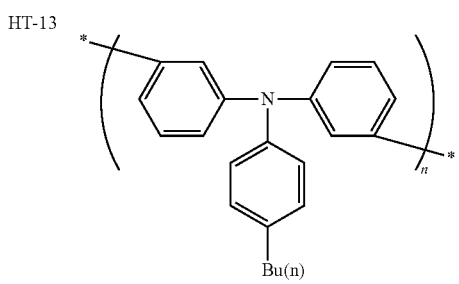
HT-14
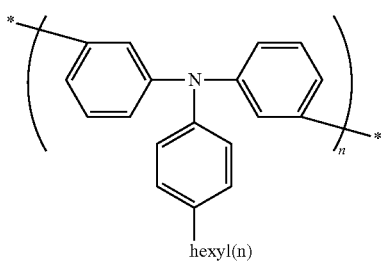
HT-15
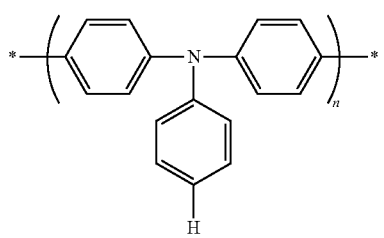
HT-16
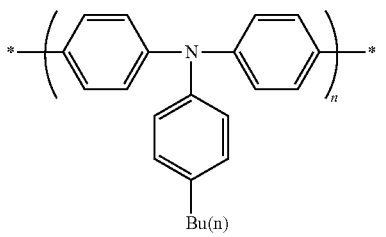
HT-17
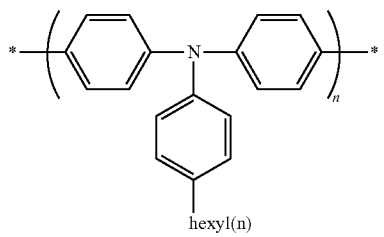
HT-18
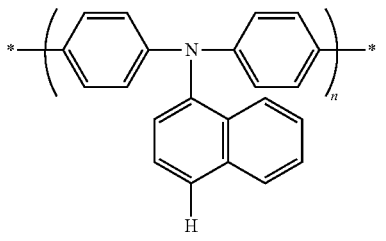
HT-19
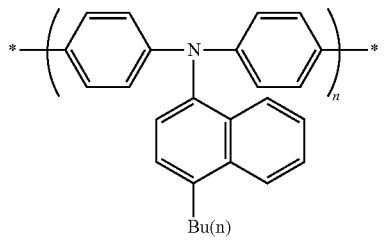
HT-20
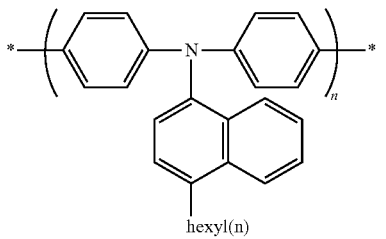
HT-21

-continued
[Chem. 38]
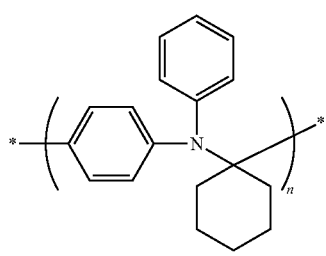
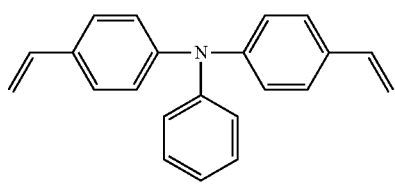
HT-22 HT-23
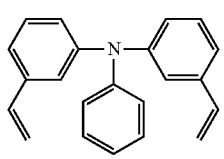
HT-24
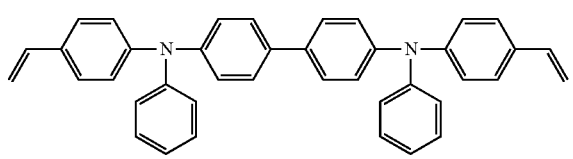
HT-25
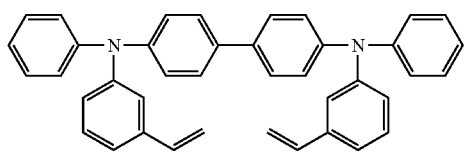
HT-26
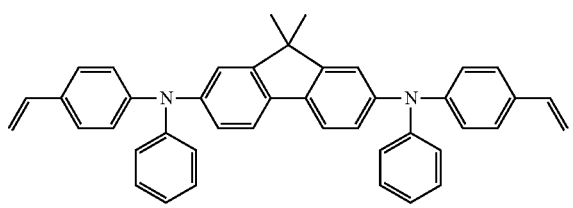
HT-27
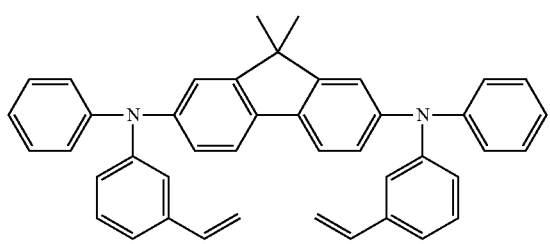
HT-28
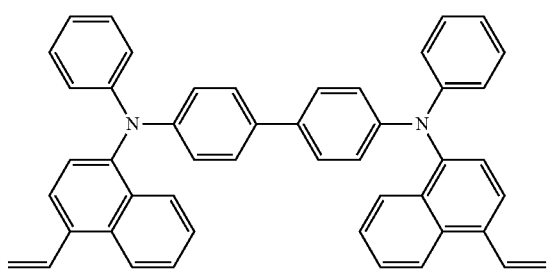
HT-29
[Chem. 39]
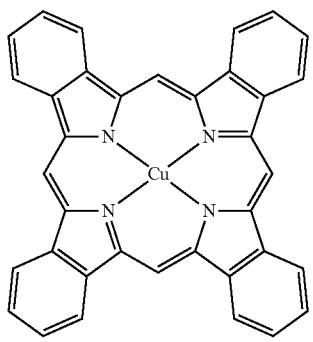
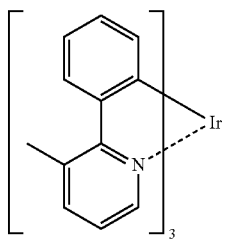
HT-30 HT-31
$-\!\!+\!\!CH_xF_y\!\!+\!\!_n\!-$
HT-32 HT-33
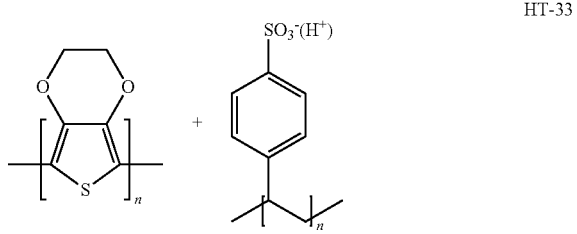

-continued
HT-34
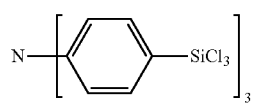
HT-35
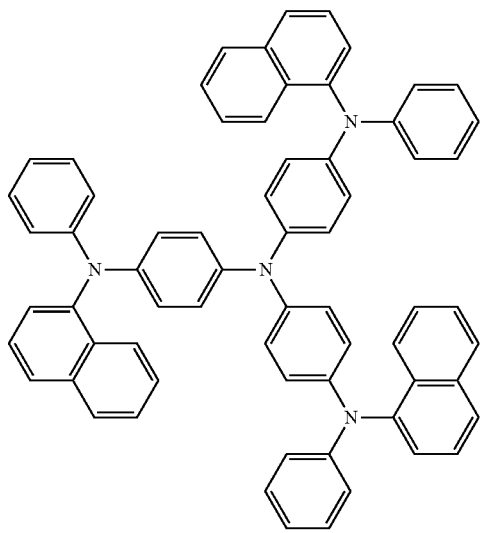
HT-36
HT-37
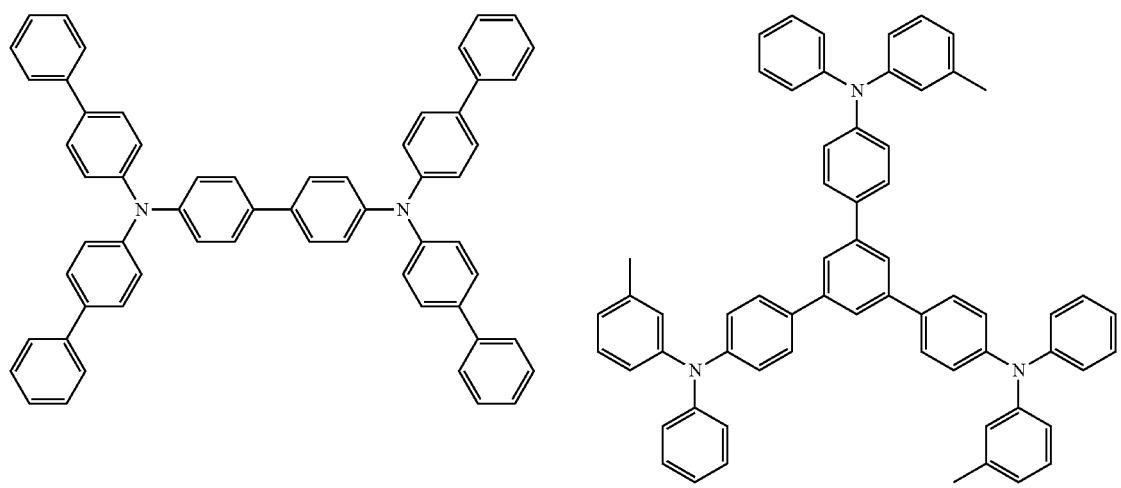
HT-38
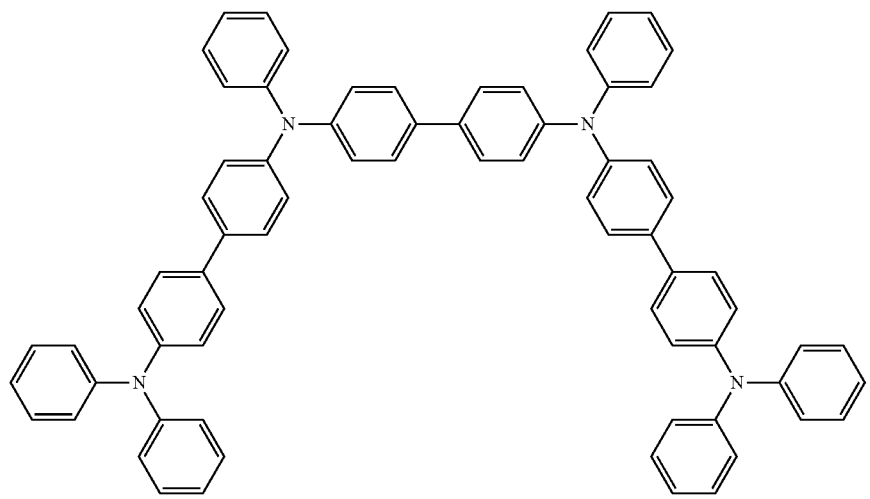

HT-39
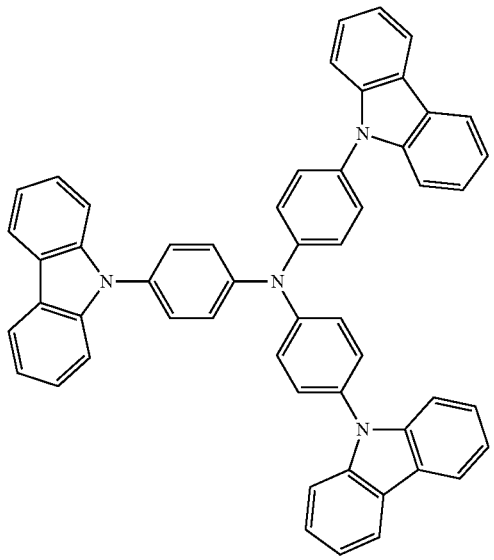
HT-40
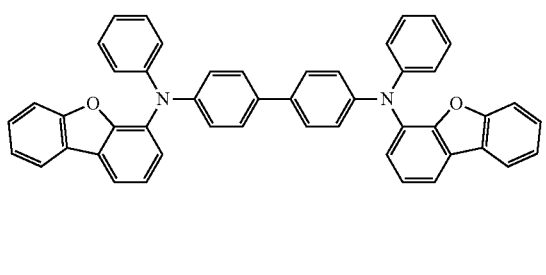
HT-41
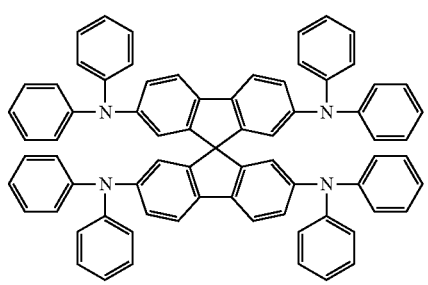
HT-42
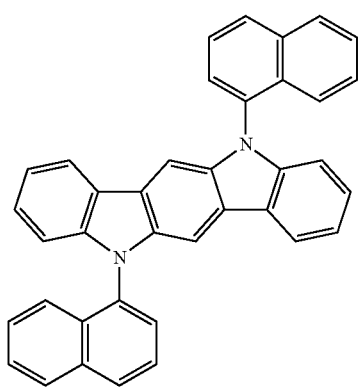
HT-43
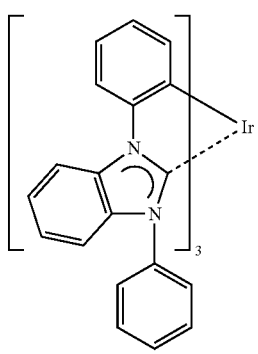
HT-44
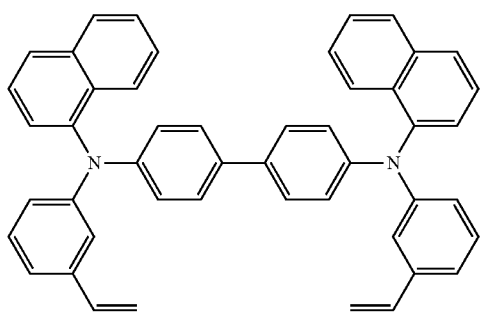
HT-45
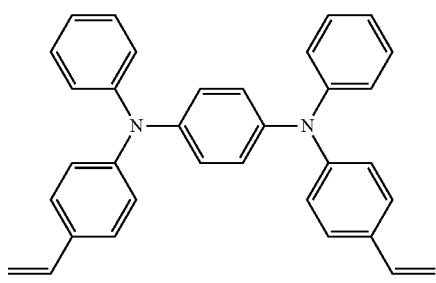

(Electron-Transporting Layer)

The electron-transporting layer is composed of a material having an electron transportability, and the electron-injecting layer and the hole-blocking layer are categorized into the electron-transporting layer in a broad sense. The electron-transporting layer may have a monolayer or multilayer structure.

The electron-transporting material (including hole-blocking material and electron-transporting material) contained in the electron-transporting layer may be any material that can transport electrons injected from a cathode to a light-emitting layer. The electron-transporting layer can be composed of a single material or two or more materials appropriately selected from known compounds.

Examples of the known materials that are contained in the electron-transporting layer (hereinafter, referred to as electron-transporting material) include nitro-substituted fluorene derivatives, diphenylquinone derivatives, thiopyran dioxide derivatives, heterocyclic tetracarboxylic anhydride, such as naphthalene perylene, carbodiimide, fluorenylidenemethane derivatives, anthraquinodimethane and anthrone derivatives, oxadiazole derivatives, carboline derivatives, and azacarbazole derivatives.

The azacarbazole derivative is a compound having at least one nitrogen atom substituted for any of the carbon atoms on the carbazole ring.

Furthermore, thiadiazole derivatives in which oxygen atoms of the oxadiazole rings of the oxadiazole derivatives mentioned above are replaced with sulfur atoms and quinoxaline derivatives having quinoxaline rings known as electron withdrawing groups can be used as the electron-transporting materials.

Polymer materials having these compounds introduced into their chains or having the compounds as main chains can also be used.

Examples of the usable electron-transporting material include metal complexes of 8-quinolinol derivatives, such as aluminum tris(8-quinolinol) (Alq), aluminum tris(5,7-dichloro-8-quinolinol), aluminum tris(5,7-dibromo-8-quinolinol), aluminum tris(2-methyl-8-quinolinol), aluminum tris(5-methyl-8-quinolinol), and zinc bis(8-quinolinol) (Znq), and metal complexes in which the central metals of the metal complexes mentioned above are replaced with In, Mg, Cu, Ca, Sn, Ga, or Pb.

In addition, the electron-transporting material may be a metal-free or metal-containing phthalocyanine or its derivative having an end substituted by an alkyl or sulfonate group, for example.

Alternatively, the electron-transporting material may be an inorganic semiconductor, such as n-type Si and n-type SiC, as in the hole-injecting layer or the hole-transporting layer.

The electron-transporting layer may have any thickness, which is usually about 5 to 5000 nm and preferably 5 to 200 nm. The electron-transporting layer may have a monolayer configuration composed of one or more of the materials mentioned above or may have a laminate structure composed of a plurality of layers.

An electron-transporting layer having high n-type properties doped with an impurity can also be used. Examples thereof include those described in, for example, Japanese Patent Laid-Open Nos. Hei 4-297076, Hei 10-270172, 2000-196140, and 2001-102175 and 0.1. Appl. Phys., 95, 5773 (2004).

Non-limiting examples of the known compound (electron-transporting material) that is preferably used in the formation of the electron-transporting layer of the white-emitting organic EL element of the present invention are shown below:

[Chem. 40]

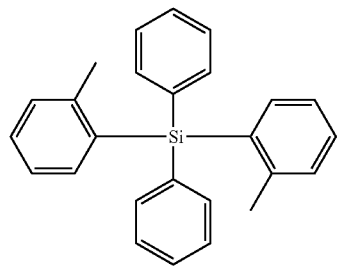

ET-1

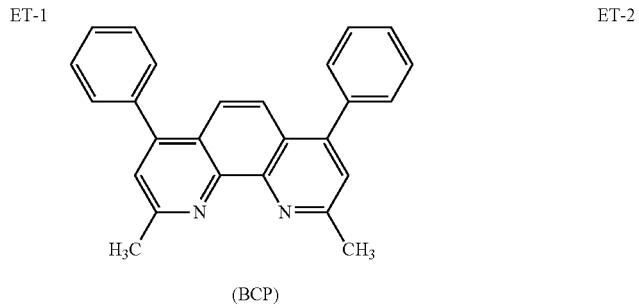

ET-2

(BCP)

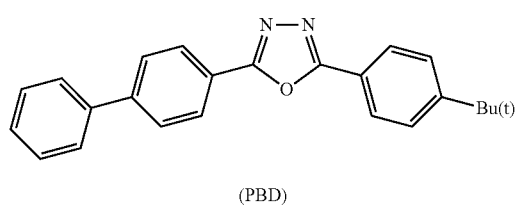

ET-3

(PBD)

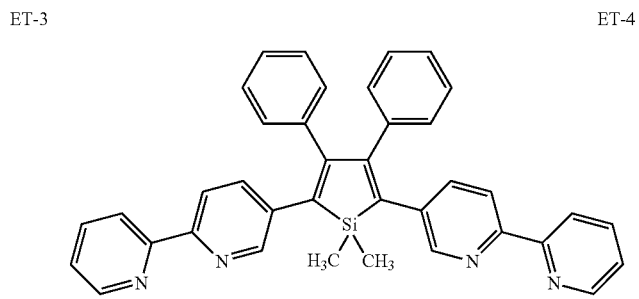

ET-4

-continued
ET-5
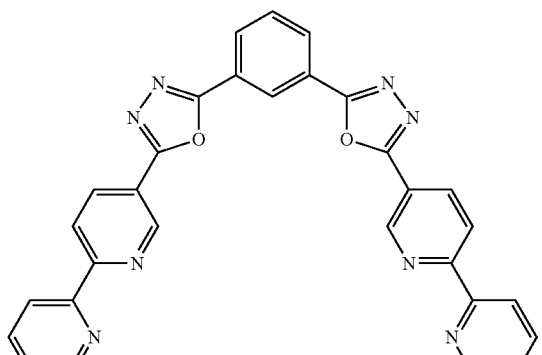
ET-6
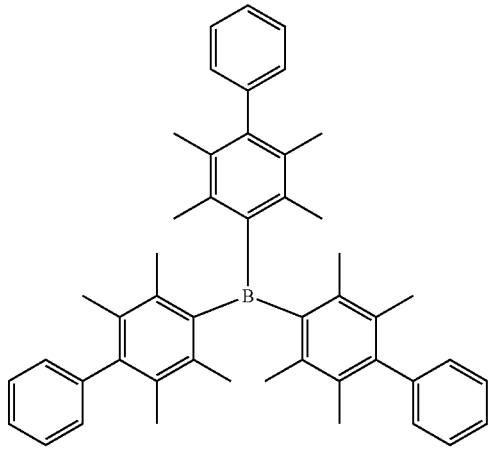
ET-7
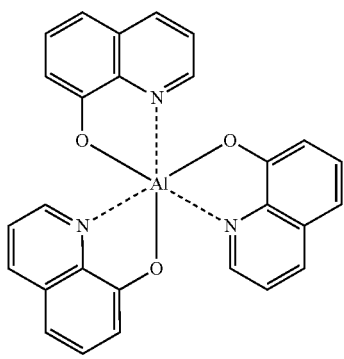
(Alq₃)
ET-8
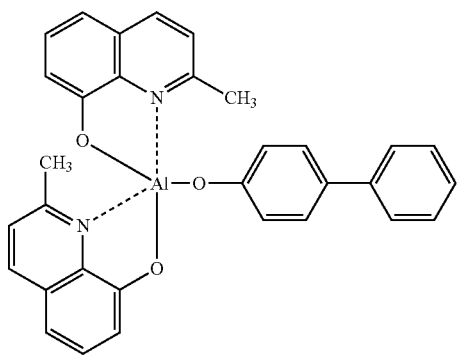
(BAlq)
[Chem. 41]
ET-9
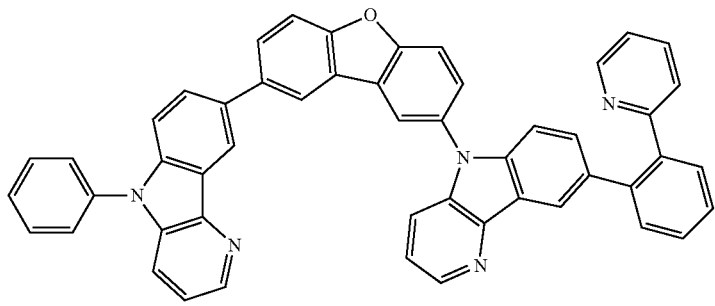
ET-10
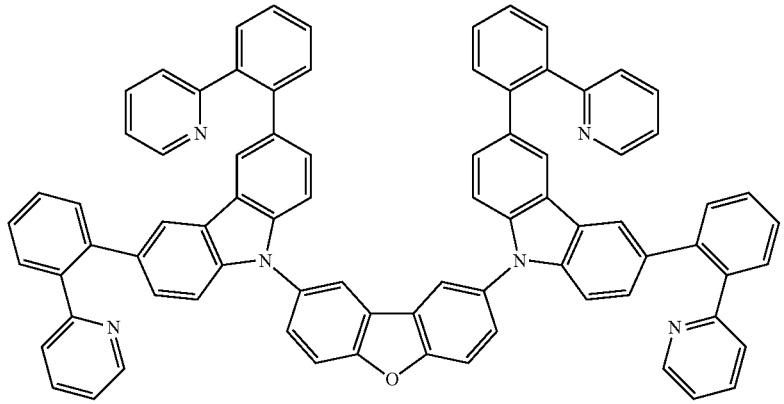

ET-11

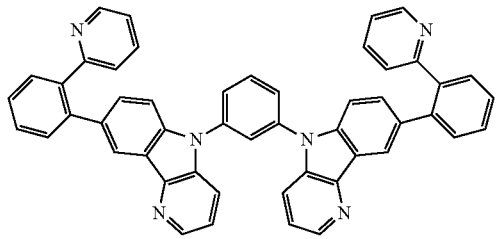

ET-12

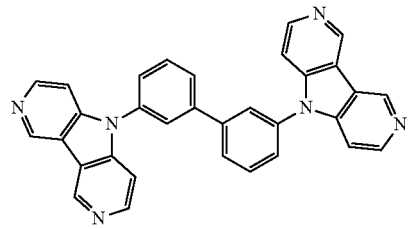

ET-13

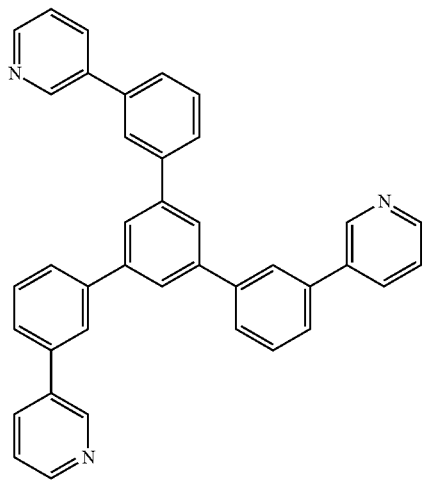

ET-14

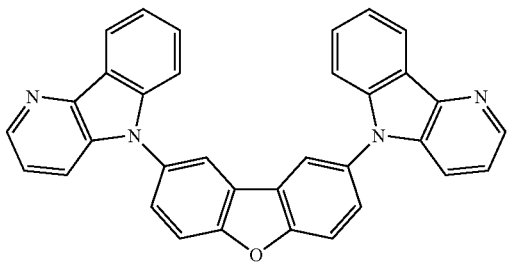

ET-15

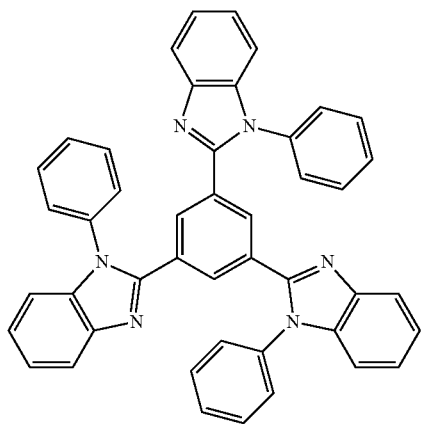

ET-16

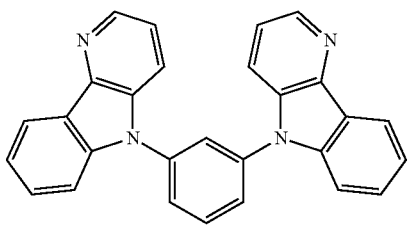

ET-17

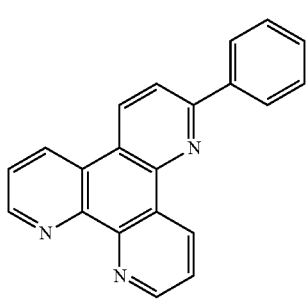

(Blocking Layer: Hole-Blocking Layer, Electron-Blocking Layer)

The blocking layer is optionally provided in addition to the fundamental structural layer of the organic compound thin film as described above. The blocking layer is, for example, a hole-blocking layer described in Japanese Patent Laid-Open Nos. Hei 11-204258 and Hei 11-204359 and on page 237 of "Organic EL element and its frontier of industrialization" (published by NTS Corporation, Nov. 30, 1998) for example.

The hole-blocking layer functions as an electron-transporting layer in a broad sense and is composed of a material having electron transportability but extremely poor hole transportability and can increase the probability of recombination of electrons and holes by transporting electrons and blocking holes.

The structure of an electron-transporting layer described above can be optionally used as a hole-blocking layer according to the present invention.

The hole-blocking layer of the organic EL element of the present invention preferably adjoins the light-emitting layer.

The hole-blocking layer preferably contains a nitrogen-containing compound, such as a carbazole derivative, an azacarbazole derivative (herein, the azacarbazole derivative is a compound having at least one nitrogen atom substituted for any of the carbon atoms on the carbazole ring), or a pyridine derivative.

In the present invention, when a plurality of light-emitting layers emitting lights of different colors are included, a light-emitting layer with shortest maximum light emission wavelength among the light-emitting layers is preferably disposed closest to the anode. In such a case, an additional hole-blocking layer is preferably disposed between the shortest-wavelength layer and a light-emitting layer second closest to the anode.

Furthermore, at least 50% by mass of the compounds contained in the hole-blocking layer disposed at the position described above preferably has an ionization potential that is at least 0.3 eV higher than that of the host compound contained in the shortest wavelength light-emitting layer.

The ionization potential is defined by the energy necessary for releasing an electron in the highest occupied molecular orbital (HOMO) level of a compound to the vacuum level and can be determined, for example, as follows:

(1) The ionization potential can be determined with molecular orbital calculation software, Gaussian 98 (Gaussian 98, Revision A.11.4, M. J. Frisch, et al., Gaussian. Inc., Pittsburgh Pa., 2002) manufactured by Gaussian, Inc. in U.S.A. as a value (eV unit conversion value) calculated by structural optimization using B3LYP/6-31G* as a keyword. This calculated value is valid because of a high correlation between the calculated values determined by such a method and experimental values.

(2) The ionization potential can also be directly measured by photoelectron spectroscopy. For example, a low-energy electron spectrometer "Model AC-1", manufactured by Riken Keiki Co., Ltd. or a method known as ultraviolet photoelectron spectroscopy can be suitably employed.

Meanwhile, the electron-blocking layer functions as a hole-transporting layer in a broad sense and is composed of a material having hole transportability but extremely poor electron transportability and can increase the probability of recombination of electrons and holes by transporting holes and blocking electrons.

The structure of a hole-transporting layer described above can be optionally used as an electron-blocking layer. The hole-blocking layer and the electron-blocking layer according to the present invention each preferably have a thickness of 3 to 100 nm and more preferably 3 to 30 nm.

(Anode)

The electrode material of the anode of the organic EL element is preferably a metal, alloy, or electroconductive compound having a high work function (not less than 4 eV) or a mixture thereof. Examples of the electrode material include metals such as Au and transparent electroconductive materials such as CuI, indium tin oxide (ITO), $SnO_2$, and ZnO.

A material, such as IDIXO ($In_2O_3$—ZnO), capable of forming an amorphous transparent electroconductive film may be used. The anode may be produced by forming a thin film from the electrode material by a method, such as deposition or sputtering, and then patterning the film into a desired shape by photolithography. If a high precision pattern is not required (not less than about 100 μm), the pattern may be formed by depositing or sputtering the electrode material through a mask having a desired shape.

Alternatively, for a coatable material, such as an organic electroconductive compound, wet coating, such as printing or coating, is also available. For extraction of light from the anode, the transmittance of the anode is desirably 10% or more, and the sheet resistance of the anode is preferably several hundred ohms per square or less. The thickness of the layer is usually in a range of 10 to 1000 nm and preferably 10 to 200 nm depending on the material.

(Cathode)

On the contrary, the electrode material of the cathode is preferably a metal (referred to as electron-injecting metal), alloy, or electroconductive compound having a low work function (not higher than 4 eV) or a mixture thereof.

Examples of the electrode material include sodium, sodium-potassium alloys, magnesium, lithium, mixtures of magnesium and copper, mixtures of magnesium and silver, mixtures of magnesium and aluminum, mixtures of magnesium and indium, mixtures of aluminum and aluminum oxide ($Al_2O_3$), indium, mixtures of lithium and aluminum, and rare-earth metals.

Among them, from the viewpoint of the electron injectability and resistance to oxidation, preferred are mixtures of an electron-injecting metal and a second metal having a work function higher than that of the electron-injecting metal and being stable, such as mixtures of magnesium and silver, mixtures of magnesium and aluminum, mixtures of magnesium and indium, mixtures of aluminum and aluminum oxide ($Al_2O_3$), mixtures of lithium and aluminum, and aluminum.

The cathode can be produced by forming a thin film from the electrode material by a method, such as deposition or sputtering. The cathode preferably has a sheet resistance of several hundred ohms per square or less and a thickness in a range of usually 10 nm to 5 μm and preferably 50 to 200 nm.

If either the anode or the cathode of the organic EL element is transparent or translucent, the emitted light can pass therethrough to advantageously increase the luminance.

A transparent or translucent cathode can be produced by forming a film having a thickness of 1 to 20 nm from the metal mentioned above and then forming a layer of an electroconductive transparent material exemplified in the description of the anode on the metal film. This process can be applied to produce an element having a transparent anode and a transparent cathode.

(Supporting Substrate)

The supporting substrate (also referred to as base, substrate, base member, or support) that can be used for the organic EL element of the present invention may be composed of any material, such as glass or plastic, and may be transparent or opaque. For extraction of light from the supporting substrate side, the supporting substrate is preferably transparent.

Examples of the transparent supporting substrate preferably used include glass, quartz, and transparent resin films. Particularly preferred supporting substrate is a resin film capable of imparting flexibility to the organic EL element.

Examples of the resin film include films of polyesters such as polyethylene terephthalate (PET) and polyethylene naphthalate (PEN); polyethylene; polypropylene; cellophane; cellulose esters and their derivatives such as cellulose diacetate, cellulose triacetate, cellulose acetate butylate, cellulose acetate propionate (CAP), cellulose acetate phthalate (TAC), and cellulose nitrate; polyvinylidene chloride; polyvinyl alcohol; poly(ethylene-vinyl alcohol); syndiotactic polystyrene; polycarbonates; norbornene resins; polymethylpentene; polyether ketones; polyimides; polyether sulfones (PESs); polyphenylene sulfide, polysulfones; polyether imides; polyether ketone imides; polyamides; fluorine resins; Nylon; poly(methyl methacrylate); acrylics and polyarylates; and cycloolefin resins such as ARTON (trade name, manufactured by JSR Corp.) and APE (trade name, manufactured by Mitsui Chemicals Inc.).

On the surface of the resin film, an inorganic or organic coating film or a hybrid coating film composed of the both may be formed. The coating film is preferably a barrier film having a water vapor transmittance (permeability) of 0.01 g/(m$^2$·24 h) or less (at 25±0.5° C. and 90±2% relative humidity (RH)) measured by a method in accordance with JIS K 7129-1992, and more preferably a high barrier film having an oxygen transmittance of $10^{-3}$ mL/(m$^2$·24 h·MPa) or less measured by a method in accordance with JIS K 7126-1987 and a water vapor transmittance of $10^{-5}$ g/(m$^2$·24 h) or less.

The barrier film may be formed of any material that can block migration of substances such as moisture and oxygen causing degradation of the element, and usable examples of the material include silicon oxide, silicon dioxide, and silicon nitride.

In order to reduce the fragility of the film, a barrier film having a laminate structure composed of an inorganic layer and an organic material layer is preferred. The inorganic layer(s) and the organic material layer(s) may be laminated in any order, and it is preferable that the both layers be alternately laminated multiple times.

The barrier film may be formed by any method, for example, vacuum deposition, sputtering, reactive sputtering, molecular beam epitaxy, ionized-cluster beam deposition, ion plating, plasma polymerization, atmospheric pressure plasma polymerization, plasma CVD, laser CVD, thermal CVD, or coating. Particularly preferred method is atmospheric pressure plasma polymerization as described in Japanese Patent Laid-Open No. 2004-68143.

Examples of the opaque supporting substrate include a metal plate or film of, for example, aluminum and stainless steel; opaque resin substrate; and ceramic substrate.

The external extraction efficiency of light of the organic EL element of the present invention at room temperature is preferably 1% or more and more preferably 5% or more.

The external quantum efficiency (%) is defined as (the number of photons emitted from the organic EL element to the exterior)/(the number of electrons supplied to the organic EL element)×100.

A hue improving filter such as a color filter or a color conversion filter that converts the color of light emitted by the organic EL element to many colors using a fluorescent compound may be used in combination. In order to use the color conversion filter effectively, the λmax of the light emitted from the organic EL element is preferably 480 nm or less.

(Method of Producing Organic EL Element)

An example method of producing the organic EL, element will now be described. This element is composed of an anode, a hole-injecting layer, a hole-transporting layer, a light-emitting layer, a hole-blocking layer, an electron-transporting layer, a cathode buffer layer (electron-injecting layer), and a cathode.

A thin film having thickness of 1 μm or less, preferably 10 to 200 nm, is formed with a desired electrode material, for example, a material for an anode, on a suitable base to produce an anode.

Subsequently, thin films of materials for the elements, i.e., a hole-injecting layer, a hole-transporting layer, a light-emitting layer, a hole-blocking layer, an electron-transporting layer and a cathode buffer layer, each containing an organic compound, are formed on the anode.

In the organic EL element emitting phosphorescent light of the present invention, at least the cathode and the electron-transporting layer adjoining the cathode are applied and formed by a wet process.

Among the wet processes such as spin coating, casting, die coating, blade coating, roll coating, ink jetting, printing, spray coating, curtain coating and LB deposition, a process showing high adaptability to a roll-to-roll system such as die coating, roll coating, ink jetting or spray coating is preferred because of production of high-precision thin films and high productivity. A different film-forming process may be applied to each layer.

Usable examples of media for dissolving or dispersing the organic EL materials according to the present invention include ketones such as methyl ethyl ketone and cyclohexanone; aliphatic acid esters such as ethyl acetate; halogenated hydrocarbons such as dichlorobenzene; aromatic hydrocarbons such as toluene, xylene, mesitylene, and cyclohexylbenzene; aliphatic hydrocarbons such as cyclohexane, decaline, and dodecane; and organic solvents such as DMF and DMSO.

Dispersion can be performed by, for example, ultrasonic wave dispersion, high shearing force dispersion, or medium dispersion.

After formation of these layers, a thin film of a material for a cathode is formed thereon into a thickness of 1 μm or less, preferably in a range of 50 to 200 nm to provide a cathode to give a desired organic EL element.

Alternatively, the organic EL element can also be produced in the reverse order, i.e., in order of a cathode, a cathode buffer layer, an electron-transporting layer, a hole-blocking layer, a light-emitting layer, a hole-transporting layer, a hole-injecting layer, and an anode.

When a direct current voltage of about 2 to 40 V is applied to the resulting multichromatic display device including the anode at a positive (+) polarity and the cathode at a negative (−) polarity, luminescence can be observed. Alternatively, an alternating voltage may be applied. The alternating current to be applied may have any wave shape.

In the production of the organic EL element of the present invention, the steps of producing the layers from the hole-injecting layer to the cathode are preferably performed with a single vacuuming operation. Alternatively, a partly formed organic EL element may be taken out and another process may be performed. In such a case, the process is preferably performed under a dry inert gas atmosphere.

(Sealing)

Examples of the sealing means used in the present invention include a sealing member bonded to the electrode and supporting substrate with an adhesive.

The sealing member is disposed so as to cover the displaying area of the organic EL element and may be a concave plate or a flat plate. The sealing member may have any transparency and electrical insulation.

Examples of the sealing member include glass plates, polymer plates and films, and metal plates and films. Examples of the glass plate include soda-lime glass, barium/strontium-containing glass, lead glass, aluminosilicate glass, borosilicate glass, barium borosilicate glass, and quartz plates.

Examples of the polymer plate include polycarbonate, acryl, polyethylene terephthalate, polyether sulfide, and polysulfone plates. The metal plate may be composed of at least one metal or alloy selected from the group consisting of stainless steel, iron, copper, aluminum, magnesium, nickel, zinc, chromium, titanium, molybdenum, silicon, germanium, and tantalum.

In the present invention, a polymer film or a metal film is preferably used, from the viewpoint of a reduction in the thickness of the element.

The polymer film preferably has an oxygen transmittance of $1/10^{-3}$ mL/(m$^2 \cdot$24 h$\cdot$MPa) or less measured by a method in accordance with JIS K 7126-1987 and a water vapor transmittance of $1/10^{-3}$ g/(m$^2 \cdot$24 h) or less (at 25±0.5° C. and 90±2% relative humidity (RH)) measured by a method in accordance with JIS K 7129-1992.

The sealing member is formed into a concave shape by, for example, sand blasting or chemical etching.

Examples of the adhesive include photo-curable or thermo-curable adhesives having reactive vinyl groups, such as acrylic acid oligomers and methacrylic acid oligomers; moisture curable adhesives such as 2-cyanoacrylate; and thermally or chemically curable (two-liquid mixing type) adhesives, such as epoxy adhesives.

Examples of the adhesive include hot-melt polyamide, polyester, and polyolefin adhesives; and cationically UV curable epoxy resin adhesives.

Since the organic EL element may be degraded during heat treatment, an adhesive curable at a temperature from room temperature to 80° C. is preferred. A drying agent may be dispersed in the adhesive. The adhesive may be applied to the adhering portion with a commercially available dispenser or by printing such as screen printing.

It is also preferred that an inorganic or organic layer is formed as a sealing film on the outer side of the electrode on the opposite side of the supporting substrate over the organic layer to cover the electrode and the organic layer and to come into contact with the supporting substrate.

In such a case, the sealing film may be formed of any material that can block migration of substances such as water and oxygen that causes degradation of the element. Usable examples of the material include silicon oxide, silicon dioxide, and silicon nitride.

In order to reduce the fragility of the film, a sealing film having a laminate structure composed of an inorganic layer and an organic material layer is preferred.

The sealing film may be formed by any method, for example, vacuum deposition, sputtering, reactive sputtering, molecular beam epitaxy, ionized-cluster beam deposition, ion plating, plasma polymerization, atmospheric pressure plasma polymerization, plasma CVD, laser CVD, thermal CVD, or coating.

The gap between the sealing member and the displaying portion of the organic EL element is preferably filled with, in the form of a gas or liquid phase, an inert gas such as nitrogen or argon or an inactive liquid such as fluorinated hydrocarbon or silicone oil. The gap can be in a vacuum state. Alternatively, it may be filled with a hygroscopic compound.

Examples of the hygroscopic compound include metal oxides (e.g., sodium oxide, potassium oxide, calcium oxide, barium oxide, magnesium oxide, and aluminum oxide), sulfates (e.g., sodium sulfate, calcium sulfate, magnesium sulfate, and cobalt sulfate), metal halides (e.g., calcium chloride, magnesium chloride, cesium fluoride, tantalum fluoride, cerium bromide, magnesium bromide, barium iodide, and magnesium iodide), and perchlorates (e.g., barium perchlorate and magnesium perchlorate). The sulfates, metal halides, and perchlorates are suitably used in the form of anhydride.

(Protection Film, Protection Plate)

In order to enhance the mechanical strength of the element, a protection film or plate may be provided on the outer side of the sealing layer or film on the opposite side of the supporting substrate over the organic layer. In particular, when a sealing film is used for sealing the mechanical strength of the sealing film is not sufficiently high; hence, such a protection film or plate is effective.

Usable examples of the material for the protection film or plate include glass plates, polymer plates and films, and metal plates and films, which have been exemplified as materials for sealing. The polymer film is preferred from the viewpoint of a reduction in the weight and the thickness.

(Light Extraction)

It is generally said that an organic EL element generates light in a layer having a refractive index of about 1.7 to 2.1, which is higher than that of air, and can emit merely about 15% to 20% of the light generated in the light-emitting layer. This is because incident light on the interface between a transparent substrate and the air at an angle θ larger than a critical angle is totally reflected and cannot be extracted from the element, or is because light is totally reflected at the interface between the transparent electrode or light-emitting layer and the transparent substrate and is guided to the transparent electrode or the light-emitting layer to escape the light to the side face of the element.

The light extraction efficiency can be improved by roughening a surface of a transparent substrate to prevent total reflection at the interface between the transparent substrate and the air (U.S. Pat. No. 4,774,435); by providing light-condensing properties to a substrate to improve the efficiency (Japanese Patent Laid-Open No. Sho 63-314795); by forming a reflection surfaces on the side faces of an element (Japanese Patent Laid-Open No. Hei 1-220394); by disposing a flat anti-reflection layer between a substrate and a luminescent material, where the anti-reflection layer has a refractive index between those of the substrate and the luminescent material (Japanese Patent Laid-Open No. Sho 62-172691); by disposing a flat layer between a substrate and a luminescent material, where the flat layer has a refractive index lower than that of the substrate (Japanese Patent Laid-Open No. 2001-202827); and by forming a diffraction grating between any layers of a substrate, transparent electrode layer, and light-emitting layer (including on the substrate surface facing the exterior) (Japanese Patent Laid-Open No. Hei 11-283751).

In the present invention, these methods can be used in combination with the organic EL element of the present invention. In particular, the method of disposing a flat layer having a refractive index lower than that of the substrate between the substrate and the luminescent material or the method of forming a diffraction grating between any layers of a substrate, transparent electrode layer, and light-emitting layer (including on the substrate surface facing the exterior) can be suitably employed.

The present invention can provide an element exhibiting higher luminance or excellent durability by combining these methods.

In an element including a layer of a low refractive index medium with a thickness greater than light wavelength between a transparent electrode and a transparent substrate, the extraction efficiency of light from the transparent electrode to the exterior increases with a decrease in the refractive index of the medium.

Examples of materials for the low refractive index layer include aerogel, porous silica, magnesium fluoride, and fluorinated polymer layers. Since the refractive index of a transparent substrate is usually about 1.5 to 1.7, the refractive index of the low refractive index layer is preferably about 1.5 or less and more preferably 1.35 or less.

The low refractive index medium desirably has a thickness twice or more the wavelength of the light in the medium for the following reason. If the low refractive index medium has a thickness similar to the wavelength of the light, the electromagnetic waves exuding as evanescent waves penetrate into the substrate, resulting in a reduction in the effect of the low refractive index layer.

The incorporation of a diffraction grating onto the interface at which total reflection occurs or onto either media can increase the effect of enhancing the light extraction efficiency. In this method, a diffraction grating is incorporated onto the interface between any two layers or in any medium (in the transparent substrate or the transparent electrode) to extract the light that is generated in the light-emitting layer that cannot exit due to, for example, total reflection at the interface between the layers, by the use of the property of the diffraction gratings that can change the direction of light to a specific direction different from that of refraction by Bragg diffraction such as primary diffraction or secondary diffraction.

The diffraction grating to be introduced desirably has a two-dimensional array of portions having periodically different refractive indices. Because light generated in a light-emitting layer is emitted randomly in all directions, a general one-dimensional diffraction grating having a periodic refractive index distribution only in the specific direction can diffract only the light travelling in a specific direction and cannot greatly increase the light extraction efficiency.

A diffraction grating having a two-dimensional refractive index distribution can diffract light travelling in all directions, resulting in an increase in light extraction efficiency.

The diffraction grating may be introduced between any two layers or in any medium (in the transparent substrate or the transparent electrode) as described above, but is desirably introduced near the organic light-emitting layer that generates light.

The period of the diffraction grating elements is preferably about ½ to 3 times the wavelength of light in the medium.

The array of the diffraction grating elements is preferably two-dimensionally repeated such as a square lattice, a triangular lattice, or a honeycomb lattice.

(Light-Condensing Sheet)

The organic EL element of the present invention can enhance the luminance in a specific direction by condensing light in this specific direction, for example, in the front direction with respect to the light emitting plane of the element by providing, for example, a micro-lens array structure on the light extraction side of the substrate of the element or combining with a light-condensing sheet.

In an example of a micro-lens array, quadrangular pyramids having a side of 30 μm and having a vertex angle of 90 degrees are two-dimensionally arranged on the light extraction side of the substrate. The quadrangular pyramid preferably has a side of 10 to 100 μm. A side shorter than this range causes colored light due to the effect of diffraction, while a side longer than this range makes the thickness unfavorably large.

A usable light-condensing sheet is one practically used for an LED backlight of a liquid crystal display device. A typical example of the sheet is a brightness enhancing film (BEF) produced by SUMITOMO 3M Inc.

A prism sheet may have a shape, for example, an array of stripes each having a triangular cross-section with a vertex angle of 90 degrees and a pitch of 50 μm, having a round apex, having randomly changed pitches or other shapes, formed on a base material.

In order to control the emission angle of light from the light-emitting element, a light diffusion plate or film may be used in combination with the light-condensing sheet. For example, a diffusion film (Light-Up) manufactured by KIMOTO Co., Ltd. can be used.

(Application)

The organic EL element of the present invention can be used as a display device, a display, or various light emission sources. Examples of the light emission source include, but not limited to, lighting devices (home-use lamps and room lamps in vehicles), backlights for watches and liquid crystals, light sources for board advertisements, traffic lights, and optical memory media, light sources for electrophotographic copiers, light sources for optical communication instruments, and light sources for optical sensors. In particular, the organic EL element can be advantageously used as a backlight for a liquid crystal display device or a lighting source.

In the organic EL, element of the present invention, films are optionally patterned with a metal mask or by ink-jet printing during formation of the films. The patterning may be performed for only the electrodes or for the electrodes and the light-emitting layer or for all layers of the element. In the production of the element, known methods can be employed. Colors of light emitted from the organic EL element of the present invention or the compounds according to the present invention are specified with the color determined by applying the results of measurements with a spectral radiance meter CS-1000 (manufactured by Konica Minolta Sensing Co., Ltd.) to the CIE chromaticity coordinates in FIG. 4. 16 on page 108 of "Shinpen Shikisai Kagaku Handbook (New Edition Color Science Handbook)" (edited by The Color Science Association of Japan, University of Tokyo Press, 1985).

When the organic EL element of the present invention is a white-emitting element, white means that when the front luminance of a two-degree viewing angle is measured by the method described above, the chromaticity in the CIE 1931 chromaticity system at 1000 cd/m$^2$ is within a region of X=0.33±0.07 and Y=0.33±0.1.

(Display Device)

The display device of the present invention will now be described. The display device of the present invention includes the organic EL element of the present invention.

The display device of the present invention may be monochromatic or multichromatic. A multichromatic display device will now be described.

In the case of a multichromatic display device, a shadow mask is provided only during formation of the light-emitting layer and the film is formed on one side by, for example, vacuum deposition, casting, spin coating, ink jetting or printing.

In the case of patterning only the light-emitting layer, the patterning may be performed by any method and is preferably performed by vacuum deposition, ink jetting, spin coating or printing.

The structure of the organic EL element provided to the display device is appropriately selected from the structural examples of the organic EL element mentioned above.

The method of producing the organic EL element is as shown in one embodiment of the production of the organic EL element of the present invention.

When a direct current voltage of about 2 to 40 V is applied to the resulting multichromatic display device including the anode at a positive (+) polarity and the cathode at a negative (−) polarity, luminescence can be observed. Alternatively, when a voltage is applied with reverse polarity, no current flows with no light emission. When an alternating current is applied, light is emitted only in the state of the anode being positive (+) and cathode being negative (−). The alternating current to be applied may have any wave shape.

The multichromatic display device can be used as a display device, a display, or various light emission sources. In the display device and the display, full color display is achieved with three types of organic EL elements that emit blue, red, and green light.

Examples of the display device and the display include television sets, personal computers, mobile equipment, AV equipment, teletext displays, and information displays in automobiles. In particular, the display device may be used for displaying still images or moving images and the driving system in the case of using the display device for displaying moving images may be either a simple matrix (passive matrix) system or an active matrix system.

Examples of the light emission source include, but not limited to, home lamps, room lamps in vehicles, backlights for watches and liquid crystals, light sources for board advertisements, traffic lights, and optical memory media, light sources for electrophotographic copiers, light sources for optical communication instruments, and light sources for optical sensors.

An example of the display device having the organic EL element of the present invention will now be described with reference to drawings.

FIG. 1 is a schematic diagram illustrating an example display device composed of organic EL elements. The schematic diagram illustrates a display for, for example, a mobile phone to display image information through luminescence of the organic EL elements.

The display 1 is composed of a display unit A having a plurality of pixels and a control unit B performing image scanning of the display unit A based on image information.

The control unit B is electrically connected to the display unit A and sends scanning signals and image data signals to the respective pixels based on external image information.

The pixels of each scanning line receive the scanning signal and sequentially emit light according to the image data signal and the image information is displayed on the display unit A through image scanning.

Figure 2:
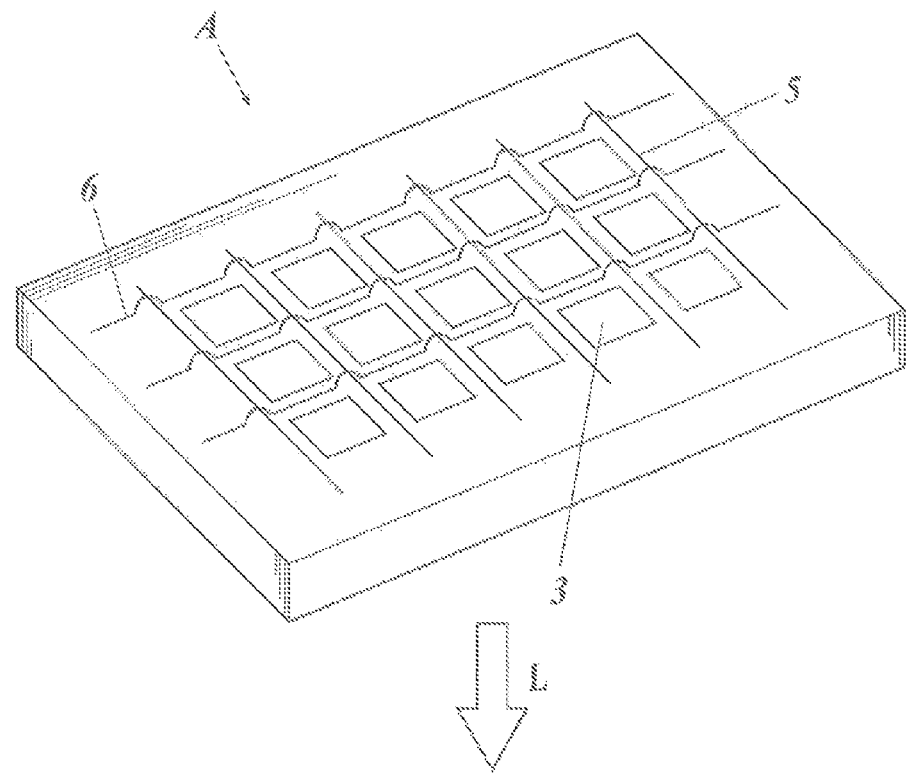
FIG. 2 is a schematic diagram of a display unit A.

FIG. 2 is a schematic diagram of the display unit A.

The display unit A includes a wiring portion including a plurality of scanning lines 5 and data lines 6, and a plurality of pixels 3 on a substrate. The main components of the display unit A will now be described.

The drawing shows light emission from the pixels 3 to the direction shown by the white arrow (downward direction).

In FIG. 2, the symbol L denotes light, which is the same in FIGS. 5 and 6 described below.

The scanning lines 5 and the data lines 6 in the wiring portion are each made of an electrically conductive material and are disposed orthogonal to each other into a grid pattern and are connected to the respective pixels 3 at the intersections (the details are not shown).

A scanning signal is applied from the scanning line 5, and then the pixels 3 receive an image data signal from the data line 6 and emit light according to the received image data.

Full color display is achieved by appropriately juxtaposing pixels that emit light in a red region, light in a green region, and light in a blue region on a single substrate.

The luminescent process of a pixel will now be described.

Figure 3:
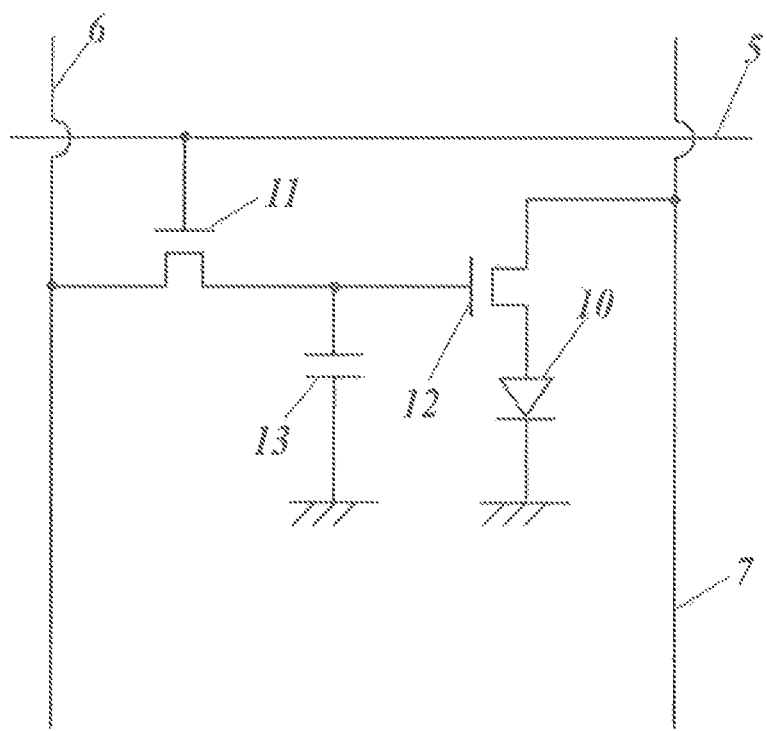
FIG. 3 is a schematic diagram of a pixel.

FIG. 3 is a schematic diagram of the pixel.

The pixel includes an organic EL element 10, a switching transistor 11, a driving transistor 12, and a capacitor 13. Full color display can be performed using organic EL elements 10 emitting red light, green light, and blue light in respective pixels juxtaposed on a single substrate.

In FIG. 3, an image data signal from the control unit B is applied to the drain electrode of the switching transistor 11 via the data line 6. A scanning signal from the control unit B is then applied to the gate electrode of the switching transistor 11 via the scanning line 5 to turn on the switching transistor 11, and the image data signal applied to the drain electrode is transmitted to gate electrodes of the capacitor 13 and the driving transistor 12.

The capacitor 13 is charged through the transmission of the image data signal depending on the potential of the image data signal, and the driving transistor 12 is turned on. In the driving transistor 12, the drain electrode is connected to a power source line 7 and a source electrode is connected to the electrode of the organic EL element 10 to supply a current to the organic EL element 10 from the power source line 7 depending on the potential of the image data signal applied to the gate electrode.

The scanning signal is transmitted to the next scanning line 5 by sequential scanning by the control unit B to turn off the switching transistor 11.

The capacitor 13 maintains the charged potential of the image data signal even after the turning-off of the switching transistor 11, and thereby the driving state of the driving transistor 12 is maintained to continue the luminescence of the organic EL element 10 until the next scanning signal is applied.

The driving transistor 12 is driven according to the potential of the subsequent image data signal in synchronization with the subsequent scanning signal applied by sequential scanning, resulting in luminescence by the organic EL element 10.

That is, luminescence by the organic EL element 10 is performed by providing a switching transistor 11 and a driving transistor 12 serving as active elements to the organic EL element 10 of each of the plurality of pixels and allowing the respective organic EL elements 10 of the pixels 3 to emit light. Such a light emitting process is called an active matrix system.

The luminescence from the organic EL element 10 may have multiple gradations according to multi-valued image data signals having different gradation potentials, or a predetermined intensity of on-off light according to a binary image data signal. The electric potential of the capacitor 13 may be maintained until the subsequent scanning signal is applied, or may be discharged immediately before the subsequent scanning signal is applied.

In the present invention, the luminescence may be driven by a passive matrix system as well as the active matrix system described above. In the passive matrix system, light is emitted from the organic EL element in response to the data signal only during scanning of the scanning signals.

Figure 4:
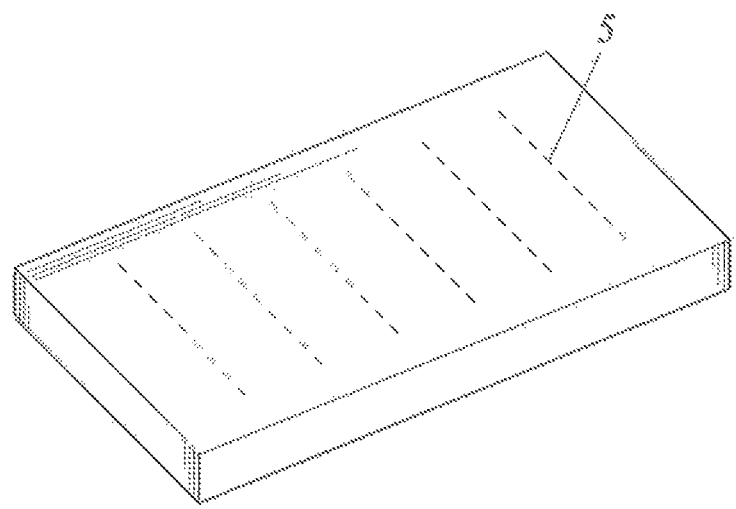
FIG. 4 is schematic diagrams of a full-color passive-matrix display device.
Figure 4:
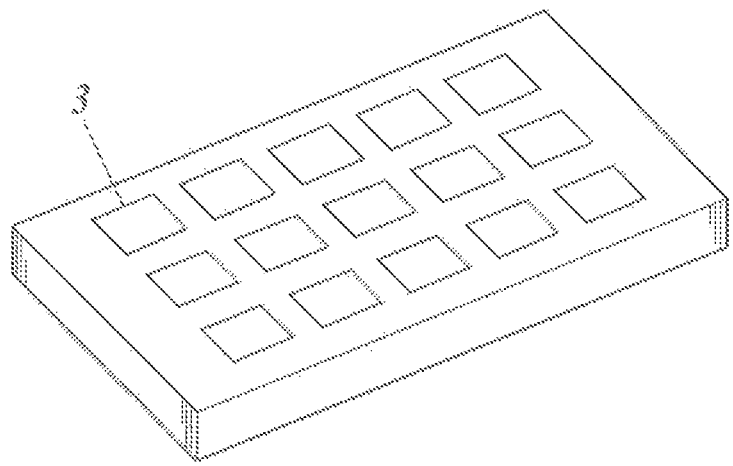
Figure 4:
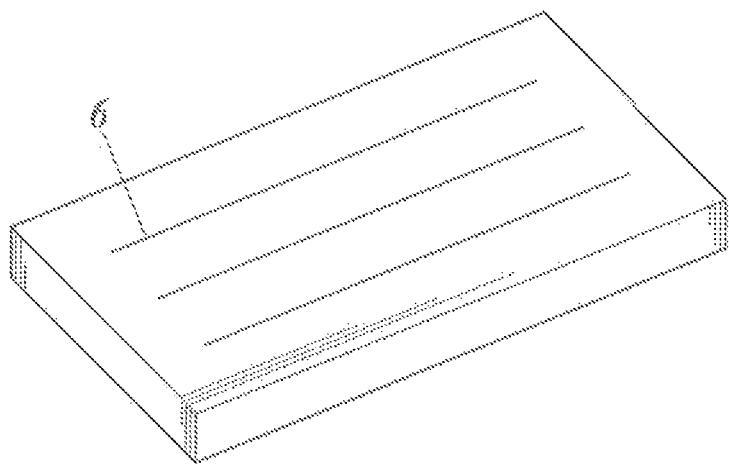

FIG. 4 includes schematic diagrams of a passive-matrix display device. In FIG. 4, a plurality of scanning lines 5 and a plurality of image data lines 6 are arrayed into a grid pattern in such a manner that pixels 3 are disposed between adjacent lines.

When a scanning signal is applied to a scanning line 5 by sequential scanning, the pixel 3 connected to the activated scanning line 5 emits light in accordance with the image data signal.

The passive matrix system does not have any active element in the pixels 3, resulting in a reduction in manufacturing cost.

(Lighting Device)

A lighting device of the present invention will now be described. The lighting device of the present invention includes the organic EL element described above.

The organic EL element of the present invention may have a resonator structure. The organic EL element having a resonator structure can be applied to, but not limited to, a light source for an optical memory medium, a light source for an electrophotographic copier, a light source for an optical communication instrument, or a light source for an optical sensor. Alternatively, the organic EL element may be used for the above-mentioned purposes by laser oscillation.

The organic EL element of the present invention may be used as a lamp such as a lighting source or an exposure light source or may be used as a projector for projecting images or a display device (display) for direct view of still or moving images.

The driving system of the display device used for playback of moving images may be either a simple matrix (passive matrix) system or an active matrix system. Furthermore, a full-color display device can be produced by employing two or more organic EL, elements of the present invention that emit light of different colors.

The organic EL material of the present invention can be applied to an organic EL element emitting substantially white light as a lighting device. The white light is generated by mixing light having different colors simultaneously emitted from a plurality of luminescent materials.

The combination of the emitted light colors may be a combination containing three maximum light emission wavelengths of three primary colors of blue, green, and red or a combination containing two maximum light emission wavelengths utilizing a relationship of complementary colors such as blue and yellow or blue-green and orange.

Furthermore, the combination of luminescent materials to obtain a plurality of colors of emitted light may be either a combination of a plurality of phosphorescent or fluorescent materials or a combination of a fluorescent or phosphorescent material and a coloring material that emits light as excited light using the light from the luminescent material. However, in the white-emitting organic EL element according to the present invention, a mere combination of a plurality of luminescent dopants has sufficient effects.

It is sufficient that a mask is disposed during formation of a light-emitting layer, a hole-transporting layer, or an electron-transporting layer to simply separate the coating through the mask. The other layers are common and do not require any patterning with a mask, and an electrode film can be formed on one side by, for example, vacuum deposition, casting, spin coating, ink jetting, or printing. The productivity is thereby enhanced.

According to this method, the element itself emits white light, unlike the white-emitting organic EL device including light emitting elements emitting different colors juxtaposed in an array form.

Any luminescent material can be used for the light-emitting layer. For example, in a backlight in a liquid crystal display element, white light may be made by selecting and combining appropriate metal complexes according to the present invention or known luminescent materials so as to match with the wavelength range corresponding to color filter (CF) characteristics.

(One Embodiment of Lighting Device of the Present Invention)

One embodiment of the lighting device including the organic EL element of the present invention will now be described.

The non-light emitting surface of the organic EL element of the present invention is covered with a glass case, and a glass substrate having a thickness of 300 µm is used as a sealing substrate. As a sealing material, an epoxy photo-curable adhesive (LUXTRACK LC0629B manufactured by Toagosei Co., Ltd.) is applied to the periphery, and the product is placed onto the cathode and is attached to the transparent supporting substrate, followed by curing the adhesive by irradiation with UV light through the glass substrate for sealing. A lighting device as shown in FIGS. 5 and 6 is formed.

Figure 5:
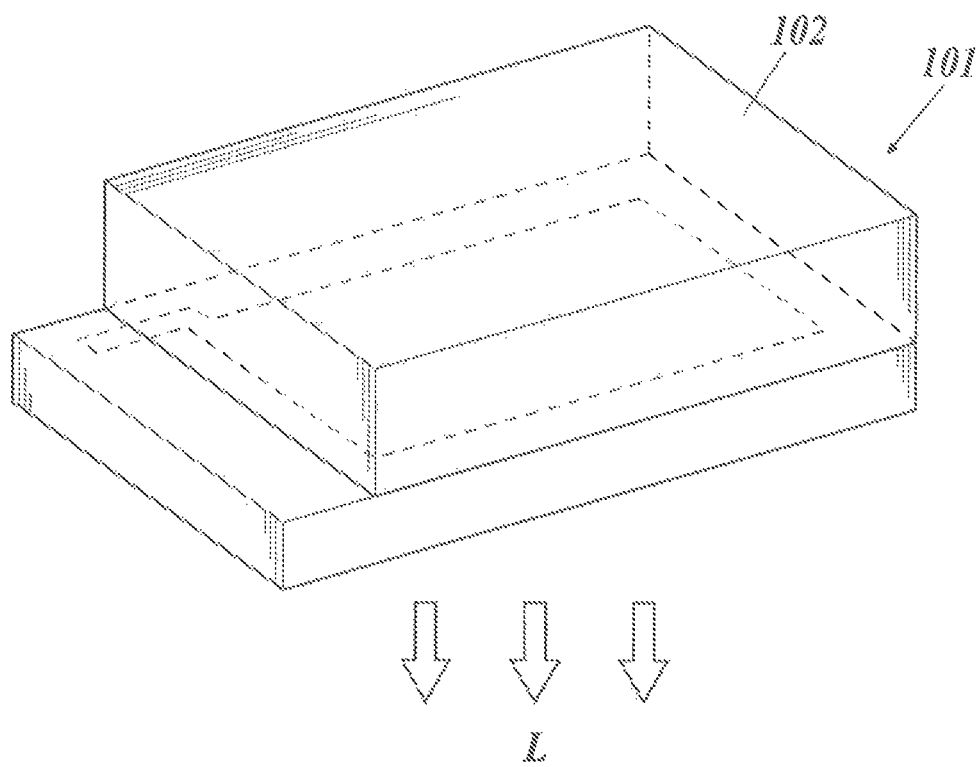
FIG. 5 is an outline diagram of a lighting device.

FIG. 5 is a schematic diagram of a lighting device. An organic EL element 101 of the present invention is covered with a glass cover 102 (sealing with the glass cover was performed in a glove box under a nitrogen atmosphere (an atmosphere of high purity nitrogen gas having a purity of at least 99.999%) to avoid contact of the organic EL element 101 with air).

Figure 6:
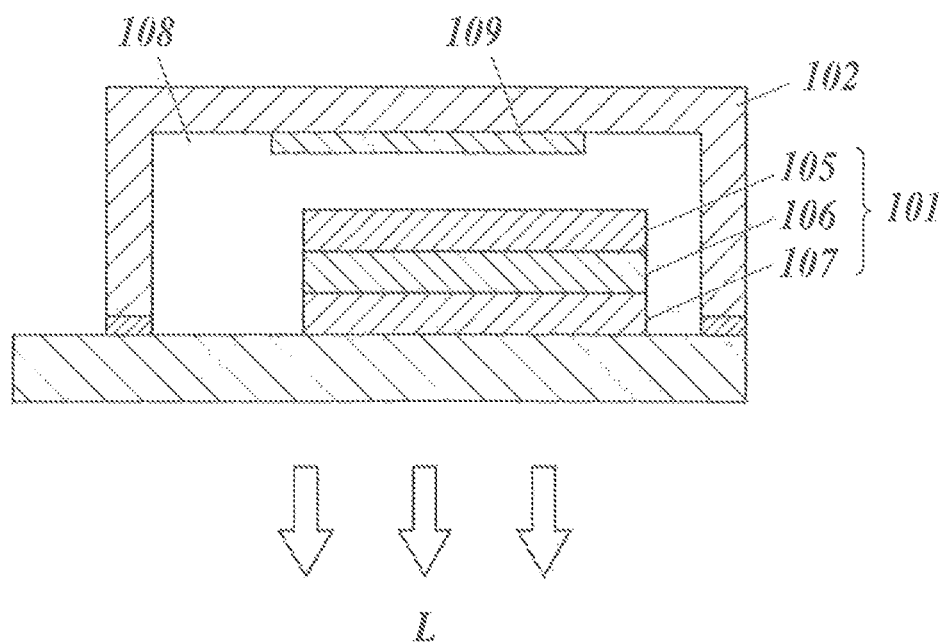
FIG. 6 is a schematic diagram of a lighting device.

FIG. 6 is a cross-sectional view of the lighting device. In FIG. 6, reference numeral 105 indicates a cathode, reference numeral 106 indicates an organic EL layer including at least a light-emitting layer, and reference numeral 107 indicates a glass substrate provided with a transparent electrode (anode).

The inside of the glass cover 102 is filled with nitrogen gas 108 and is provided with a water absorbent 109.

EXAMPLES

The present invention will now be described in detail by examples, which are not intended to limit the present invention.

The structures of compounds used in Examples are shown below:

(Dopant Compound)
[Chem. 42]
Dopant-1
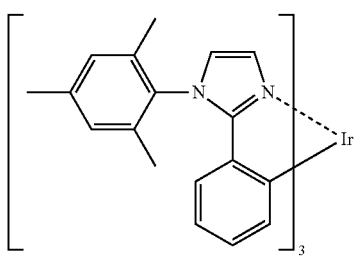
Dopant-2
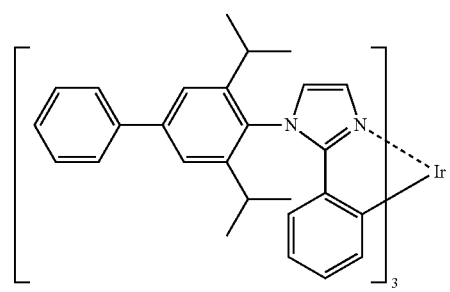
Dopant-3
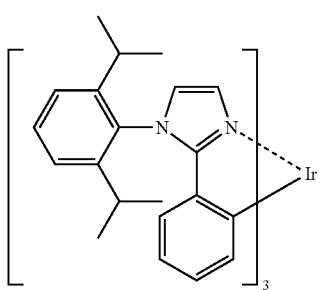
Dopant-4
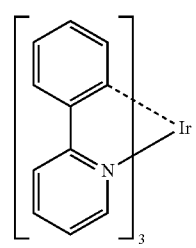
(Host Compound)
[Chem. 43]
Host-1
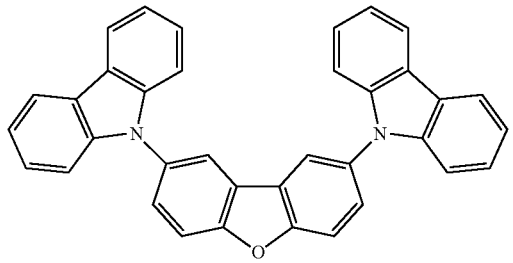
Host-2
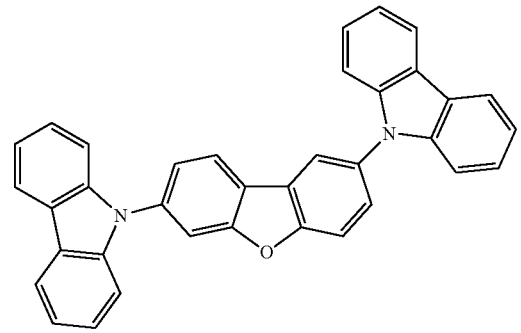
Host-3
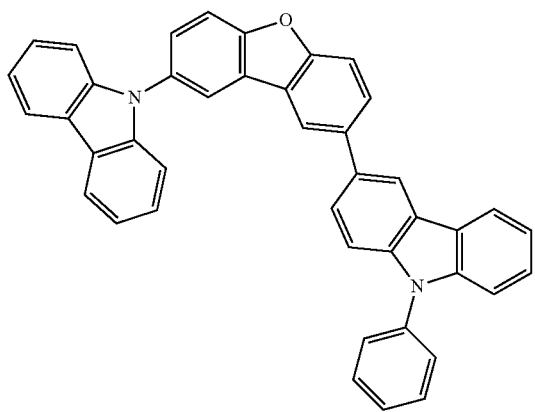
Host-4
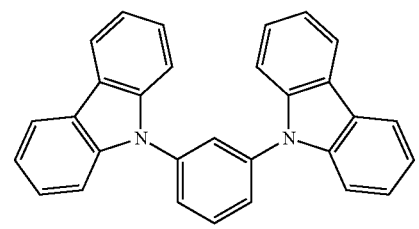

-continued
Host-5
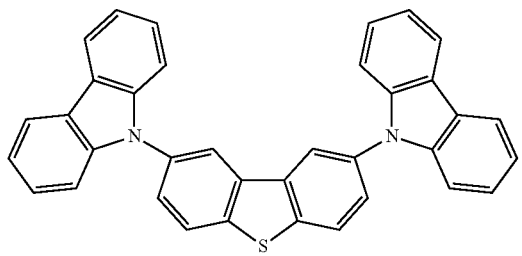
Host-6
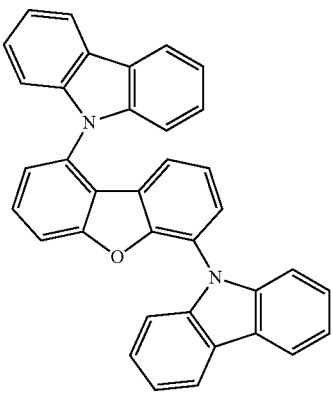
Host-7
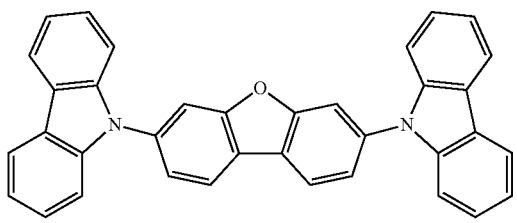
Host-8
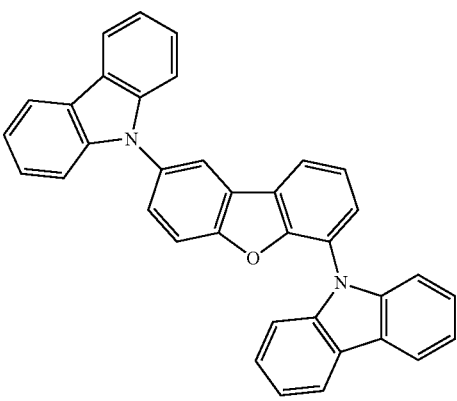
Host-9
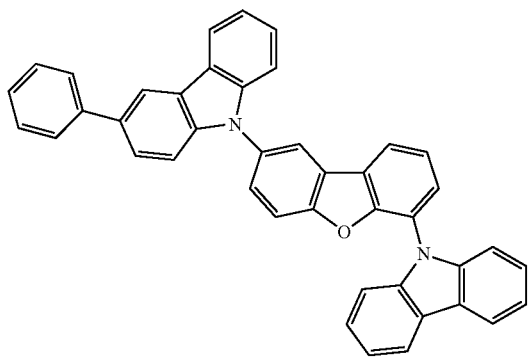
Host-10
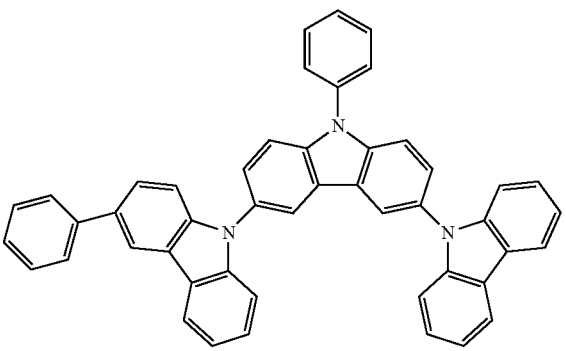
Host-11
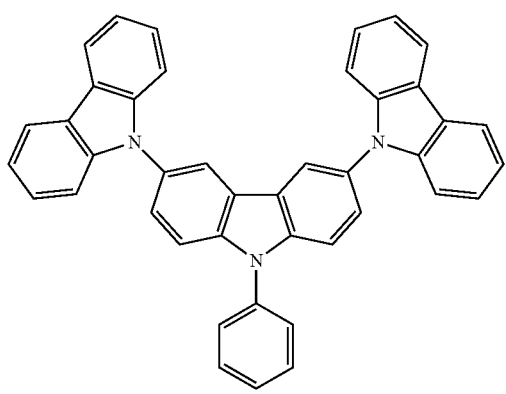
Host-12
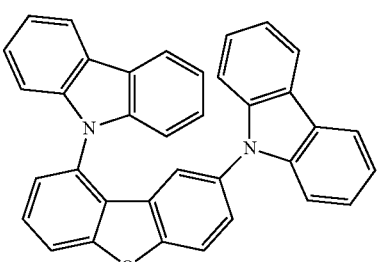

-continued

Host-13
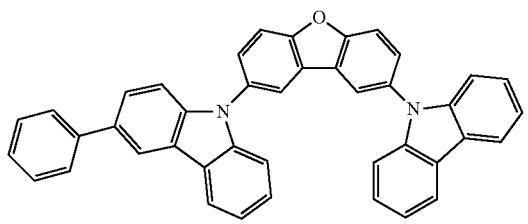

Host-14
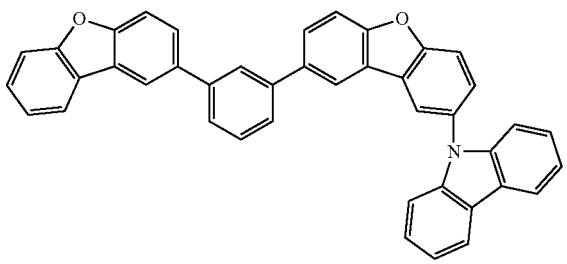

Example 1

Production of Organic EL Element (Production of Organic EL Element 100)

An organic EL element was produced as follows.

A substrate (NA45, manufactured by NH Techno Glass Corp.), prepared by forming a film of indium tin oxide (ITO) with a thickness of 100 nm on a glass substrate of 100× 100×1.1 mm, was patterned to form an anode. A transparent supporting substrate provided with the ITO transparent electrode was cleaned with ultrasonic waves in isopropyl alcohol, dried with dry nitrogen gas, and subjected to IV ozone washing for 5 minutes.

This transparent supporting substrate was fixed to the substrate holder of a commercially available vacuum deposition apparatus. A molybdenum resistance heating boat filled with 200 mg of a hole-injecting material (HT-30), a molybdenum resistance heating boat filled with 200 mg of a hole-transporting material (HT-2), a molybdenum resistance heating boat filled with 200 mg of a host compound 1 (Host-1), a molybdenum resistance heating boat filled with 200 mg of a dopant compound 1 (Dopant-1), and a molybdenum resistance heating boat filled with 200 mg of an electron-transporting material (ET-7) were placed in the vacuum deposition apparatus.

Subsequently, the pressure of a vacuum vessel was reduced to $4/10^{-4}$ Pa, and then the heating boat containing the hole-injecting material (HT-30) was heated by electrification to deposit HT-30 at a deposition rate of 0.1 nm/sec to form a 20 nm thick hole-injecting layer on the transparent supporting substrate.

Subsequently, the heating boat containing the hole-transporting material (HT-2) was heated by electrification to deposit HT-2 at a deposition rate of 0.1 nm/sec to form a 20 nm thick hole-transporting layer on the hole-injecting layer.

Subsequently, the heating boats containing the host compound 1 (Host-1) and the dopant compound 1 (Dopant-1) were heated by electrification to co-deposit Host-1 and Dopant-1 at deposition rates of 0.1 nm/sec and 0.006 nm/sec. respectively, to form a 20 nm thick light-emitting layer on the hole-transporting layer.

Subsequently, the heating boat containing the electron-transporting material (ET-7) was heated by electrification to deposit ET-7 at a deposition rate of 0.1 nm/sec to form a 20 nm thick electron-transporting layer on the light-emitting layer.

Subsequently, lithium fluoride was deposited to form 0.5 nm thick cathode buffer layer, and aluminum was deposited to form a 110 mm thick cathode. Organic EL element 100 was thereby produced.

(Production of Organic EL Elements 101 to 107 and 113 to 120)

Organic EL, elements 101 to 107 and 113 to 120 were produced as in organic EL element 100 except that the host compounds and the dopant compounds shown in Tables 1 and 2 were used for the light-emitting layers. Tables 1 and 2 show the dipole moment, relative dielectric constant, difference in dipole moment, and difference in relative dielectric constant of each of the dopant compounds and the host compounds.

(Production of Organic EL Element 108)

A substrate (NA45, manufactured by NH Techno Glass Corp.), prepared by forming a film of indium tin oxide (ITO) with a thickness of 100 nm on a glass substrate of 100× 100×1.1 mm, was patterned into an anode. This transparent supporting substrate provided with the ITO transparent electrode was cleaned with ultrasonic waves in isopropyl alcohol, dried with dry nitrogen gas, and subjected to UV ozone washing for 5 minutes.

On this transparent supporting substrate, a thin film was formed by spin coating of a solution of poly(3,4-ethylene-dioxythiophene)-polystyrene sulfonate (PEDOT/PSS, Baytron P Al 4083, manufactured by Bayer AG) diluted with pure water to 70%, at 3000 rpm for 30 seconds, followed by drying at 200° C. for 1 hour to form a first hole-transporting layer having thickness of 20 nm.

This substrate was transferred under a nitrogen atmosphere. On the first hole-transporting layer, a thin film was formed by spin coating of a solution of 10 mL of toluene containing 50 mg of a hole-transporting material (HT-16) at 1500 rpm for 30 seconds, followed by vacuum drying at 60° C. for 1 hour to form a second hole-transporting layer having a thickness of about 20 nm.

On this second hole-transporting layer, a thin film was formed by spin coating of a solution of 10 mL of butyl acetate containing 100 mg of host compound 2 (Host-2) and 10 mg of dopant compound 2 (Dopant-2) at 600 rpm for 30 seconds, followed by vacuum drying at 60° C. for 1 hour to form a light-emitting layer having a thickness of about 70 nm.

Subsequently, on this light-emitting layer, a thin film was formed by spin coating of a solution of 10 mL of hexafluoroisopropanol (HFIP) containing 50 mg of an electron-transporting material (ET-16) at 1000 rpm for 30 seconds, followed by vacuum drying at 60° C. for 1 hour to form an electron-transporting layer having a thickness of about 30 nm.

Subsequently, the substrate was fixed to the substrate holder of a vacuum deposition apparatus. The pressure of a vacuum vessel was reduced to $4/10^{-4}$ Pa, and then potassium fluoride was deposited to form a 0.4 nm thick cathode buffer layer, and aluminum was deposited to form a 110 nm thick cathode. Organic EL element 108 was thereby produced.

(Production of Organic EL Elements 109 to 112 and 121 to 126)

Organic EL elements 109 to 112 and 121 to 126 were produced as in organic EL element 108 except that the host compounds and the dopant compounds shown in Tables 1 and 2 were used for the light-emitting layers. Tables 1 and 2 show the dipole moment, relative dielectric constant, difference in dipole moment, and difference in relative dielectric constant of each of the dopant compounds and the host compounds.

(Evaluation of Organic EL Element)

The produced organic EL, elements were evaluated. The results are shown in Table 1.

For evaluation of the resulting organic EL elements, the non-light emitting surface of each of the organic EL elements was covered with a glass case. A sealing material, an epoxy photo-curable adhesive (LUXTRACK LC0629B manufactured by Toagosei Co., Ltd.), was applied to the cover glass at the periphery where the cover glass and the glass substrate of the organic EL element are in contact with each other. The product was placed onto the cathode and was attached to the transparent supporting substrate, followed by curing the adhesive by irradiating the region excluding the organic EL, element with UV light through the glass substrate for sealing. Lighting devices as shown in FIGS. 5 and 6 were thereby produced and were evaluated.

(External Quantum Efficiency (EQE))

The organic EL element was driven with a constant current of 2.5 mA/cm$^2$ at room temperature (about 23° C. to 25° C.) to emit light, and the luminance (L) (cd/m$^2$) immediately after the start of the emission of light was measured to calculate the external quantum efficiency ($\eta$).

The luminance was measured with CS-1000 (manufactured by Konica Minolta Sensing Co., Ltd.)

The external quantum efficiency is shown as a relative value compared with the value of the organic EL, element 100 defined as 100.

(Relative Lifetime)

The organic EL, elements were each driven to successively emit light with a constant current of 2.5 mA/cm$^2$ at room temperature. The time ($\tau\frac{1}{2}$) needed for decreasing the luminance to a half of the initial luminance was measured. The emission lifetime is shown as a relative value compared with the value of the organic EL element 100 defined as 100.

(External Quantum Efficiency Ratio)

The organic EL elements were each driven with a constant current of 2.5 mA/cm$^2$ and a constant current of 25 mA/cm$^2$ at room temperature (about 23° C. to 25° C.) to emit light. The luminance (L) (cd/m$^2$) immediately after the start of the emission of light was measured. The ratio of the external quantum efficiency ($\eta$) with 25 mA/cm$^2$ to the external quantum efficiency (1) with 2.5 mA/cm$^2$ was calculated. The luminance was measured with an organic EL element immediately after the formation of films and after driving for reducing the luminance to a half of the initial luminance.

The luminance was measured with CS-1000 (manufactured by Konica Minolta Sensing Co., Ltd.).

(Phosphorescence Lifetime)

The organic EL elements were each irradiated with pulsed nitrogen laser light at room temperature with an emission lifetime measuring apparatus manufactured by Hamamatsu Photonics K.K. The decay time of emission intensity after the excitation pulse irradiation was measured. The emission intensity 1 after the time t is defined by the following expression:

$$I = 10\exp(-t/\tau)$$

where 10 represents the initial emission intensity, and $\tau$ represents the emission lifetime.

The phosphorescence lifetime $\tau$ was calculated by fitting the resulting decay curve on the basis of this expression.

(Emitted Color)

The organic EL elements were each driven to successively emit light with a constant current of 2.5 mA/cm$^2$, and the emitted colors were visually evaluated.

(Primary Peak Wavelength)

The organic EL elements were each driven with a constant current of 2.5 mA/cm$^2$ at room temperature (about 23° C. to 25° C.) to emit light. Among maxima of an emission spectrum immediately after the start of the emission of light, the wavelength of the maximum at the shortest wavelength side was defined as the primary peak wavelength.

The luminance was measured with CS-1000 (manufactured by Konica Minolta Sensing Co., Ltd.).

TABLE 1

| ORGANIC EL ELEMENT | | PHOSPHORESCENT DOPANT (A) | HOST COMPOUND (B) | PHOSPHORESCENT DOPANT (A) DIPOLE MOMENT | PHOSPHORESCENT DOPANT (A) RELATIVE DIELECTRIC CONSTANT | HOST COMPOUND (B) DIPOLE MOMENT | HOST COMPOUND (B) RELATIVE DIELECTRIC CONSTANT | DIFFERENCE IN DIPOLE MOMENT (HOST (B) − PHOSPHORESCENT DOPANT (A)) |
|---|---|---|---|---|---|---|---|---|
| 100 | *1 | DOPANT1 | HOST1 | 6.33 | 2.94 | 1.61 | 3.29 | −4.72 |
| 101 | *1 | DOPANT1 | HOST2 | 6.33 | 2.94 | 0.12 | 3.19 | −6.20 |
| 102 | *1 | DOPANT1 | HOST3 | 6.33 | 2.94 | 3.29 | 3.07 | −3.04 |
| 103 | *1 | DOPANT1 | HOST4 | 6.33 | 2.94 | 1.35 | 3.14 | −4.98 |
| 104 | *1 | DOPANT2 | HOST2 | 5.65 | 3.31 | 0.12 | 3.19 | −5.53 |
| 105 | *1 | DOPANT2 | HOST5 | 5.65 | 3.31 | 1.62 | 3.37 | −4.03 |
| 106 | *1 | DOPANT2 | HOST6 | 5.65 | 3.31 | 1.22 | 3.68 | −4.43 |
| 107 | *1 | DOPANT2 | HOST7 | 5.65 | 3.31 | 1.49 | 4.30 | −4.16 |
| 108 | *1 | DOPANT3 | HOST8 | 6.09 | 3.39 | 1.18 | 3.46 | −4.91 |
| 109 | *1 | DOPANT4 | HOST2 | 6.23 | 3.48 | 0.12 | 3.19 | −6.11 |
| 110 | *1 | DOPANT2 | HOST9 | 5.65 | 3.31 | 1.37 | 3.34 | −4.28 |
| 111 | *1 | DOPANT2 | HOST10 | 5.65 | 3.31 | 5.14 | 3.34 | −0.51 |
| 112 | *1 | DOPANT2 | HOST11 | 5.65 | 3.31 | 5.02 | 3.31 | −0.63 |

TABLE 1-continued

| ORGANIC EL ELEMENT | DIFFERENCE IN RELATIVE DIELECTRIC CONSTANT (HOST (B) − PHOSPHORESCENT DOPANT (A)) | EQE (2.5 mA/cm$^2$) | RELATIVE LIFETIME | EQE (25 mA/cm$^2$)/ EQE (2.5 mA/cm$^2$) | EQE AFTER DRIVING (25 mA/cm$^2$)/EQE (2.5 mA/cm$^2$) | EMISSION LIFETIME BEFORE SINGLE FILM DETERIORATION | EMISSION COLOR | PRIMARY PEAK WAVE-LENGTH |
|---|---|---|---|---|---|---|---|---|
| 100 | 0.35 | 100 | 100 | 0.70 | 0.52 | 1.50 | BLUE | 475 |
| 101 | 0.25 | 109 | 100 | 0.33 | 0.23 | 0.98 | BLUE | 475 |
| 102 | 0.13 | 139 | 120 | 0.81 | 0.56 | 1.56 | BLUE | 475 |
| 103 | 0.20 | 132 | 87 | 0.68 | 0.51 | 1.43 | BLUE | 475 |
| 104 | −0.12 | 97 | 150 | 0.39 | 0.37 | 0.97 | BLUE | 475 |
| 105 | 0.06 | 128 | 160 | 0.61 | 0.48 | 1.20 | BLUE | 475 |
| 106 | 0.37 | 131 | 105 | 0.41 | 0.30 | 1.16 | BLUE | 475 |
| 107 | 0.99 | 136 | 24 | 0.61 | 0.36 | 1.20 | BLUE | 475 |
| 108 | 0.07 | 115 | 120 | 0.65 | 0.51 | 1.18 | BLUE | 475 |
| 109 | −0.29 | 29 | 1.3 | 0.53 | 0.41 | 1.43 | GREEN | 518 |
| 110 | 0.03 | 114 | 100 | 0.53 | 0.41 | 1.30 | BLUE | 475 |
| 111 | 0.03 | 159 | 100 | 0.88 | 0.63 | 1.35 | BLUE | 475 |
| 112 | 0.004 | 155 | 120 | 0.85 | 0.71 | 1.42 | BLUE | 475 |

*1: COMPARATIVE EXAMPLE

TABLE 2

| ORGANIC EL ELEMENT | | PHOSPHOR-ESCENT DOPANT (A) | HOST COMPOUND (B) | PHOSPHORESCENT DOPANT (A) | | HOST COMPOUND (B) | | DIFFERENCE IN DIPOLE MOMENT (HOST (B) − PHOSPHORESCENT DOPANT (A)) |
|---|---|---|---|---|---|---|---|---|
| | | | | DIPOLE MOMENT | RELATIVE DIELECTRIC CONSTANT | DIPOLE MOMENT | RELATIVE DIELECTRIC CONSTANT | |
| 113 | EXAMPLE | DOPANT2 | HOST1 | 5.65 | 3.31 | 1.61 | 3.29 | −4.04 |
| 114 | EXAMPLE | DOPANT2 | HOST12 | 5.65 | 3.31 | 2.57 | 3.06 | −3.08 |
| 115 | EXAMPLE | DOPANT2 | HOST13 | 5.65 | 3.31 | 1.71 | 3.04 | −3.94 |
| 116 | EXAMPLE | DOPANT2 | HOST4 | 5.65 | 3.31 | 1.35 | 3.14 | −4.30 |
| 117 | EXAMPLE | DOPANT2 | HOST3 | 5.65 | 3.31 | 3.29 | 3.07 | −2.36 |
| 118 | EXAMPLE | DOPANT2 | HOST14 | 5.65 | 3.31 | 2.39 | 3.20 | −3.26 |
| 119 | EXAMPLE | DOPANT4 | HOST8 | 6.23 | 3.48 | 1.18 | 3.46 | −5.05 |
| 120 | EXAMPLE | DOPANT4 | HOST5 | 6.23 | 3.48 | 1.62 | 3.37 | −4.61 |
| 121 | EXAMPLE | DOPANT3 | HOST1 | 6.09 | 3.39 | 1.61 | 3.29 | −4.48 |
| 122 | EXAMPLE | DOPANT3 | HOST3 | 6.09 | 3.39 | 3.29 | 3.07 | −2.80 |
| 123 | EXAMPLE | DOPANT3 | HOST12 | 6.09 | 3.39 | 2.57 | 3.06 | −3.52 |
| 124 | EXAMPLE | DOPANT3 | HOST9 | 6.09 | 3.39 | 1.37 | 3.34 | −4.72 |
| 125 | EXAMPLE | DOPANT3 | HOST10 | 6.09 | 3.39 | 5.14 | 3.34 | −0.95 |
| 126 | EXAMPLE | DOPANT3 | HOST11 | 6.09 | 3.39 | 5.02 | 3.31 | −1.07 |

| ORGANIC EL ELEMENT | DIFFERENCE IN RELATIVE DIELECTRIC CONSTANT (HOST (B) − PHOSPHORESCENT DOPANT (A)) | EQE (2.5 mA/cm$^2$) | RELATIVE LIFETIME | EQE (25 mA/cm$^2$)/ EQE (2.5 mA/cm$^2$) | EQE AFTER DRIVING (25 mA/cm$^2$)/EQE (2.5 mA/cm$^2$) | EMISSION LIFETIME BEFORE SINGLE FILM DETERIORATION | EMISSION COLOR | PRIMARY PEAK WAVE-LENGTH |
|---|---|---|---|---|---|---|---|---|
| 113 | −0.02 | 150 | 340 | 0.88 | 0.84 | 1.41 | BLUE | 475 |
| 114 | −0.25 | 155 | 357 | 0.95 | 0.81 | 1.54 | BLUE | 475 |
| 115 | −0.27 | 167 | 375 | 0.86 | 0.70 | 1.42 | BLUE | 475 |
| 116 | −0.17 | 139 | 421 | 0.74 | 0.69 | 1.51 | BLUE | 475 |
| 117 | −0.24 | 169 | 441 | 0.88 | 0.73 | 1.39 | BLUE | 475 |
| 118 | −0.11 | 171 | 429 | 0.84 | 0.78 | 1.30 | BLUE | 475 |
| 119 | −0.02 | 71 | 20 | 0.74 | 0.68 | 1.50 | GREEN | 518 |
| 120 | −0.11 | 73 | 14 | 0.76 | 0.70 | 1.49 | GREEN | 518 |
| 121 | −0.10 | 147 | 246 | 0.74 | 0.69 | 1.29 | BLUE | 475 |
| 122 | −0.32 | 150 | 231 | 0.82 | 0.76 | 1.60 | BLUE | 475 |
| 123 | −0.33 | 151 | 220 | 0.81 | 0.69 | 1.30 | BLUE | 475 |
| 124 | −0.05 | 148 | 256 | 0.84 | 0.80 | 1.30 | BLUE | 475 |
| 125 | −0.05 | 144 | 270 | 0.82 | 0.79 | 1.47 | BLUE | 475 |
| 126 | −0.08 | 138 | 271 | 0.86 | 0.80 | 1.50 | BLUE | 475 |

The results shown in Tables 1 and 2 demonstrate that organic EL elements 113 to 126, in which the difference in relative dielectric constant between the host compound and the phosphorescent light-emitting dopant (phosphorescent light-emitting organic metal complex) is 0 to −0.5 and the difference in dipole moment between the host compound and the phosphorescent light-emitting dopant is 0 to −5.5 debye, have a higher light extraction efficiency and a longer emission lifetime compared to those of organic EL elements 100 to 112.

INDUSTRIAL APPLICABILITY

The organic electroluminescent element of the present invention has an improved light extraction efficiency and a long lifetime and can be suitably applied to lighting devices and display devices.

REFERENCE SIGNS LIST 1 display
3 pixel
5 scanning line
6 data line
7 power source line
10 organic EL element
11 switching transistor
12 driving transistor
13 capacitor
A display unit
B control unit
101 organic EL element
102 glass cover
105 cathode
106 organic EL, layer
107 glass substrate provided with transparent electrode
108 nitrogen gas
109 water absorbent

What is claimed is:

1. An organic electroluminescent element comprising a light-emitting layer between an anode and a cathode, wherein
    the light-emitting layer comprises a phosphorescent light-emitting organic metal complex and at least one host compound;
    the host compound and the phosphorescent light-emitting organic metal complex have a difference of 0 to −0.5 in relative dielectric constant and have a difference of 0 to −5.5 debye in dipole moment; and
    the phosphorescent light-emitting organic metal complex is coordinated with a ligand having a partial structure represented by a general formula (1):

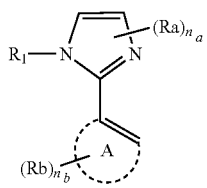

(general formula (1))

where $R_1$ represents a hydrogen atom, a halogen atom, a cyano group, or an optionally substituted alkyl, alkenyl, alkynyl, alkoxy, amino, silyl, arylalkyl, aryl, heteroaryl, alicyclic, or heteroalicyclic group;
ring A represents a 5- or 6-membered aromatic hydrocarbon ring or aromatic heterocycle;
Ra and Rb each independently represent a hydrogen atom, a halogen atom, a cyano group, or an optionally substituted alkyl, alkenyl, alkynyl, alkoxy, amino, silyl, arylalkyl, aryl, heteroaryl, alicyclic, or heteroalicyclic group;
na represents 1 or 2; and
nb represents an integer of 1 to 4.

2. The organic electroluminescent element according to claim 1, wherein the host compound and the phosphorescent light-emitting organic metal complex have a difference of 0 to −4 debye in dipole moment.

3. The organic electroluminescent element according to claim 1, wherein the phosphorescent light-emitting organic metal complex has an emission wavelength of 480 nm or less.

4. The organic electroluminescent element according to claim 1, wherein the phosphorescent light-emitting organic metal complex is coordinated with a ligand having a partial structure represented by a general formula (2):

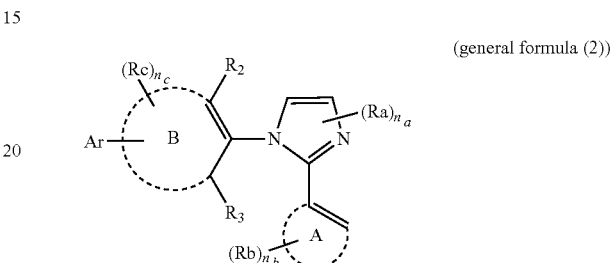

(general formula (2))

where rings A and B each independently represent a 5- or 6-membered aromatic hydrocarbon ring or aromatic heterocycle;
Ar represents a 5- or 6-membered aromatic hydrocarbon ring, aromatic heterocyclic ring, alicyclic ring, or heteroalicyclic ring;
$R_2$ and $R_3$ each independently represent a hydrogen atom, a halogen atom, a cyano group, or an optionally substituted alkyl, alkenyl, alkynyl, alkoxy, amino, silyl, arylalkyl, aryl, heteroaryl, alicyclic, or heteroalicyclic group;
Ra, Rb, and Rc each independently represent a hydrogen atom, a halogen atom, a cyano group, or an optionally substituted alkyl, alkenyl, alkynyl, alkoxy, amino, silyl, arylalkyl, aryl, heteroaryl, alicyclic, or heteroalicyclic group;
na and nc each independently represent 1 or 2; and
nb represents an integer of 1 to 4.

5. The organic electroluminescent element according to claim 4, wherein $R_2$ and/or $R_3$ represents an alkyl group.

6. The organic electroluminescent element according to claim 5, wherein $R_2$ and/or $R_3$ represents an alkyl group having two or more carbon atoms.

7. The organic electroluminescent element according to claim 4, wherein $R_2$ and $R_3$ represent alkyl groups.

8. The organic electroluminescent element according to claim 7, wherein $R_2$ and $R_3$ represent alkyl groups having two or more carbon atoms.

9. The organic electroluminescent element according to claim 4, wherein ring A is a benzene ring.

10. The organic electroluminescent element according to claim 4, wherein Ar is a benzene ring.

11. The organic electroluminescent element according to claim 1, wherein the phosphorescent light-emitting organic metal complex is an organic metal complex represented by a general formula (3):

(general formula (3))

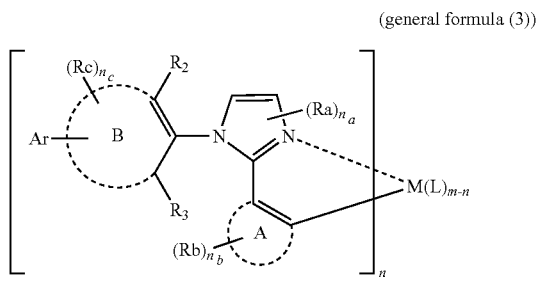

where rings A and B each independently represent a 5- or 6-membered aromatic hydrocarbon ring or aromatic heterocycle;
Ar represents a 5- or 6-membered aromatic hydrocarbon ring, aromatic heterocyclic ring, alicyclic ring, or heteroalicyclic ring;
$R_2$ and $R_3$ each independently represent a hydrogen atom, a halogen atom, a cyano group, or an optionally substituted alkyl, alkenyl, alkynyl, alkoxy, amino, silyl, arylalkyl, aryl, heteroaryl, alicyclic, or heteroalicyclic group;
Ra, Rb, and Rc each independently represent a hydrogen atom, a halogen atom, a cyano group, or an optionally substituted alkyl, alkenyl, alkynyl, alkoxy, amino, silyl, arylalkyl, aryl, heteroaryl, alicyclic, or heteroalicyclic group;
na and nc each independently represent 1 or 2;
nb represents an integer of 1 to 4;
L represents one or more of monoanionic bidentate ligands coordinated to M;
M represents a transition metal atom having an atomic number of 40 or more and belonging to any one of Groups 8 to 10 of the periodic table;
m represents an integer of 1 to 3;
n represents 1 or more; and
m+n is 2 or 3.

12. The organic electroluminescent element according to claim 11, wherein the general formula (3) is represented by a general formula (3-1):

(general formula (3-1))

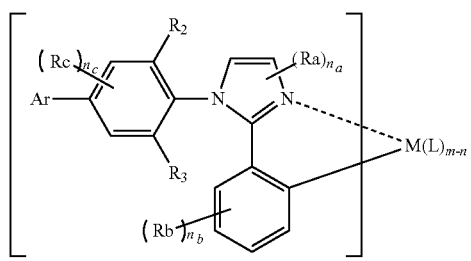

where Ar, $R_2$, $R_3$, Ra, Rb, Rc, na, nb, nc, M, L, m, and n are synonymous with Ar, $R_2$, $R_3$, Ra, Rb, Rc, na, nb, nc, M, L, m, and n in the general formula (3).

13. The organic electroluminescent element according to claim 12, wherein M is Ir.

14. The organic electroluminescent element according to claim 1, wherein the host compound has a partial structure represented by a general formula (4):

(general formula (4))

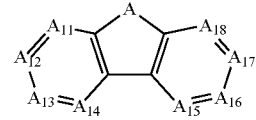

where A represents an O or S atom or an $NR_1$ group;
$A_{11}$ to $A_{18}$ each independently represent a N atom or $CR_2$; and
$R_1$ and $R_2$ each independently represent a bonding hand, a hydrogen atom, or a substituent;
and if there are a plurality of $CR_2$, they may be the same or different.

15. An organic electroluminescent element comprising a light-emitting layer between an anode and a cathode, wherein
the light-emitting layer comprises a phosphorescent light-emitting organic metal complex and at least one host compound;
the host compound and the phosphorescent light-emitting organic metal complex have a difference of 0 to –0.5 in relative dielectric constant and have a difference of 0 to –5.5 debye in dipole moment; and
the host compound has a partial structure represented by a general formula (4):

(general formula (4))

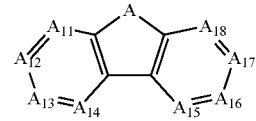

Where A represents an O or S atom or an $NR_1$ group;
$A_{11}$ to $A_{18}$ each independently represent a N atom or $CR_2$; and
$R_1$ and $R_2$ each independently represent a bonding hand, a hydrogen atom, or a substituent;
and if there are a plurality of $CR_2$, they may be the same or different.

16. The organic electroluminescent element according to claim 15, wherein the host compound and the phosphorescent light-emitting organic metal complex have a difference of 0 to –4 debye in dipole moment.

17. The organic electroluminescent element according to claim 15, wherein the phosphorescent light-emitting organic metal complex has an emission wavelength of 480 nm or less.

18. The organic electroluminescent element according to claim 15, wherein the phosphorescent light-emitting organic metal complex is coordinated with a ligand having a partial structure represented by a general formula (2):

(general formula (2))

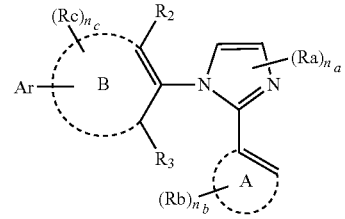

Where rings A and B each independently represent a 5- or 6-membered aromatic hydrocarbon ring or aromatic heterocycle;

Ar represents a 5- or 6-membered aromatic hydrocarbon ring, aromatic heterocyclic ring, alicyclic ring, or heteroalicyclic ring;

$R_2$ and $R_3$ each independently represent a hydrogen atom, a halogen atom, a cyano group, or an optionally substituted alkyl, alkenyl, alkynyl, alkoxy, amino, silyl, arylalkyl, aryl, heteroaryl, alicyclic, or heteroalicyclic group;

Ra, Rb, and Rc each independently represent a hydrogen atom, a halogen atom, a cyano group, or an optionally substituted alkyl, alkenyl, alkynyl, alkoxy, amino, silyl, arylalkyl, aryl, heteroaryl, alicyclic, or heteroalicyclic group;

na and nc each independently represent 1 or 2; and nb represents an integer of 1 to 4.

19. The organic electroluminescent element according to claim 15, wherein the phosphorescent light-emitting organic metal complex is an organic metal complex represented by a general formula (3):

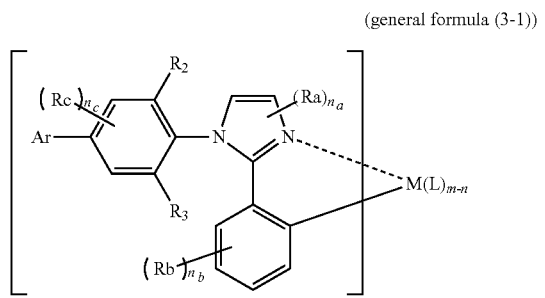

(general formula (3-1))

Where rings A and B each independently represent a 5- or 6-membered aromatic hydrocarbon ring or aromatic heterocycle;

Ar represents a 5- or 6-membered aromatic hydrocarbon ring, aromatic heterocyclic ring, alicyclic ring, or heteroalicyclic ring;

$R_2$ and $R_3$ each independently represent a hydrogen atom, a halogen atom, a cyano group, or an optionally substituted alkyl, alkenyl, alkynyl, alkoxy, amino, silyl, arylalkyl, aryl, heteroaryl, alicyclic, or heteroalicyclic group;

Ra, Rb, and Rc each independently represent a hydrogen atom, a halogen atom, a cyano group, or an optionally substituted alkyl, alkenyl, alkynyl, alkoxy, amino, silyl, arylalkyl, aryl, heteroaryl, alicyclic, or heteroalicyclic group;

na and nc each independently represent 1 or 2;

nb represents an integer of 1 to 4;

L represents one or more of monoanionic bidentate ligands coordinated to M;

M represents a transition metal atom having an atomic number of 40 or more and belonging to any one of Groups 8 to 10 of the periodic table;

m represents an integer of 1 to 3;

n represents 1 or more; and m+n is 2 or 3.

* * * * *